(12) United States Patent
Sauerberg et al.

(10) Patent No.: US 7,220,877 B2
(45) Date of Patent: *May 22, 2007

(54) COMPOUNDS, THEIR PREPARATION AND USE

(75) Inventors: Per Sauerberg, Farum (DK); Paul Stanley Bury, Burnley (GB); Lone Jeppesen, Virum (DK); John Patrick Mogensen, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 430 days.

This patent is subject to a terminal disclaimer.

(21) Appl. No.: 10/272,613

(22) Filed: Oct. 16, 2002

(65) Prior Publication Data

US 2003/0109579 A1    Jun. 12, 2003

Related U.S. Application Data

(60) Provisional application No. 60/330,346, filed on Oct. 18, 2001.

(30) Foreign Application Priority Data

Oct. 17, 2001 (DK) .......................... PA 2001 01524

(51) Int. Cl.
*C07C 321/00* (2006.01)
*C07C 315/00* (2006.01)

(52) U.S. Cl. ...................... 560/147; 562/581

(58) Field of Classification Search ............. 560/179, 560/180, 183, 184, 187, 190, 192, 205, 226, 560/227, 128, 55, 76, 101, 102; 562/405, 562/465, 466, 480, 590, 595, 596, 598, 602

See application file for complete search history.

(56) References Cited

U.S. PATENT DOCUMENTS 4,148,915 A    4/1979  Thuillier et al. ............ 424/308

5,306,726 A    4/1994  Hulin ........................ 514/375

FOREIGN PATENT DOCUMENTS

| EP | 0597102 A1 | 5/1994 |
|---|---|---|
| WO | WO 91/19702 | 12/1991 |
| WO | WO 94/01420 | 1/1994 |
| WO | WO 94/13650 | 6/1994 |
| WO | WO 95/03038 | 2/1995 |
| WO | WO 95/17394 | 6/1995 |
| WO | WO 96/04260 | 2/1996 |
| WO | WO 97/25042 | 7/1997 |
| WO | WO 97/36579 | 10/1997 |
| WO | WO 99/08501 | 2/1999 |
| WO | WO 99/16758 | 4/1999 |
| WO | WO 99/19313 | 4/1999 |
| WO | WO 99/63983 | 12/1999 |
| WO | WO 01/00603 A1 | 1/2001 |
| WO | WO 01/55085 A1 | 8/2001 |
| WO | WO 01/55086 A1 | 8/2001 |

OTHER PUBLICATIONS

Berger et al., The Journal of Biological Chemistry, vol. 274, No. 10, pp. 6718-6725 (1999).
Leibowitz et al., FEBS Letters vol. 473, pp. 333-336 (2000).
Oliver et al., PNAS, vol. 98, No. 9, pp. 5306-5311 (2001).

*Primary Examiner*—Thurman K. Page
*Assistant Examiner*—Karl Puttlitz
(74) *Attorney, Agent, or Firm*—Rosemarie R. Wilk-Orescan; Reza Green; Richard W. Bork

(57) ABSTRACT

A novel class of dicarboxylic acid derivatives, the use of these compounds as pharmaceutical compositions, pharmaceutical compositions comprising the compounds and methods of treatment employing these compounds and compositions. The present compounds may be useful in the treatment and/or prevention of conditions mediated by Peroxisome Proliferator-Activated Receptors (PPAR).

69 Claims, No Drawings

COMPOUNDS, THEIR PREPARATION AND USE

CROSS-REFERENCE TO RELATED APPLICATIONS

This application claims priority under 35 U.S.C. 119 of Danish application no. PA 2001 01524 filed Oct. 17, 2001 and U.S. application No. 60/330,346 filed Oct. 18, 2001, the contents of which are fully incorporated herein by reference.

FIELD OF THE INVENTION

The present invention relates to novel dicarboxylic acid derivatives, to the use of these compounds as pharmaceutical compositions, to pharmaceutical compositions comprising the compounds and to a method of treatment employing these compounds and compositions. More specifically, the compounds of the invention can be utilized in the treatment and/or prevention of conditions mediated by the Peroxisome Proliferator-Activated Receptors (PPAR).

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialized proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarized as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

PPARδ activation was initially reported not to be involved in modulation of glucose or triglyceride levels. (Berger et al., *j. Biol. Chem.*, 1999, Vol 274, pp. 6718–6725). Later it has been shown that PPARδ activation leads to increased levels of HDL cholesterol in dbldb mice (Leibowitz et al. FEBS letters 2000, 473, 333–336). Further, a PPARδ agonist when dosed to insulin-resistant middle-aged obese rhesus monkeys caused a dramatic dose-dependent rise in serum HDL cholesterol while lowering the levels of small dense LDL, fasting triglycerides and fasting insulin (Oliver et al. PNAS 2001, 98, 5306–5311).The same paper also showed that PPARδ activation increased the reverse cholesterol transporter ATP-binding cassette A1 and induced apolipoprotein A1-specific cholesterol efflux. Taken together these observations suggest that PPARδ activation is useful in the treatment and prevention of cardiovascular diseases and conditions including atherosclerosis, hypertriglyceridemia, and mixed dyslipidaemia (PCT publication WO 01/00603 (Chao et al.).

A number of compounds have been reported to be useful in the treatment of hyperglycemia, hyperlipidemia and hypercholesterolemia (U.S. Pat. No. 5,306,726, PCT Publications nos. WO91/19702, WO 95/03038, WO 96/04260, WO 94/13650, WO 94/01420, WO 97/36579, WO 97/25042, WO 95/17394, WO 99/08501, WO 99/19313, WO 99/16758 and WO 01/00603). WO 99/63983 discloses multibinding compounds, which bind to PPARγ receptors.

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

This indicate that research for compounds displaying various degree of PPARα, PPARγ and PPARδ activation should lead to the discovery of efficacious triglyceride and/or cholesterol and/or glucose lowering drugs that have great potential in the treatment of diseases such as type 2 diabetes, dyslipidaemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

DEFINITIONS

In the structural formulas given herein and throughout the present specification the following terms have the indicated meaning:

The terms "$C_{1-n'}$-alkyl" wherein n' can be from 2 through 6, as used herein, represent a linear or branched, saturated hydrocarbon chain having the indicated number of carbon atoms. Examples of such groups include, but are not limited to methyl, ethyl, n-propyl, isopropyl, butyl, isobutyl, sec-butyl, tert-butyl, pentyl, isopentyl, hexyl, isohexyl and the like.

The term "$C_{3-n'}$-cycloalkyl" wherein n' can be from 4 through 6, as used herein, alone or in combination, represent a saturated monocyclic hydrocarbon group having the indicated number of carbon atoms. Examples of such groups include, but are not limited to cyclopropyl, cyclobutyl, cyclopentyl, cyclohexyl and the like.

The terms "$C_{1-n'}$-alkylene" wherein n' can be from 2 through 6, as used herein, represent a divalent linear or branched, saturated hydrocarbon chain having the indicated number of carbon atoms. Examples of such groups include, but are not limited to methylene, ethylene, trimethylene, tetramethylene, propylene, ethylethylene, methylpropylene, ethylpropylene and the like.

The terms "$C_{4-n'}$-cycloalkylene" wherein n' can be from 5 through 6, as used herein, represent a divalent saturated monocyclic hydrocarbon group having the indicated number of carbon atoms. Examples of such groups include, but are not limited to cyclopentylene, cyclohexylene and the like.

The term "$C_{2-n'}$-alkenyl" wherein n' can be from 3 through 6, as used herein, represent an olefinically unsaturated branched or straight hydrocarbon group having from 2 to the specified number of carbon atoms and at least one double bond. Examples of such groups include, but are not limited to, vinyl, 1-propenyl, 2-propenyl, allyl, iso-propenyl, 1,3-butadienyl, 1-butenyl, hexenyl, pentenyl and the like.

The term "$C_{2-n'}$-alkenylene" wherein n' can be from 3 through 6, as used herein, represent an divalent olefinically unsaturated branched or straight hydrocarbon group having from 2 to the specified number of carbon atoms and at least one double bond. Examples of such groups include, but are not limited to ethenylene (—CH=CH—), the propenylene isomers (e.g., —CH$_2$CH=CH— and —C(CH$_3$)=CH—), the butenylene isomers (e.g., —CH$_2$CH=C(CH$_3$)— and —CH$_2$CH$_2$CH=CH—) and the like.

The terms "$C_{4-n'}$-alkenynyl" as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like, especially preferred is 1-pentene-4-yne.

The term "$C_{4-n'}$-cycloalkenylene" wherein n' can be from 5 through 6, as used herein, represent an divalent unsaturated monocyclic hydrocarbon group having from 4 to the specified number of carbon atoms and at least one double bond. Examples of such groups include, but are not limited to cyclohexenylene and the like.

The term "$C_{3-n'}$-alkynyl" wherein n' can be from 4 through 6, as used herein, represent an unsaturated branched or straight hydrocarbon group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The term "$C_{2-n'}$-alkynylene" wherein n' can be from 3 through 6, as used herein, represent an divalent unsaturated branched or straight hydrocarbon group having from 2 to the specified number of carbon atoms and at least one triple bond. Examples of such groups include, but are not limited to, propynylene (—CH$_2$C≡C—), the butynylene isomers (e.g., —CH$_2$CH$_2$C≡C—, —CH$_2$C≡C—CH$_2$—), and the like.

The term "$C_{4-n'}$-alkenynylene" wherein n' can be from 5 through 9 as used herein, represent an divalent unsaturated branched or straight hydrocarbon group having from 4 to the specified number of carbon atoms and both at least one double bond and at least one triple bond. Examples of such groups include, but are not limited to, 1-penten-4-ynylene, 3-penten-1-ynylene, 1,3-hexadiene-5-ynylene and the like.

The term "$C_{3-n'}$-divalent unsaturated carbon chain" wherein n' can be from 4 through 9, as used herein, represent an divalent unsaturated branched or straight hydrocarbon group having from 3 to the specified number of carbon atoms and at least one double bound (alkenylen) or at least one triple bound (alkynylene) or a combination hereof (alkenynylene). Examples of such groups include, but are not limited to ethenylene (—CH=CH—), the propenylene isomers (e.g., —CH$_2$CH=CH— and —C(CH$_3$)=CH—), the butenylene isomers (e.g., —CH$_2$CH=C(CH$_3$)— and —CH$_2$CH$_2$CH=CH—), propynylene(—CH$_2$C≡C—), the butynylene isomers (e.g., —CH$_2$CH$_2$C≡C—, —CH$_2$C≡C—CH$_2$—), 1-penten-4-ynylene, 3-penten-1-ynylene, 1,3-hexadiene-5-ynylene and the like.

The term "$C_{1-n'}$-alkoxy" wherein n' can be from 2 through 6, as used herein, alone or in combination, refers to a straight or branched configuration linked through an ether oxygen having its free valence bond from the ether oxygen. Examples of such linear alkoxy groups include, but are not limited to methoxy, ethoxy, propoxy, butoxy, pentoxy, hexoxy and the like. Examples of such branched alkoxy include, but are not limited to isopropoxy, sec-butoxy, tert-butoxy, isopentyloxy, isohexyloxy and the like.

The term "$C_{3-n'}$-cycloalkoxy" wherein n' can be from 4 through 6, as used herein, alone or in combination, represent a saturated monocyclic hydrocarbon group having the indicated number of carbon atoms linked through an ether oxygen having its free valence bond from the ether oxygen. Examples of such cycloalkoxy groups include, but are not limited to cyclopropyloxy, cyclobutyloxy, cyclopentyloxy, cyclohexyloxy and the like.

The term "$C_{1-n'}$-alkylthio" wherein n' can be from 2 through 6, as used herein, alone or in combination, refers to a straight or branched monovalent substituent comprising a $C_{1-6}$-alkyl group linked through a divalent sulfur atom having its free valence bond from the sulfur atom and having 1 to 6 carbon atoms. Examples of such groups include, but are not limited to methylthio, ethylthio, propylthio, butylthio, pentylthio and the like.

The term "$C_{3-n'}$-cycloalkylthio" wherein n' can be from 4 through 6, as used herein, alone or in combination, represent a saturated monocyclic hydrocarbon group having the indicated number of carbon atoms linked through a divalent sulfur atom having its free valence bond from the sulfur atom. Examples of such cycloalkoxy groups include, but are not limited to cyclopropylthio, cyclobutylthio, cyclopentylthio, cyclohexylthio and the like.

The term "aryl" as used herein refers to an aromatic monocyclic or an aromatic fused bi- or tricyclic hydrocarbon group. Examples of such groups include, but are not limited to phenyl, naphthyl, anthracenyl, phenanthrenyl, azulenyl and the like.

The term "arylene" as used herein refers to divalent aromatic monocyclic or a divalent aromatic fused bi- or tricyclic hydrocarbon group (derived from aryl). Examples of such groups include, but are not limited to phenylene, naphthylene and the like.

The term "heteroaryl" as used herein, alone or in combination, refers to a divalent substituent comprising a 5–7 membered monocyclic aromatic system or a 8–10 membered bicyclic fused aromatic system containing one or more heteroatoms selected from nitrogen, oxygen and sulfur or a 10–16 membered tricyclic fused aromatic system containing one or more heteroatoms selected from nitrogen, oxygen and sulfur e.g. furyl, thienyl, pyrrolyl, imidazolyl, pyrazolyl, triazolyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinnyl, indolyl, benzimidazolyl, benzofuranyl, pteridinyl, purinyl, carbazolyl, β-carbolinyl, acridinyl, phenanthrolinyl, phenazinyl, phenoxazinyl, phenothiazinyl and the like The term "heteroarylene" as used herein, alone or in combination, refers to a divalent substituent (derived from heteroaryl) comprising a 5–7 membered monocyclic aromatic system or a 8–10 membered bicyclic aromatic system containing one or more heteroatoms selected from nitrogen, oxygen and sulfur or a 10–16 membered tricyclic fused aromatic system containing one or more heteroatoms selected from nitrogen, oxygen and sulfur e.g. furylene, thienylene, pyrrolylene, imidazolylene, pyrazolylene, triazolylene, pyrazinylene, pyrimidinylene, pyridazinylene, isothiazolylene, isoxazolylene, oxazolylene, oxadiazolylene, thiadiazolylene, quinolylene, isoquinolylene, quinazolinylene, quinoxalinnylene, indolylene, benzimidazolylene, benzofuranylene, pteridinylene, purinylene carbazolylene, β-carbolinylene, acridinylene, phenanthrolinylene, phenazinylene, phenoxazinylene, phenothiazinylene and the like.

The term "a divalent polycyclic ringsystem" as used herein refers to a divalent group formed from a polycyclic ringsystem containing indenpending of each other 2 trough 4 aryl or heteroaryl ring systems joined by single bonds. Example of such bi-, ter- and quaterarylylene having 2 through 4 identical aryl ring systems include, but are not limited to biphenylylene, binaphthylylene, terphenylylene, ternaphthylylene, quaterphenylylene, quaternaphthylylene and the like. Example of such bi-, ter- and quaterheteroarylylene having 2 through 4 identical heteroaryl ring systems include, but are not limited to bipyridylylene, biindolylylene, terpyridylylene, terindolylylene, quaterpyridylylene, quaterindolylylene and the like. Example of such polycyclic ringsystems having non identical ring systems include, but are not limited to diphenylpyridine and the like.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "aralkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphthyl)ethyl and the like.

The term "halogen" means fluorine, chlorine, bromine or iodine.

The term "treatment" as used herein includes treatment, prevention and management of conditions mediated by Peroxisome Proliferator-Activated Receptors (PPAR).

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

DESCRIPTION OF THE INVENTION

The present invention relates to compounds of the general formula (I):

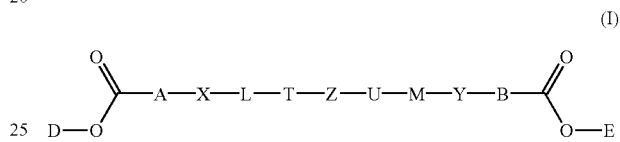

wherein A is $C_{1-3}$-alkylene which is optionally substituted with one or more substituents selected from
halogen or
$C_{1-3}$-alkyl, $C_{1-6}$-alkoxy, $C_{3-6}$-cycloalkoxy, $C_{1-6}$-alkylthio, $C_{3-6}$-cycloalkylthio or aralkoxy each of which is optionally substituted with halogen; or
$NR_1R_2$ wherein $R_1$ represents hydrogen or $C_{1-3}$-alkyl and $R_2$ represents —$R_3$—(C=O)—$R_4$ wherein:
$R_3$ represents $C_{1-6}$-alkylene, $C_{2-6}$-alkenylene, $C_{4-6}$-cycloalkylene, $C_{4-6}$-cycloalkenylene, or arylene optionally substituted with one or more halogens;
$R_4$ represents aryl optionally substituted with one or more halogens; or A is —O—A' or —S—A' wherein —O— or —S— is linked to X in formula (I) and wherein A' is $C_{1-3}$-alkylene which is optionally substituted with one or more substituents selected from
halogen or
$C_{1-3}$-alkyl, $C_{1-6}$-alkoxy, $C_{3-6}$-cycloalkoxy, $C_{1-6}$-alkylthio, $C_{3-6}$-cycloalkylthio or aralkoxy each of which is optionally substituted with halogen; or
$NR_1R_2$ wherein $R_1$ represents hydrogen or $C_{1-3}$-alkyl and $R_2$ represents —$R_3$—(C=O)—$R_4$ wherein:
$R_3$ represents $C_{1-6}$-alkylene, $C_{2-6}$-alkenylene, $C_{4-6}$-cycloalkylene, $C_{4-6}$-cycloalkenylene, or arylene optionally substituted with one or more halogens;
$R_4$ represents aryl optionally substituted with one or more halogens; and B is $C_{1-3}$-alkylene which is optionally substituted with one or more substituents selected from
halogen or
$C_{1-3}$-alkyl, $C_{1-6}$-alkoxy, $C_{3-6}$-cycloalkoxy, $C_{1-6}$-alkylthio, $C_{3-6}$-cycloalkylthio or aralkoxy each of which is optionally substituted with halogen; or
$NR_1R_2$ wherein $R_1$ represents hydrogen or $C_{1-3}$-alkyl and $R_2$ represents —$R_3$—(C=O)—$R_4$ wherein:
$R_3$ represents $C_{1-6}$-alkylene, $C_{2-6}$-alkenylene, $C_{4-6}$-cycloalkylene, $C_{4-6}$-cycloalkenylene, or arylene optionally substituted with one or more halogens;

R$_4$ represents aryl optionally substituted with one or more halogens; or

B is —O—B' or —S—B' wherein —O— or —S— is linked to Y in formula (I) and wherein B' is C$_{1-3}$-alkylene which is optionally substituted with one or more substituents selected from
  halogen or
  C$_{1-3}$-alkyl, C$_{1-6}$-alkoxy, C$_{3-6}$-cycloalkoxy, C$_{1-6}$-alkylthio, C$_{3-6}$-cycloalkylthio or aralkoxy each of which is optionally substituted with halogen; or
  NR$_1$R$_2$ wherein R$_1$ represents hydrogen or C$_{1-3}$-alkyl and R$_2$ represents —R$_3$—(C=O)—R$_4$ wherein:
    R$_3$ represents C$_{1-6}$-alkylene, C$_{2-6}$-alkenylene, C$_{4-6}$-cycloalkylene, C$_{4-6}$-cycloalkenylene, or arylene optionally substituted with one or more halogens;
    R$_4$ represents aryl optionally substituted with one or more halogens; and
D is H, C$_{1-6}$-alkyl or C$_{3-6}$-cycloalkyl; and
E is H, C$_{1-6}$-alkyl or C$_{3-6}$-cycloalkyl; and
L and M are independently —O— or —S—; and
T is C$_{3-9}$ divalent unsaturated carbon chain optionally substituted with one or more substituents selected from
  halogen or hydroxy; or
  aryl, aralkoxy or C$_{1-3}$-alkoxy which is optionally substituted with halogen; and
U is C$_{3-9}$ divalent unsaturated carbon chain optionally substituted with one or more substituents selected from
  halogen or hydroxy; or
  aryl, aralkoxy or C$_{1-3}$-alkoxy which is optionally substituted with halogen; and
X is arylene or heteroarylene each of which is optionally substituted with one or more substituents selected from
  halogen or hydroxy; or
  C$_{1-6}$-alkyl, C$_{3-6}$-cycloalkyl, C$_{1-6}$-alkoxy, C$_{3-6}$-cycloalkoxy, C$_{1-6}$-alkylthio, C$_{3-6}$-cycloalkylthio each of which is optionally substituted with one or more halogen; or
Y is arylene or heteroarylene each of which is optionally substituted with one or more substituents selected from
  halogen or hydroxy; or
  C$_{1-6}$-alkyl, C$_{3-6}$-cycloalkyl, C$_{1-6}$-alkoxy, C$_{3-6}$-cycloalkoxy, C$_{1-6}$-alkylthio, C$_{3-6}$-cycloalkylthio each of which is optionally substituted with one or more halogen; or
Z is arylene, heteroarylene or a divalent polycyclic ringsystem each of which is optionally substituted with one or more substituents selected from
  halogen, oxo or hydroxy; or
  C$_{1-6}$-alkyl, C$_{3-6}$-cycloalkyl, C$_{1-6}$-alkoxy, C$_{3-6}$-cycloalkoxy, C$_{1-6}$-alkylthio, C$_{3-6}$-cycloalkylthio each of which is optionally substituted with one or more halogen; or a pharmaceutically acceptable salt thereof, or a pharmaceutically acceptable solvate thereof, or any tautomeric forms, stereoisomers, mixture of stereoisomers including a racemic mixture, or polymorphs.

In one embodiment, the present invention is concerned with compounds of formula (I) wherein A is C$_{1-3}$-alkylene which is optionally substituted with one or more substituents selected from
  methyl, C$_{1-3}$-alkoxy, C$_{3-6}$-cycloalkoxy or benzyloxy each of which is optionally substituted with halogen; or
  NR$_1$R$_2$ wherein R$_1$ represents hydrogen and R$_2$ represents —R$_3$—(C=O)—R$_4$ wherein:
    R$_3$ represents C$_{1-6}$-alkylene, C$_{2-6}$-alkenylene, C$_{4-6}$-cycloalkylene, C$_{4-6}$-cycloalkenylene, or phenylene optionally substituted with one or more halogens;
    R$_4$ represents phenyl optionally substituted with one or more halogens.

In another embodiment, the present invention is concerned with compounds of formula (I) wherein A is methylene or ethylene each of which is optionally substituted with one or more substituents selected from
  methoxy or ethoxy; or
  NR$_1$R$_2$ wherein R$_1$ represents hydrogen and R$_2$ represents —R$_3$—(C=O)—R$_4$ wherein R$_3$ and R$_4$ represents phenyl.

In another embodiment, the present invention is concerned with compounds of formula (I) wherein A is ethylene which is optionally substituted with ethoxy.

In another embodiment, the present invention is concerned with compounds of formula (I) wherein A is —O—A' or —S—A' wherein —O— or —S— is linked to X in formula (I) and wherein A' is C$_{1-3}$-alkylene which is optionally substituted with one or more substituents selected from
  halogen or
  C$_{1-3}$-alkyl, C$_{1-6}$-alkoxy, C$_{3-6}$-cycloalkoxy or aralkoxy each of which is optionally substituted with halogen.

In another embodiment, the present invention is concerned with compounds of formula (I) wherein A is —O—A' or —S—A' wherein —O— or —S— is linked to X in formula (I) and wherein A' is methylene or ethylene each of which is optionally substituted with one or more substituents selected from methyl, methoxy or ethoxy.

In another embodiment, the present invention is concerned with compounds of formula (I) wherein B is C$_{1-3}$-alkylene, which is optionally substituted with one or more substituents selected from
  methyl, C$_{1-3}$-alkoxy, C$_{3-6}$-cycloalkoxy or benzyloxy each of which is optionally substituted with halogen; or
  NR$_1$R$_2$ wherein R$_1$ represents hydrogen and R$_2$ represents —R$_3$—(C=O)—R$_4$ wherein:
    R$_3$ represents C$_{1-6}$-alkylene, C$_{2-6}$-alkenylene, C$_{4-6}$-cycloalkylene, C$_{4-6}$-cycloalkenylene, or phenylene optionally substituted with one or more halogens;
    R$_4$ represents phenyl optionally substituted with one or more halogens.

In another embodiment, the present invention is concerned with compounds of formula (I) wherein B is methylene or ethylene each of which is optionally substituted with one or more substituents selected from
  methoxy or ethoxy; or
  NR$_1$R$_2$ wherein R$_1$ represents hydrogen and R$_2$ represents —R$_3$—(C=O)—R$_4$ wherein R$_3$ and R$_4$ represents phenyl.

In another embodiment, the present invention is concerned with compounds of formula (I) wherein B is ethylene which is optionally substituted with ethoxy.

In another embodiment, the present invention is concerned with compounds of formula (I) wherein B is —O—B' or —S—B' wherein —O— or —S— is linked to Y in formula (I) and wherein B' is C$_{1-3}$-alkylene which is optionally substituted with one or more substituents selected from
  halogen or
  C$_{1-3}$-alkyl, C$_{1-6}$-alkoxy, C$_{3-6}$-cycloalkoxy or aralkoxy each of which is optionally substituted with halogen.

In another embodiment, the present invention is concerned with compounds of formula (I) wherein B is —O—B' or —S—B' wherein —O— or —S— is linked to Y in formula (I) and wherein B' is methylene or ethylene each of which is optionally substituted with one or more substituents selected from methyl, methoxy or ethoxy.

In another embodiment, the present invention is concerned with compounds of formula (I) wherein D is H.

In another embodiment, the present invention is concerned with compounds of formula (I) wherein D is methyl or ethyl.

In another embodiment, the present invention is concerned with compounds of formula (I) wherein E is H.

In another embodiment, the present invention is concerned with compounds of formula (I) wherein E is methyl or ethyl.

In another embodiment, the present invention is concerned with compounds of formula (I) wherein L is —O—.

In another embodiment, the present invention is concerned with compounds of formula (I) wherein L is —S—.

In another embodiment, the present invention is concerned with compounds of formula (I) wherein M is —O—.

In another embodiment, the present invention is concerned with compounds of formula (I) wherein M is —S—.

In another embodiment, the present invention is concerned with compounds of formula (I) wherein T is $C_{3-9}$ divalent unsaturated carbon chain optionally substituted with one or more substituents selected from phenyl, benzyloxy or $C_{1-3}$-alkoxy which is optionally substituted with halogen.

In another embodiment, the present invention is concerned with compounds of formula (I) wherein T is an unsubstituted $C_{3-9}$ divalent unsaturated carbon chain.

In another embodiment, the present invention is concerned with compounds of formula (I) wherein T is $C_{3-9}$ alkenylene.

In another embodiment, the present invention is concerned with compounds of formula (I) wherein T is $C_{3-9}$ alkynylene.

In another embodiment, the present invention is concerned with compounds of formula (I) wherein T is $C_{5-9}$ alkenynylene.

In another embodiment, the present invention is concerned with compounds of formula (I) wherein U is $C_{3-9}$ divalent unsaturated carbon chain optionally substituted with one or more substituents selected from phenyl, benzyloxy or $C_{1-3}$-alkoxy which is optionally substituted with halogen.

In another embodiment, the present invention is concerned with compounds of formula (I) wherein U is an unsubstituted $C_{3-9}$ divalent unsaturated carbon chain.

In another embodiment, the present invention is concerned with compounds of formula (I) wherein U is $C_{3-9}$ alkenylene.

In another embodiment, the present invention is concerned with compounds of formula (1) wherein U is $C_{3-9}$ alkynylene.

In another embodiment, the present invention is concerned with compounds of formula (I) wherein U is $C_{5-9}$ alkenynylene.

In another embodiment, the present invention is concerned with compounds of formula (I) wherein X is arylene or heteroarylene each of which is optionally substituted with one or more substituents selected from
  halogen or
  $C_{1-6}$-alkyl optionally substituted with one or more halogen.

In another embodiment, the present invention is concerned with compounds of formula (I) wherein X is arylene optionally substituted with one or more substituents selected from
  halogen or
  $C_{1-6}$-alkyl optionally substituted with one or more halogen.

In another embodiment, the present invention is concerned with compounds of formula (I) wherein X is phenylene optionally substituted with one or more substituents selected from
  halogen or
  $C_{1-3}$-alkyl optionally substituted with one or more halogen.

In another embodiment, the present invention is concerned with compounds of formula (I) wherein X is phenylene optionally substituted with one or more halogen.

In another embodiment, the present invention is concerned with compounds of formula (I) wherein Y is arylene or heteroarylene each of which is optionally substituted with one or more substituents selected from
  halogen or
  $C_{1-6}$-alkyl optionally substituted with one or more halogen.

In another embodiment, the present invention is concerned with compounds of formula (I) wherein Y is arylene optionally substituted with one or more substituents selected from
  halogen or
  $C_{1-6}$-alkyl optionally substituted with one or more halogen.

In another embodiment, the present invention is concerned with compounds of formula (I) wherein Y is phenylene optionally substituted with one or more substituents selected from
  halogen or
  $C_{1-3}$-alkyl optionally substituted with one or more halogen.

In another embodiment, the present invention is concerned with compounds of formula (I) wherein Y is phenylene optionally substituted with one or more halogen.

In another embodiment, the present invention is concerned with compounds of formula (I) wherein Z is arylene, heteroarylene or a divalent polycyclic ringsystem each of which is optionally substituted with one or more substituents selected from
  halogen, oxo or
  $C_{1-6}$-alkyl, $C_{1-6}$-alkoxy each of which is optionally substituted with one or more halogen.

In another embodiment, the present invention is concerned with compounds of formula (I) wherein Z is selected among the following groups:

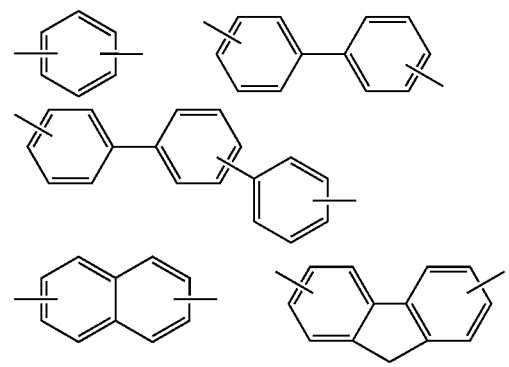

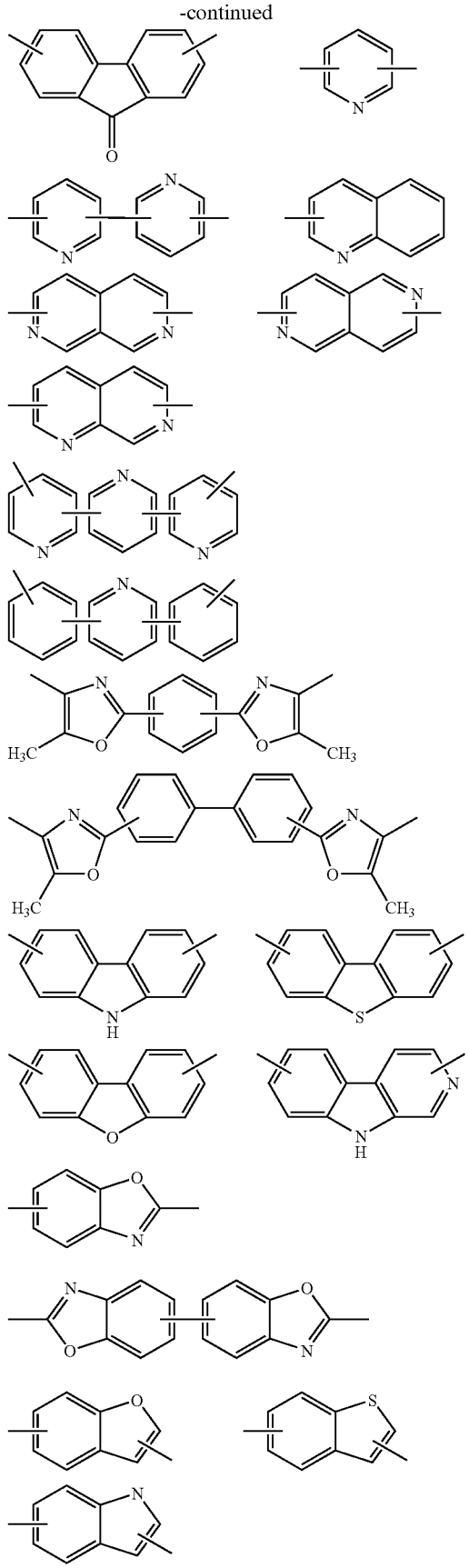

which is optionally substituted with one or more substituents selected from
halogen or
C$_{1-6}$-alkyl or C$_{1-6}$-alkoxy each of which is optionally substituted with one or more halogen.

In another embodiment, the present invention is concerned with compounds of formula (I) wherein Z is selected among the following groups:

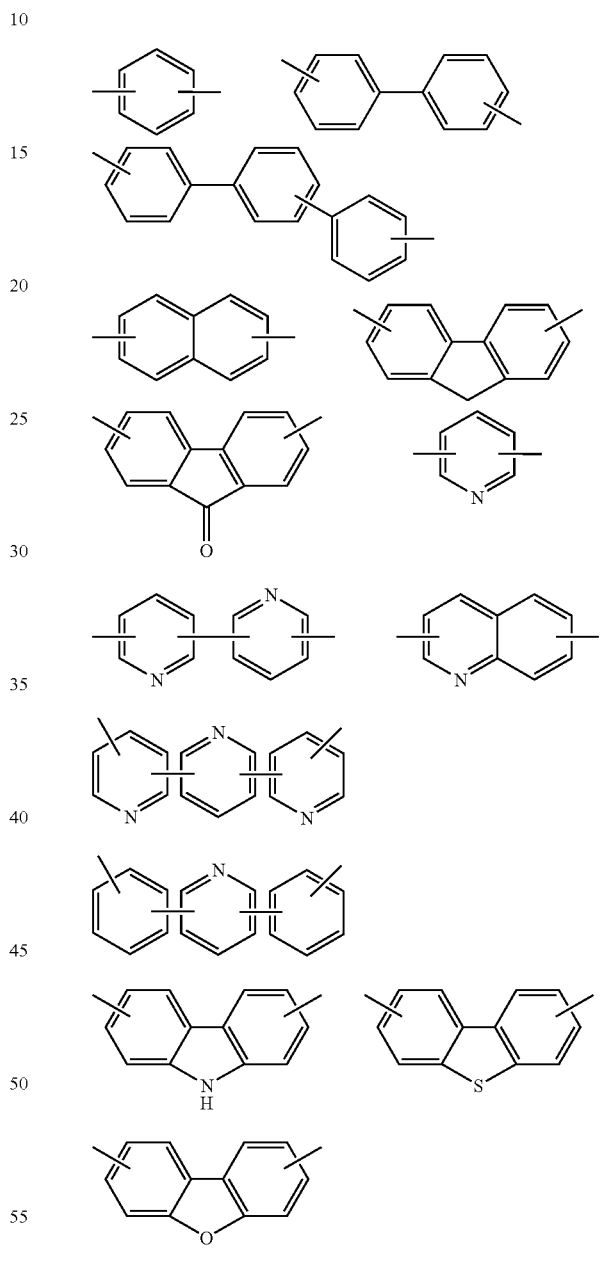

In another embodiment, the present invention is concerned with compounds of formula (I) wherein Z is selected among the following groups:

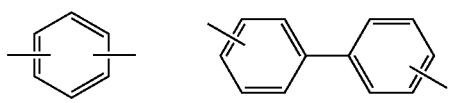

-continued

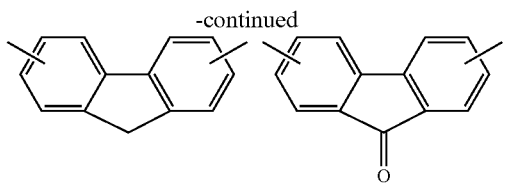

In another embodiment, the present invention is concerned with compounds of general formula(I) as described by general formula (II)

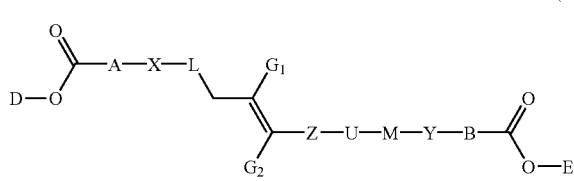

wherein D, A, X, L, Z, U, M, Y, B and E are as defined for formula (I) or in any of the above preferred embodiments; and $G_1$ is H, $C_{1-3}$-alkyl, $C_{1-3}$-alkoxy or $C_{1-3}$-aralkoxy each of which is optionally substituted with halogen; and $G_2$ is H, $C_{1-3}$-alkyl, $C_{2-6}$-alkenyl, $C_{2-6}$-alkynyl, $C_{3-6}$-alkenynyl, aryl, aralkyl, $C_{1-3}$-aralkoxy each of which is optionally substituted with halogen; or a pharmaceutically acceptable salt thereof, or a pharmaceutically acceptable solvate thereof, or any tautomeric forms, stereoisomers, mixture of stereoisomers including a racemic mixture, or polymorphs.

In another embodiment, the present invention is concerned with compounds of formula (II) wherein D, A, X, L, Z, U, M, Y, B and E are as defined for formula (I) or in any of the above preferred embodiments; and $G_1$ is H, $C_{1-3}$-alkyl or $C_{1-3}$-alkoxy each of which is optionally substituted with halogen; and $G_2$ is H, $C_{1-3}$-alkyl or aryl each of which is optionally substituted with halogen.

In another embodiment, the present invention is concerned with compounds of formula (II) wherein D, A, X, L, Z, U, M, Y, B and E are as defined for formula (I) or in any of the above preferred embodiments; and $G_1$ is H; and $G_2$ is H or methyl.

In another embodiment, the present invention is concerned with compounds of general formula (I) as described by general formula (III)

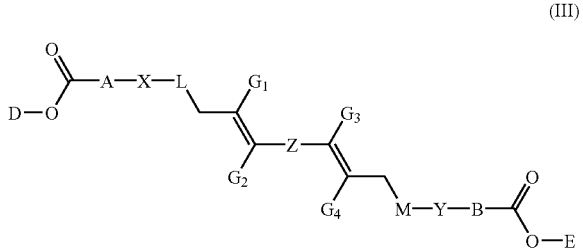

wherein D, A, X, L, Z, M, Y, B and E are as defined for formula (I) or in any of the above preferred embodiments; and $G_1$ and $G_4$ independently of each other are H, $C_{1-3}$-alkyl, $C_{1-3}$-alkoxy or $C_{1-3}$-aralkoxy each of which is optionally substituted with halogen; and $G_2$ and $G_3$ independently of each other is H, $C_{1-3}$-alkyl, $C_{2-6}$-alkenyl, $C_{2-6}$-alkynyl, $C_{3-6}$-alkenynyl, aryl, aralkyl, $C_{1-3}$-alkoxy or $C_{1-3}$-aralkoxy each of which is optionally substituted with halogen; or a pharmaceutically acceptable salt thereof, or a pharmaceutically acceptable solvate thereof, or any tautomeric forms, stereoisomers, mixture of stereoisomers including a racemic mixture or polymorphs.

In another embodiment, the present invention is concerned with compounds of formula (III) wherein D, A, X, L, Z, M, Y, B and E are as defined for formula (I) or in any of the above preferred embodiments; and $G_1$ and $G_4$ independently of each other are H, $C_{1-3}$-alkyl or $C_{1-3}$-alkoxy each of which is optionally substituted with halogen; and $G_2$ and $G_3$ independently of each other are is H, $C_{1-3}$-alkyl or aryl each of which is optionally substituted with halogen.

In another embodiment, the present invention is concerned with compounds of formula (III) wherein D, A, X, L, Z, M, Y, B and E are as defined for formula (I) or in any of the above preferred embodiments; and $G_1$ and $G_4$ are H; and $G_2$ and $G_3$ independently of each other are H or methyl.

In another embodiment, the present invention is concerned with compounds of general formula (I) as described by general formula (IV)

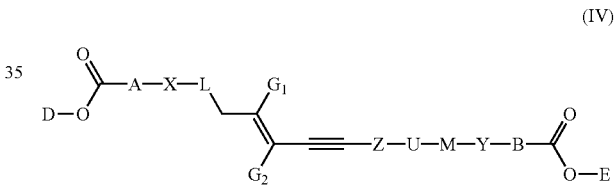

wherein D, A, X, L, Z, U, M, Y, B and E are as defined for formula (I) or in any of the above preferred embodiments; and $G_1$ is H, $C_{1-3}$-alkyl, $C_{1-3}$-alkoxy or $C_{1-3}$-aralkoxy each of which is optionally substituted with halogen; and $G_2$ is H, $C_{1-3}$-alkyl, $C_{2-6}$-alkenyl, $C_{2-6}$-alkynyl, $C_{3-6}$-alkenynyl, aryl, aralkyl, $C_{1-3}$-aralkoxy each of which is optionally substituted with halogen; or a pharmaceutically acceptable salt thereof, or a pharmaceutically acceptable solvate thereof, or any tautomeric forms, stereoisomers, mixture of stereoisomers including a racemic mixture or polymorphs.

In another embodiment, the present invention is concerned with compounds of formula (IV) wherein D, A, X, L, Z, U, M, Y, B and E are as defined for formula (I) or in any of the above preferred embodiments; and $G_1$ is H, $C_{1-3}$-alkyl or $C_{1-3}$-alkoxy each of which is optionally substituted with halogen; and $G_2$ is H, $C_{1-3}$-alkyl or aryl each of which is optionally substituted with halogen.

In another embodiment, the present invention is concerned with compounds of formula (IV) wherein D, A, X, L, Z, U, M, Y, B and E are as defined for formula (I) or in any of the above preferred embodiments; and $G_1$ is H; and $G_2$ is H or methyl.

In another embodiment, the present invention is concerned with compounds of general formula (I) as described by general formula (V)

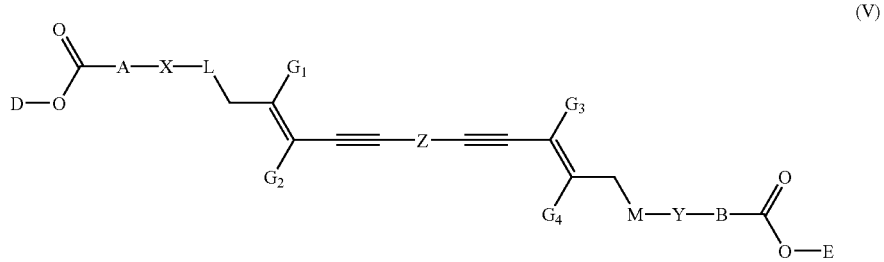

(V)

wherein D, A, X, L, Z, M, Y, B and E are as defined for formula (I) or in any of the above preferred embodiments; and $G_1$ and $G_4$ independently of each other are H, $C_{1-3}$-alkyl, $C_{1-3}$-alkoxy or $C_{1-3}$-aralkoxy each of which is optionally substituted with halogen; and $G_2$ and $G_3$ independently of each other is H, $C_{1-3}$-alkyl, $C_{2-6}$-alkenyl, $C_{2-6}$-alkynyl, $C_{3-6}$-alkenynyl, aryl, aralkyl, $C_{1-3}$-alkoxy or $C_{1-3}$-aralkoxy each of which is optionally substituted with halogen; or a pharmaceutically acceptable salt thereof, or a pharmaceutically acceptable solvate thereof, or any tautomeric forms, stereoisomers, mixture of stereoisomers including a racemic mixture or polymorphs.

In another embodiment, the present invention is concerned with compounds of formula (V) wherein D, A, X, L, Z, M, Y, B and E are as defined for formula (I) or in any of the above preferred embodiments; and $G_1$ and $G_4$ independently of each other are H, $C_{1-3}$-alkyl or $C_{1-3}$-alkoxy each of which is optionally substituted with halogen; and $G_2$ and $G_3$ independently of each other are H, $C_{1-3}$-alkyl or aryl each of which is optionally substituted with halogen.

In another embodiment, the present invention is concerned with compounds of formula (V) wherein D, A, X, L, Z, M, Y, B and E are as defined for formula (I) or in any of the above preferred embodiments; and $G_1$ and $G_4$ are H; and $G_2$ and $G_3$ independently of each other are H or methyl.

In another embodiment, the present invention is concerned with compounds of the present invention having a trans-configuration when possible.

In another embodiment, the present invention is concerned with compounds of the present invention having a (S)-configuration when possible.

In another embodiment, the present invention is concerned with compounds of the present invention having a cis-configuration when possible.

In another embodiment, the present invention is concerned with compounds of the present invention which is a mixed PPARα/PPARγ profile.

In another embodiment, the present invention is concerned with compounds of the present invention which is a mixed PPARα/PPARδ profile.

In another embodiment, the present invention is concerned with compounds of the present invention which is a mixed PPARγ/PPARδ profile.

In another embodiment, the present invention is concerned with compounds of the present invention which is a mixed PPARα/PPARγ/PPARδ profile.

In another embodiment, the present invention is concerned with compounds of the present invention, which is a selective PPARα profile.

In another embodiment, the present invention is concerned with compounds of the present invention, which is a selective PPARγ profile.

In another embodiment, the present invention is concerned with compounds of the present invention, which is a selective PPARδ profile.

Examples of specific compounds of the invention are:

2-Ethoxy-3-{4-[5-(4-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester;

3-{4-[5-(4-{5-[4-(2-Carboxy-2-ethoxy-ethyl)-phenoxy]-pent-3-en-1-ynyl}-phenyl)-pent-2-en-4-ynyloxy]-phenyl}-2-ethoxy-propionic acid;

3-Chloro-4-(5-{4-[5-(3-Chloro-4-ethoxycarbonylmethyl-phenoxy)-pent-3-en-1-ynyl]-phenyl}-pent-2-en-4-ynyloxy)-phenyl]-acetic acid ethyl ester;

[4-(5-{4-[5-(4-Carboxymethyl-3-chloro-phenoxy)-pent-3-en-1-ynyl]-phenyl}-pent-2-en-4-ynyloxy)-3-chloro-phenyl]-acetic acid;

2-Ethoxy-3-{4-[5-(3-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester;

3-{4-[5-(3-{5-[4-(2-Carboxy-2-ethoxy-ethyl)-phenoxy]-pent-3-en-1-ynyl}-phenyl)-pent-2-en-4-ynyloxy]-phenyl}-2-ethoxy-propionic acid;

[3-Chloro-4-(5-{3-[5-(2-chloro-4-ethoxycarbonylmethyl-phenoxy)-pent-3-en-1-ynyl]-phenyl}-pent-2-en-4-ynyloxy)-phenyl]-acetic acid ethyl ester;

[4-(5-{3-[5-(4-Carboxymethyl-2-chloro-phenoxy)-pent-3-en-1-ynyl]-phenyl}-pent-2-en-4-ynyloxy)-3-chloro-phenyl]-acetic acid;

2-(2-Benzoyl-phenylamino)-3-(4-{5-[4-(5-{4-[2-(2-benzoyl-phenylamino)-2-methoxycarbonyl-ethyl]-phenoxy}-pent-3-en-1-ynyl)-phenyl]-pent-2-en-4-ynyloxy}-phenyl)-propionic acid methyl ester;

2-(2-Benzoyl-phenylamino)-3-(4-{5-[4-(5-{4-[2-(2-benzoyl-phenylamino)-2-carboxy-ethyl]-phenoxy}-pent-3-en-1-ynyl)-phenyl]-pent-2-en-4-ynyloxy}-phenyl)-propionic acid;

2-Ethoxy-3-{4-[3-(4'-{3-[4-(2-ethoxy-2-ethoxycarbonyl-ethyl)-phenoxy]-1-methyl-propenyl}-biphenyl-4-yl)-but-2-enyloxy]-phenyl}-propionic acid ethyl ester;

3-{4-[3-(4'-{3-[4-(2-Carboxy-2-ethoxy-ethyl)-phenoxy]-1-methyl-propenyl}-biphenyl-4-yl)-but-2-enyloxy]-phenyl}-2-ethoxy-propionic acid;

2-Ethoxy-3-{4-[5-(7-{5-[4-(2-ethoxy-2-ethoxycarbonyl-ethyl)-phenoxy]-3-methyl-pent-3-en-1-ynyl}-9-oxo-9H-fluoren-2-yl)-3-methyl-pent-2-en-4-ynyloxy]-phenyl}-propionic acid ethyl ester;

3-{4-[5-(7-{5-[4-(2-carboxy-2-ethoxy-ethyl)-phenoxy]-3-methyl-pent-3-en-1-ynyl}-9-oxo-9H-fluoren-2-yl)-3-methyl-pent-2-en-4-ynyloxy]-phenyl}-2-ethoxy-propionic acid;

[4-(3-{3-[3-(4-Methoxycarbonylmethyl-phenoxy)-prop-1-ynyl]-phenyl}-prop-2-ynyloxy)-phenyl]-acetic acid methyl ester;

[4-(3-{3-[3-(4-Methoxycarbonylmethyl-phenoxy)-prop-1-ynyl]-phenyl}-prop-2-ynyloxy)-phenyl]-acetic acid;

[4-(5-{4-[5-(4-Methoxycarbonylmethoxy-3-methyl-phenoxy)-pent-3-en-1-ynyl]-phenyl}-pent-2-en-4-ynyloxy)-2-methyl-phenoxy]-acetic acid methyl ester;

[4-(5-{4-[5-(4-Methoxycarbonylmethoxy-3-methyl-phenoxy)-pent-3-en-1-ynyl]-phenyl}-pent-2-en-4-ynyloxy)-2-methyl-phenoxy]-acetic acid;

3-{3-Bromo-4-[5-(4-{5-[2-bromo-4-(2-ethoxy-2-ethoxycarbonyl-ethyl)-phenoxyl-pent-3-en-1-ynyl}-phenyl)-pent-2-en-4-ynyloxy]-phenyl}-2-ethoxy-propionic acid ethyl ester;

3-{3-Bromo-4-{5-(4-(5-[2-bromo-4-(2-ethoxy-2-ethoxycarbonyl-ethyl)-phenoxyl]-pent-3-en-1-ynyl}-phenyl)-pent-2-en-4-ynyloxy]-phenyl}-2-ethoxy-propionic acid;

[3-(5-{4-[5-(3-Ethoxycarbonylmethyl-phenoxy)-pent-3-en-1-ynyl]-phenyl}-pent-2-en-4-ynyloxy)-phenyl]-acetic acid ethyl ester;

[3-(5-{4-[5-(3-Ethoxycarbonylmethyl-phenoxy)-pent-3-en-1-ynyl]-phenyl}-pent-2-en-4-ynyloxy)-phenyl]-acetic acid;

2-Ethoxy-3-{4-[5-(4'-{5-[4-(2-ethoxy-2-ethoxycarbonyl-ethyl)-phenoxy]-3-methyl-pent-3-en-1-ynyl}-biphenyl-4-yl)-3-methyl-pent-2-en-4-ynyloxy]-phenyl}-propionic acid ethyl ester;

2-Ethoxy-3-{4-[5-(4'-{5-[4-(2-ethoxy-2-ethoxycarbonyl-ethyl)-phenoxy]-3-methyl-pent-3-en-1-ynyl}-biphenyl-4-yl)-3-methyl-pent-2-en-4-ynyloxy]-phenyl}-propionic acid;

2-Ethoxy-3-{4-[5-(4-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid ethyl ester;

2-Ethoxy-3-{4-[5-(4-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid;

2-Ethoxy-3-{4-[5-(3-(5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid ethyl ester;

2-Ethoxy-3-(4-[5-(3-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl]-propionic acid;

[4-(3-{7-[3-(4-Methoxycarbonylmethoxy-3-methyl-phenylsulfanyl)-propenyl}-9H-fluoren-2-yl)-allylsulfanyl]-2-methyl-phenoxyl-acetic acid methyl ester; or a salt thereof with a pharmaceutically acceptable acid or base, or any optical isomer or mixture of optical isomers, including a racemic mixture, or any tautomeric forms.

Other examples of specific compounds of the invention are:

(4-(3-(4'-(3-(4-Carboxymethoxy-3-methyl-phenylsulfanyl)-propenyl)-biphenyl-4-yl)-allylsulfanyl)-2-methyl-phenoxy)-acetic acid;

3-(4-(3-(4'-(3-(4-(2-Carboxy-2-ethoxy-ethyl)-phenylsulfanyl)-propenyl)-biphenyl-4-yl)-allylsulfanyl)-phenyl)-2-ethoxy-propionic acid;

3-(4-(3-(4'-(3-(4-(2-Carboxy-2-ethoxy-ethyl)-phenoxy)-propenyl)-biphenyl-4-yl)-allyloxy)-phenyl)-2-ethoxy-propionic acid;

3-(4-(3-(4'-(3-(4-Carboxymethoxy-3-methyl-phenylsulfanyl)-propenyl)-biphenyl-4-yl)-allyloxy)-phenyl)-2-ethoxy-propionic acid;

3-(4-(3-(4'-(3-(4-Carboxymethoxy-3-methyl-phenylsulfanyl)-propenyl)-biphenyl-4-yl)-allylsulfanyl)-phenyl)-2-ethoxy-propionic acid;

(4-(3-(4'-(3-(4-Carboxymethoxy-2-chloro-phenoxy)-propenyl)-biphenyl-4-yl)-allylsulfanyl)-2-methyl-phenoxy)-acetic acid;

(4-(3-(4'-(3-(4-Carboxymethoxy-2-chloro-phenoxy)-propenyl)-biphenyl-4-yl)-allyloxy)-3-chloro-phenyl)-acetic acid;

3-(4-(3-(4'-(3-(4-Carboxymethoxy-2-chloro-phenoxy)-propenyl)-biphenyl-4-yl)-allyloxy)-phenyl)-2-ethoxy-propionic acid;

3-(4-(3-(4'-(3-(4-Carboxymethoxy-2-chloro-phenoxy)-propenyl)-biphenyl-4-yl)-allylsulfanyl)-phenyl)-2-ethoxy-propionic acid;

(4-(3-(7-(3-(4-Carboxymethoxy-3-methyl-phenylsulfanyl)-propenyl)-9H-fluoren-2-yl)-allylsulfanyl)-2-methyl-phenoxy)-acetic acid;

3-(4-(3-(7-(3-(4-carboxymethoxy-3-methyl-phenylsulfanyl)-propenyl)-9H-fluoren-2-yl)-allylsulfanyl)-phenyl)-2-ethoxy-propionic acid;

3-(4-(3-(7-(3-(4-carboxymethoxy-3-methyl-phenylsulfanyl)-propenyl)-9H-fluoren-2-yl)-allyloxy)-phenyl)-2-ethoxy-propionic acid;

(4-(3-(7-(3-(4-Carboxymethoxy-3-methyl-phenylsulfanyl)-propenyl)-9H-fluoren-2-yl)-allyloxy)-3-chloro-phenyl)-acetic acid;

3-(4-(3-(7-(3-(4-carboxymethoxy-2-chloro-phenoxy)-propenyl)-9H-fluoren-2-yl)-allylsulfanyl)-phenyl)-2-ethoxy-propionic acid;

3-(4-(3-(7-(3-(4-carboxymethoxy-2-chloro-phenoxy)-propenyl)-9H-fluoren-2-yl)-allyloxy)-phenyl)-2-ethoxy-propionic acid;

3-(4-(3-(7-(3-(4-(2-Carboxy-2-ethoxy-ethyl)-phenoxy)-propenyl)-9H-fluoren-2-yl)-allyloxy)-phenyl)-2-ethoxy-propionic acid;

3-(4-(3-(7-(3-(4-(2-Carboxy-2-ethoxy-ethyl)-phenylsulfanyl)-propenyl)-9H-fluoren-2-yl)-allylsulfanyl)-phenyl)-2-ethoxy-propionic acid;

(4-(3-(7-(3-(4-Carboxymethoxy-2-chloro-phenyxy)-propenyl)-9H-fluoren-2-yl)-allyloxy)-3-chloro-phenyl)-acetic acid;

3-(-4-(3-(4'-(3-(4-(2-Carboxy-2-ethoxy-ethyl)-phenoxy)-1-methyl-propenyl)-biphenyl-4-yl)-but-2-enyloxy)-phenyl)-2-ethoxy-propionic acid;

3-(-4-(3-(4'-(3-(4-(2-Carboxy-2-ethoxy-ethyl)-phenylsulfanyl)-1-methyl-propenyl)-biphenyl-4-yl)-but-2-enylsulfanyl)-phenyl)-2-ethoxy-propionic acid;

(4-(3-(4'-(3-(4-Carboxymethyl-2-chloro-phenoxy)-1-methyl-propenyl)-biphenyl-4-yl)-but-2-enyloxy)-3-chloro-phenyl)-acetic acid;

(4-(3-(4'-(3-(4-Carboxymethyl-3-methyl-phenylsulfanyl)-1-methyl-propenyl)-biphenyl-4-yl)-but-2-enylsulfanyl)-2-methyl-phenoxy)-acetic acid;

3-(-4-(3-(4'-(3-(4-Carboxymethoxy-3-methyl-phenylsulfanyl)-1-methyl-propenyl)-biphenyl-4-yl)-but-2-enylsulfanyl)-phenyl)-2-ethoxy-propionic acid;

3-(-4-(3-(4'-(3-(4-Carboxymethoxy-3-methyl-phenylsulfanyl)-1-methyl-propenyl)-biphenyl-4-yl)-but-2-enyloxy)-phenyl)-2-ethoxy-propionic acid;

3-(-4-(3-(4'-(3-(4-(2-Carboxy-2-ethoxy-ethyl)-phenylsulfanyl)-1-methyl-propenyl)-biphenyl-4-yl)-but-2-enyloxy)-phenyl)-2-ethoxy-propionic acid;

3-(4-(5-(4-(5-(4-(2-Carboxy-2-ethoxy-ethyl)-phenoxy)-pent-3-en-1-ynyl)-phenyl)-pent-2-en-4-ynyloxy)-phenyl)-2-ethoxy-propionic acid;

3-(4-(5-(4-(5-(4-(2-Carboxy-2-ethoxy-ethyl)-phenylsulfanyl)-pent-3-en-1-ynyl)-phenyl)-pent-2-en-4-ynylsulfanyl)-phenyl)-2-ethoxy-propionic acid;

4-(5-(4-(5-(4-Carboxymethyl-2-chloro-phenoxy)-pent-3-en-1-ynyl)-phenyl)-pent-2-en-4-ynyloxy)-3-chloro-phenyl)-acetic acid;

4-(5-(4-(5-(4-Carboxymethyl-3-methyl-phenylsulfanyl)-pent-3-en-1-ynyl)-phenyl)-pent-2-en-4-ynylsulfanyl)-2-methyl-phenoxy)-acetic acid;

3-(4-(5-(4-(5-(4-Carboxymethoxy-3-methyl-phenylsulfanyl)-pent-3-en-1-ynyl)-phenyl)-pent-2-en-4-ynylsulfanyl)-phenyl)-2-ethoxy-propionic acid;

3-(4-(5-(4-(5-(4-Carboxymethoxy-3-methyl-phenylsulfanyl)-pent-3-en-1-ynyl)-phenyl)-pent-2-en-4-ynyloxy)-phenyl)-2-ethoxy-propionic acid;

3-(4-(5-(4'-(5-(4-(2-Carboxy-2-ethoxy-ethyl)-phenoxy)-pent-3-en-1-ynyl)-biphenyl-4-yl)-pent-2-en-4-ynyloxy)-phenyl)-2-ethoxy-propionic acid;

3-(4-(5-(4'-(5-(4-(2-Carboxy-2-ethoxy-ethyl)-phenylsulfanyl)-pent-3-en-1-ynyl)-biphenyl-4-yl)-pent-2-en-4-ynylsulfanyl)-phenyl)-2-ethoxy-propionic acid;

4-(5-(4'-(5-(4-Carboxymethyl-2-chloro-phenoxy)-pent-3-en-1-ynyl)-biphenyl-4-yl)-pent-2-en-4-ynyloxy)-3-chloro-phenyl)-acetic acid;

4-(5-(4'-(5-(4-Carboxymethyl-3-methyl-phenylsulfanyl)-pent-3-en-1-ynyl)-biphenyl-4-yl)-pent-2-en-4-ynylsulfanyl)-2-methyl-phenoxy)-acetic acid;

3-(4-(5-(4'-(5-(4-Carboxymethoxy-3-methyl-phenylsulfanyl)-pent-3-en-1-ynyl)-biphenyl-4-yl)-pent-2-en-4-ynylsulfanyl)-phenyl)-2-ethoxy-propionic acid;

3-(4-(5-(4'-(5-(4-Carboxymethoxy-3-methyl-phenylsulfanyl)-pent-3-en-1-ynyl)-biphenyl-4-yl)-pent-2-en-4-ynyloxy)-phenyl)-2-ethoxy-propionic acid;

(4-(5-(4'-(5-(4-Carboxymethyl-2-chloro-phenoxy)-3-methyl-pent-3-en-1-ynyl)-biphenyl-4-yl)-3-methyl-pent-2-en-4-ynyloxy)-3-chloro-phenyl)-acetic acid;

(4-(5-(4'-(5-(4-Carboxymethyl-3-methyl-phenylsulfanyl)-3-methyl-pent-3-en-1-ynyl)-biphenyl-4-yl)-3-methyl-pent-2-en-4-ynylsulfanyl)-2-methyl-phenoxy)-acetic acid;

3-(4-(5-(4'-(5-(4-(2-Carboxy-2-ethoxy-ethyl)-phenoxy)-3-methyl-pent-3-en-1-ynyl)-biphenyl-4-yl)-3-methyl-pent-2-en-4-ynyloxy)-phenyl-2-ethoxy-propionic acid;

3-(4-(5-(4'-(5-(4-(2-Carboxy-2-ethoxy-ethyl)-phenylsulfanyl)-3-methyl-pent-3-en-1-ynyl)-biphenyl-4-yl)-3-methyl-pent-2-en-4-ynylsulfanyl)-phenyl-2-ethoxy-propionic acid;

3-(4-(5-(4'-(5-(4-(2-Carboxy-2-ethoxy-ethyl)-phenylsulfanyl)-3-methyl-pent-3-en-1-ynyl)-biphenyl-4-yl)-3-methyl-pent-2-en-4-ynyloxy)-phenyl-2-ethoxy-propionic acid;

3-(4-(5-(4'-(5-(4-Carboxymethoxy-3-methyl-phenylsulfanyl)-3-methyl-pent-3-en-1-ynyl)-biphenyl-4-yl)-3-methyl-pent-2-en-4-ynylsulfanyl)-phenyl-2-ethoxy-propionic acid;

3-(4-(5-(4'-(5-(4-Carboxymethoxy-3-methyl-phenylsulfanyl)-3-methyl-pent-3-en-1-ynyl)-biphenyl-4-yl)-3-methyl-pent-2-en-4-ynyloxyl)-phenyl-2-ethoxy-propionic acid;

(4-(5-(4''-(5-(4-Carboxymethyl-2-chloro-phenoxy)-3-methyl-pent-3-en-1-ynyl)-[1,1';4'1'']terphenyl-4-yl)-3-methyl-pent-2-en-4-ynyloxy)-3-chloro-phenyl)-acetic acid;

(4-(5-(4''-(5-(4-Carboxymethyl-3-methyl-phenylsulfanyl)-3-methyl-pent-3-en-1-ynyl)-[1,1';4'1'']terphenyl-4-yl)-3-methyl-pent-2-en-4-ynylsulfanyl)-2-methyl-phenoxy)-acetic acid;

3-(4-(5-(4''-(5-(4-(2-Carboxy-2-ethoxy-ethyl)-phenoxy)-3-methyl-pent-3-en-1-ynyl)-[1,1';4'1'']terphenyl-4-yl)-3-methyl-pent-2-en-4-ynyloxy)-phenyl-2-ethoxy-propionic acid;

3-(4-(5-(4''-(5-(4-(2-Carboxy-2-ethoxy-ethyl)-phenylsulfanyl)-3-methyl-pent-3-en-1-ynyl)-[1,1';4'1'']terphenyl-4-yl)-3-methyl-pent-2-en-4-ynylsulfanyl)-phenyl-2-ethoxy-propionic acid;

3-(4-(5-(4''-(5-(4-(2-Carboxy-2-ethoxy-ethyl)-phenylsulfanyl)-3-methyl-pent-3-en-1-ynyl)-[1,1';4'1'']terphenyl-4-yl)-3-methyl-pent-2-en-4-ynyloxy)-phenyl-2-ethoxy-propionic acid;

3-(4-(5-(4''-(5-(4-Carboxymethoxy-3-methyl-phenylsulfanyl)-3-methyl-pent-3-en-1-ynyl)-[1,1';4'1'']terphenyl-4-yl)-3-methyl-pent-2-en-4-ynylsulfanyl)-phenyl-2-ethoxy-propionic acid;

3-(4-(5-(4''-(5-(4-Carboxymethoxy-3-methyl-phenylsulfanyl)-3-methyl-pent-3-en-1-ynyl)-[1,1';4'1'']terphenyl-4-yl)-3-methyl-pent-2-en-4-ynyloxyl)-phenyl-2-ethoxy-propionic acid;

3-(4-(5-(4''-(5-(4-(2-Carboxy-2-ethoxy-ethyl)-phenoxy)-pent-3-en-1-ynyl)-[1,1';4'1'']terphenyl-4-yl)-pent-2-en-4-ynyloxy)-phenyl)-2-ethoxy-propionic acid;

3-(4-(5-(4''-(5-(4-(2-Carboxy-2-ethoxy-ethyl)-phenylsulfanyl)-pent-3-en-1-ynyl)-[1,1';4'1'']terphenyl-4-yl)-pent-2-en-4-ynylsulfanyl)-phenyl)-2-ethoxy-propionic acid;

4-(5-(4''-(5-(4-Carboxymethyl-2-chloro-phenoxy)-pent-3-en-1-ynyl)-[1,1';4'1'']terphenyl-4-yl)-pent-2-en-4-ynyloxy)-3-chloro-phenyl)-acetic acid;

4-(5-(4''-(5-(4-Carboxymethyl-3-methyl-phenylsulfanyl)-pent-3-en-1-ynyl)-[1,1';4'1'']terphenyl-4-yl)-pent-2-en-4-ynylsulfanyl)-2-methyl-phenoxy)-acetic acid;

3-(4-(5-(4''-(5-(4-Carboxymethoxy-3-methyl-phenylsulfanyl)-pent-3-en-1-ynyl)-[1,1';4'1'']terphenyl-4-yl)-pent-2-en-4-ynylsulfanyl)-phenyl)-2-ethoxy-propionic acid;

3-(4-(5-(4''-(5-(4-Carboxymethoxy-3-methyl-phenylsulfanyl)-pent-3-en-1-ynyl)-[1,1';4'1'']terphenyl-4-yl)-pent-2-en-4-ynyloxy)-phenyl)-2-ethoxy-propionic acid;

(4-(5-(4-(5-(4-Carboxymethyl-2-chloro-phenoxy)-3-methyl-pent-3-en-1-ynyl)-phenyl)-3-methyl-pent-2-en-4-ynyloxy)-3-chloro-phenyl)-acetic acid;

(4-(5-(4-(5-(4-Carboxymethyl-3-methyl-phenylsulfanyl)-3-methyl-pent-3-en-1-ynyl)-phenyl)-3-methyl-pent-2-en-4-ynylsulfanyl)-2-methyl-phenoxy)-acetic acid;

3-(4-(5-(4-(5-(4-(2-Carboxy-2-ethoxy-ethyl)-phenoxy)-3-methyl-pent-3-en-1-ynyl)-phenyl)-3-methyl-pent-2-en-4-ynyloxy)-phenyl-2-ethoxy-propionic acid;

3-(4-(5-(4-(5-(4-(2-Carboxy-2-ethoxy-ethyl)-phenylsulfanyl)-3-methyl-pent-3-en-1-ynyl)-phenyl)-3-methyl-pent-2-en-4-ynylsulfanyl)-phenyl-2-ethoxy-propionic acid;

3-(4-(5-(4-(5-(4-(2-Carboxy-2-ethoxy-ethyl)-phenylsulfanyl)-3-methyl-pent-3-en-1-ynyl)-phenyl)-3-methyl-pent-2-en-4-ynyloxy)-phenyl-2-ethoxy-propionic acid;

3-(4-(5-(4-(5-(4-Carboxymethoxy-3-methyl-phenylsulfanyl)-3-methyl-pent-3-en-1-ynyl)-phenyl)-3-methyl-pent-2-en-4-ynylsulfanyl)-phenyl-2-ethoxy-propionic acid;

3-(4-(5-(4-(5-(4-Carboxymethoxy-3-methyl-phenylsulfanyl)-3-methyl-pent-3-en-1-ynyl)-phenyl)-3-methyl-pent-2-en-4-ynyloxyl)-phenyl-2-ethoxy-propionic acid;

3-(4-(5-(3-(5-(4-(2-Carboxy-2-ethoxy-ethyl)-phenoxy)-pent-3-en-1-ynyl)-phenyl)-pent-2-en-4-ynyloxy)-phenyl)-2-ethoxy-propionic acid;

3-(4-(5-(3-(5-(4-(2-Carboxy-2-ethoxy-ethyl)-phenylsulfanyl)-pent-3-en-1-ynyl)-phenyl)-pent-2-en-4-ynylsulfanyl)-phenyl)-2-ethoxy-propionic acid;

4-(5-(3-(5-(4-Carboxymethyl-2-chloro-phenoxy)-pent-3-en-1-ynyl)-phenyl)-pent-2-en-4-ynyloxy)-3-chloro-phenyl)-acetic acid;

4-(5-(3-(5-(4-Carboxymethyl-3-methyl-phenylsulfanyl)-pent-3-en-1-ynyl)-phenyl)-pent-2-en-4-ynylsulfanyl)-2-methyl-phenoxy)-acetic acid;

3-(4-(5-(3-(5-(4-Carboxymethoxy-3-methyl-phenylsulfanyl)-pent-3-en-1-ynyl)-phenyl)-pent-2-en-4-ynylsulfanyl)-phenyl)-2-ethoxy-propionic acid;

3-(4-(5-(3-(5-(4-Carboxymethoxy-3-methyl-phenylsulfanyl)-pent-3-en-1-ynyl)-phenyl)-pent-2-en-4-ynyloxy)-phenyl)-2-ethoxy-propionic acid;

(4-(5-(3-(5-(4-Carboxymethyl-2-chloro-phenoxy)-3-methyl-pent-3-en-1-ynyl)-phenyl)-3-methyl-pent-2-en-4-ynyloxy)-3-chloro-phenyl)-acetic acid;

(4-(5-(3-(5-(4-Carboxymethyl-3-methyl-phenylsulfanyl)-3-methyl-pent-3-en-1-ynyl)-phenyl)-3-methyl-pent-2-en-4-ynylsulfanyl)-2-methyl-phenoxy)-acetic acid;

3-(4-(5-(3-(5-(4-(2-Carboxy-2-ethoxy-ethyl)-phenoxy)-3-methyl-pent-3-en-1-ynyl)-phenyl)-3-methyl-pent-2-en-4-ynyloxy)-phenyl-2-ethoxy-propionic acid;

3-(4-(5-(3-(5-(4-(2-Carboxy-2-ethoxy-ethyl)-phenylsulfanyl)-3-methyl-pent-3-en-1-ynyl)-phenyl)-3-methyl-pent-2-en-4-ynylsulfanyl)-phenyl-2-ethoxy-propionic acid;

3-(4-(5-(3-(5-(4-(2-Carboxy-2-ethoxy-ethyl)-phenylsulfanyl)-3-methyl-pent-3-en-1-ynyl)-phenyl)-3-methyl-pent-2-en-4-ynyloxy)-phenyl-2-ethoxy-propionic acid;

3-(4-(5-(3-(5-(4-Carboxymethoxy-3-methyl-phenylsulfanyl)-3-methyl-pent-3-en-1-ynyl)-phenyl)-3-methyl-pent-2-en-4-ynylsulfanyl)-phenyl-2-ethoxy-propionic acid;

3-(4-(5-(3-(5-(4-Carboxymethoxy-3-methyl-phenylsulfanyl)-3-methyl-pent-3-en-1-ynyl)-phenyl)-3-methyl-pent-2-en-4-ynyloxyl)-phenyl-2-ethoxy-propionic acid;

3-(4-(5-(7-(5-(4-(2-Carboxy-2-ethoxy-ethyl)-phenoxy)-3-methyl-pent-3-en-1-ynyl)-9-oxo-9H-fluoren-2-yl)-3-methyl-pent-2-en-4-ynyloxy)-phenyl)-2-ethoxy-propionic acid;

3-(4-(5-(7-(5-(4-(2-Carboxy-2-ethoxy-ethyl)-phensulfanyl)-3-methyl-pent-3-en-1-ynyl)-9-oxo-9H-fluoren-2-yl)-3-methyl-pent-2-en-4-ynylsulfanyl)-phenyl)-2-ethoxy-propionic acid;

(4-(5-(7-(5-(4-Carboxymethoxy-3-methyl-phenylsulfanyl)-3-methyl-pent-3-en-1-ynyl)-9-oxo-9H-fluoren-2-yl)-3-methyl-pent-2-en-4-ynylsulfanyl)-2-methyl-phenoxy)-acetic acid;

3-(4-(5-(7-(5-(4-(2-Carboxy-2-ethoxy-ethyl)-phenoxy)-pent-3-en-1-ynyl)-9H-fluoren-2-yl)-3-methyl-pent-2-en-4-ynyloxy)-phenyl)-2-ethoxy-propionic acid;

3-(4-(5-(7-(5-(4-(2-Carboxy-2-ethoxy-ethyl)-phensulfanyl)-pent-3-en-1-ynyl)-9H-fluoren-2-yl)-3-methyl-pent-2-en-4-ynysulfanyl)-phenyl)-2-ethoxy-propionic acid;

(4-(5-(7-(5-(4-Carboxymethoxy-3-methyl-phenylsulfanyl)-3-methyl-pent-3-en-1-ynyl)-9H-fluoren-2-yl)-3-methyl-pent-2-en-4-ynylsulfanyl)-2-methyl-phenoxy)-acetic acid;

3-(4-(5-(7-(5-(4-(2-Carboxy-2-ethoxy-ethyl)-phenoxy)-pent-3-en-1-ynyl)-9-oxo-9H-fluoren-2-yl)-3-methyl-pent-2-en-4-ynylsulfanyl)-phenyl)-2-ethoxy-propionic acid;

3-(4-(5-(7-(5-(4-(2-Carboxy-2-ethoxy-ethyl)-phensulfanyl-pent-3-en-1-ynyl)-9-oxo-9H-fluoren-2-yl)-3-methyl-pent-2-en-4-ynylsulfanyl)-phenyl)-2-ethoxy-propionic acid;

(4-(5-(7-(5-(4-Carboxymethoxy-3-methyl-phenylsulfanyl)-pent-3-en-1-ynyl)-9-oxo-9H-fluoren-2-yl)-3-methyl-pent-2-en-4-ynylsulfanyl)-2-methyl-phenoxy)-acetic acid;

3-(4-(5-(7-(5-(4-(2-Carboxy-2-ethoxy-ethyl)-phenoxy-pent-3-en-1-ynyl)-9H-fluoren-2-yl)-3-methyl-pent-2-en-4-ynyloxy)-phenyl)-2-ethoxy-propionic acid;

3-(4-(5-(7-(5-(4-(2-Carboxy-2-ethoxy-ethyl)-phensulfanyl-pent-3-en-1-ynyl)-9H-fluoren-2-yl)-3-methyl-pent-2-en-4-ynylsulfanyl)-phenyl)-2-ethoxy-propionic acid;

(4-(5-(7-(5-(4-Carboxymethoxy-3-methyl-phenylsulfanyl)-pent-3-en-1-ynyl)-9H-fluoren-2-yl)-3-methyl-pent-2-en-4-ynylsulfanyl)-2-methyl-phenoxy)-acetic acid;

3-(4-(5-(7-(5-(4-(2-Carboxy-2-ethoxy-ethyl)-phenoxy)-3-methyl-pent-3-en-1-ynyl)-9H-carbazol-2-yl)-3-methyl-pent-2-en-4-ynyloxy)-phenyl)-2-ethoxy-propionic acid;

3-(4-(5-(7-(5-(4-(2-Carboxy-2-ethoxy-ethyl)-phensulfanyl)-3-methyl-pent-3-en-1-ynyl)-9H-carbazol-2-yl)-3-methyl-pent-2-en-4-ynylsulfanyl)-phenyl)-2-ethoxy-propionic acid;

(4-(5-(7-(5-(4-Carboxymethoxy-3-methyl-phenylsulfanyl)-3-methyl-pent-3-en-1-ynyl)-9H-carbazol-2-yl)-3-methyl-pent-2-en-4-ynylsulfanyl)-2-methyl-phenoxy)-acetic acid;

3-(4-(5-(7-(5-(4-(2-Carboxy-2-ethoxy-ethyl)-phenoxy-pent-3-en-1-ynyl)-9H-fluoren-2-yl)-3-methyl-pent-2-en-4-ynyloxy)-phenyl)-2-ethoxy-propionic acid;

3-(4-(5-(7-(5-(4-(2-Carboxy-2-ethoxy-ethyl)-phensulfanyl-pent-3-en-1-ynyl)-9H-carbazol-2-yl)-3-methyl-pent-2-en-4-ynylsulfanyl)-phenyl)-2-ethoxy-propionic acid;

(4-(5-(7-(5-(4-Carboxymethoxy-3-methyl-phenylsulfanyl)-pent-3-en-1-ynyl)-9H-carbazol-2-yl)-3-methyl-pent-2-en-4-ynylsulfanyl)-2-methyl-phenoxy)-acetic acid, or a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydriodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the present compound with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the present compound may be converted to a 1:1 mixture of diastereomeric amides by treating with chiral amines, aminoacids, aminoalcohols derived from aminoacids; conventional reaction conditions may be employed to convert acid into an amide; the dia-stereomers may be separated either by fractional crystallization or chromatography and the stereoisomers of the compound of the present invention may be prepared by hydrolysing the pure diastereomeric amide.

Various polymorphs of compound of the present invention forming part of this invention may be prepared by crystallization of compound of the invention under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the the present invention or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the present invention or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

In another aspect, the present invention relates to a method of treating and/or preventing Type I or Type II diabetes.

In a still further aspect, the present invention relates to the use of one or more compounds of the present invention or pharmaceutically acceptable salts thereof for the preparation of a pharmaceutical composition for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, $\beta$3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR $\beta$ agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the $\beta$-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide or senaglinide.

In a further embodiment the present compounds are administered in combination with an $\alpha$-glucosidase inhibitor eg. miglitol or acarbose.

In another embodiment the present compounds are administered in combination with an agent acting on the ATP-dependent potassium channel of the $\beta$-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and mefformin, insulin and a sulphonylurea, insulin and metformin, insulin, insulin and lovastatin, etc.

Furthermore, the present compounds may be administered in combination with one or more antihypertensive agents. Examples of antihypertensive agents are $\beta$-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and oc-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

PHARMACEUTICAL COMPOSITIONS

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of the present invention or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tablefted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the invention dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

If desired, the pharmaceutical composition of the invention may comprise the compound of the present invention in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

Any novel feature or combination of features described herein is considered essential to this invention.

The present invention is further illustrated in the following representative examples which are, however, not intended to limit the scope of the invention in any way.

EXAMPLES

The compounds used as starting materials are either known compounds or compounds which can readily be prepared by methods known per se. The structures of the compounds are confirmed by either elemental analysis (MA), nuclear magnetic resonance (NMR, 300 MHz), mass spectrometry (MS) or optical rotation. NMR shifts ($\delta$) are given in parts per million (ppm) and only selected peaks are given. Mp is melting point and is given in ° C. Column chromatography was carried out using the technique described by W. C. Still et al, J. Org. Chem. 1978, 43, 2923–2925 on Merck silica gel 60 (Art 9385).

The abbreviations as used in the examples have the following meaning:

| | |
|---|---|
| THF: | tetrahydrofuran |
| DMSO: | dimethylsulfoxide |
| CDCl$_3$: | deutorated chloroform |
| DMF: | N,N-dimethylformamide |
| min: | minutes |
| h: | hours |

General Procedure (A)

Step A:

Reacting a compound of formula (a)

Hlg-Z-Hlg   (a)

wherein Z is defined as above and wherein Hlg is chlorine, bromine or iodine, with a appropriate compound of formula T—OH wherein T is defined as above, through a crosscoupling reaction employing a Pd catalyst such as Pd(PPh$_3$)$_2$ or PdCl$_2$(PPh$_3$)$_2$ and a catalytic amount of in example copper (I)iodide and an organic amine base, such as and if needed a cosolvent to give a compound of formula (b)

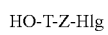
HO-T-Z-Hlg   (b)

wherein Z and T are defined as above and wherein Hlg is chlorine, bromine or iodine.

Step B:

Reacting a compound of formula (b) wherein Z and T are defined as above and wherein Hlg is chlorine, bromine or iodine, with a appropriate compound of formula U—OH wherein U is defined as above, through a crosscoupling reaction employing a Pd catalyst such as Pd(PPh$_3$)$_2$ or PdCl$_2$(PPh$_3$)$_2$ and a catalytic amount of in example copper (I)iodide and an organic amine base, such as and if needed a cosolvent to give a compound of formula (c)

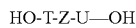
HO-T-Z-U—OH   (c)

wherein Z, T and U are defined as above.

Step C:

Reacting a compound of formula (c), wherein T, Z and U are defined as above, with a compound of formula (d)

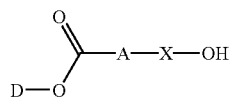

(d)

wherein A, X and D are defined as above except that D is not hydrogen, under Mitsunobu conditions, using a reagent such as triphenylphosphine/diethylazodicarboxylate and the like, to obtain a compound of formula (I), wherein A, B, D, E, L, M, T, U, X, Y and Z are defined as above, except that D and E is not hydrogen, and wherein A and B are identical and wherein X and Y are identical, and wherein L and M is oxygen.

General Procedure (B)

Step A:

Reacting a compound of formula (b), wherein T and Z are defined as above and wherein Hlg is chlorine, bromine or iodine, with a compound of formula (d), wherein A, X and D are defined as above except that D is not hydrogen, under Mitsunobu conditions, using a reagent such as triphenylphosphine/diethylazodicarboxylate and the like to obtain a compound of formula (e)

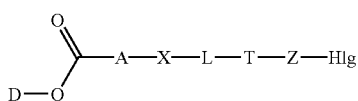

(e)

wherein A, D, T, X and Z are defined as above except that D is not hydrogen and wherein Hlg is chlorine, bromine and iodine, and wherein L is oxygen.

Step B:

Reacting a compound of formula (e), wherein A, D, T, X and Z is defined as above, and wherein Hlg is chlorine, bromine or iodine, and wherein L is oxygen, with a appropriate compound of formula U—OH wherein U is defined as above, through a crosscoupling reaction employing a Pd catalyst such as Pd(PPh$_3$)$_2$ or PdCl$_2$(PPh$_3$)$_2$ and a catalytic amount of in example copper(I)iodide and an organic amine base, such as and if needed a cosolvent to give a compound of formula (f)

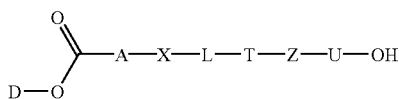

(f)

wherein A, D, T, U, X and Z are defined as above, and wherein L is oxygen.

Step C:

Reacting the compound of formula (f), wherein A, D, T, U, X and Z are defined as above, except that D is not hydrogen, and wherein L is oxygen with a compound of formula (g)

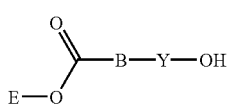

(g)

wherein B, E and Y are defined as above except that E is not hydrogen, under Mitsunobu conditions, using a reagent such as triphenylphosphine/diethylazodicarboxylate and the like, to obtain a compound of formula (I), wherein A, B, D, E, L, M, T, U, X, Y and Z are defined as above, except that D and E is not hydrogen, and wherein L and M is oxygen.

General Procedure (C)

Step A:

Converting the —OH functionality in the compound of formula (c), wherein T, Z and U are defined as above, to an appropriate leaving group (Q) such as p-toluenesulfonate, methanesulfonate, halogen (for example by methods according to: Houben-Weyl, Methoden derorganischen Chemie, Alkohole III, 6/1b, Thieme-Verlag 1984, 4th Ed., pp. 927–939; Comprehensive Organic Transformations. A guide to functional group preparations, VCH Publishers 1989, 1$^{st}$ Ed., pp. 353–363 and *J. Org. Chem*. Vol. 36 (20), 3044–3045, 1971), triflate and the like, to give a compound of formula (h)

(h)

wherein Q, T, U and Z are defined as above.

Step B:

Reacting the compound of formula (h) wherein Q is a leaving group such as p-toluenesulfonate, methanesulfonate, halogen, triflate and the like and wherein T, U and Z are defined as above with a compound of formula (d), wherein A, X and D are defined as above except that D is not hydrogen, to give a compound of formula (I) wherein A, B, D, E, L, M, T, U, X, Y and Z are defined as above, except that D and E is not hydrogen, and wherein A and B are identical and wherein X and Y are identical.

General Procedure (D)

Step A:

Converting the —OH functionality in the compound of formula (b), wherein T and Z are defined as above, and wherein Hlg is chlorine, bromine and iodine, to an appropriate leaving group (Q) such as p-toluenesulfonate, methanesulfonate, halogen (for example by methods according to: Houben-Weyl, Methoden der organischen Chemie, Alkohole III, 6/1 b, Thieme-Verlag 1984, 4th Ed., pp. 927–939; Comprehensive Organic Transformations. A guide to functional group preparations, VCH Publishers 1989, 1$^{st}$ Ed., pp. 353–363 and *J. Org. Chem.*, Vol. 36 (20), 3044–3045, 1971), triflate and the like, to give a compound of formula (i)

(i)

wherein Q, T and Z are defined as above, and wherein Hlg is chlorine, bromine or iodine.

Step B:

Reacting the compound of formula (i) wherein Q is a leaving group such as p-toluenesulfonate, methanesulfonate, halogen, triflate and the like and wherein T and Z are defined as above with a compound of formula (j)

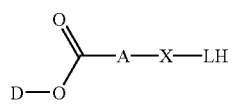
(j)

wherein A, X, D and L are defined as above except that D is not hydrogen, to give a compound of formula (e) wherein A, D, L, T, X and Z are defined as above except that D is not hydrogen and wherein Hlg is chlorine, bromine and iodine.

Step C:

Reacting a compound of formula (e), wherein A, D, L, T, X and Z is defined as above, and wherein Hlg is chlorine, bromine or iodine, with an appropriate compound of formula U—OH wherein U is defined as above, through a crosscoupling reaction employing a Pd catalyst such as Pd(PPh$_3$)$_2$ or PdCl$_2$(PPh$_3$)$_2$ and a catalytic amount of in example copper (I)iodide and an organic amine base, such as and if needed a cosolvent to give a compound of formula (f) wherein A, D, L, T, U, X and Z are defined as above.

Step D:

Converting the —OH functionality in the compound of formula (f), wherein A, D, L, T, U, X and Z are defined as above, to an appropriate leaving group (Q) such as p-toluenesulfonate, methanesulfonate, halogen (for example by methods according to: Houben-Weyl, Methoden derorganischen Chemie, Alkohole III, 6/1b, Thieme-Verlag 1984, 4th Ed., pp. 927–939; Comprehensive Organic Transformations. A guide to functional group preparations, VCH Publishers 1989, 1$^{st}$ Ed., pp. 353–363 and *J. Org. Chem.*, Vol. 36 (20), 3044–3045, 1971), triflate and the like, to give a compound of formula (k)

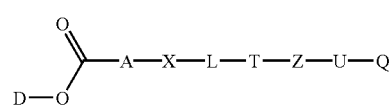
(k)

wherein A, D, L, T, U, Q, X and Z are defined as above.

Step E:

Reacting the compound of formula (k) wherein Q is a leaving group such as p-toluenesulfonate, methanesulfonate, halogen, triflate and the like and wherein A, D, L, T, U, X and Z are defined as above with a compound of formula (l)

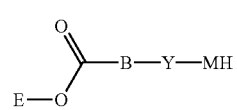
(l)

wherein B, E, M and Y are defined as above except that E is not hydrogen, to give a compound of formula (I) wherein A, B, D, E, L, M, T, U, X, Y and Z are defined as above, except that D and E is not hydrogen.

General Procedure (E)

Step A:

By chemical or enzymatic saponification of a compound of formula (I) wherein A, B, D, E, L, M, T, U, X, Y and Z are defined as above, except that D and E are not hydrogen, to give a compound of formula (I) wherein A, B, L, M, T, U, X, Y and Z are defined as above, and wherein D and E is hydrogen.

General Procedure (F)

Step A:

Reacting a compound of formula (m)

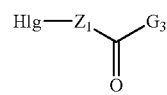
(m)

wherein $Z_1$ taken together with $Z_2$ form a divalent polycyclic ringsystem as defined for Z above, and wherein Hlg is chlorine, bromine or iodine and wherein $G_3$ is defined as above, through a Wittig-like process with for example $(EtO)_2PO(CHG_4)COOR_6$ (wherein $R_6$ is an $C_{1-3}$-alkyl group and wherein $G_4$ is defined as above), in the presence of a base such as sodium hydride, EtONa and the like to give a compound of formula (n)

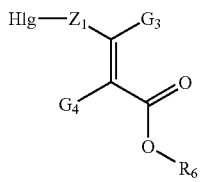

(n)

wherein $R_6$ is defined as above and wherein $Z_1$ taken together with $Z_2$ form a divalent polycyclic ringsystem as defined for Z above, and wherein Hlg is chlorine, bromine or iodine and wherein $G_3$ and $G_4$ are defined as above.

Step B:

Reducing the compound of formula (n), wherein $R_6$ is defined as above and wherein $Z_1$ taken together with $Z_2$ form a divalent polycyclic ringsystem as defined for Z above, and wherein Hlg is chlorine, bromine or iodine and wherein $G_3$ and $G_4$ are defined as above with a suitable reagent such as diisobutylaluminium hydride, to give a compound of formula (o)

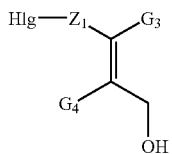

(o)

wherein $Z_1$ taken together with $Z_2$ form a divalent polycyclic ringsystem as defined for Z above, and wherein Hlg is chlorine, bromine or iodine and wherein $G_3$ and $G_4$ are defined as above.

Step C:

Reacting the compound of formula (o), wherein $G_3$ and $G_4$ are defined as above and wherein $Z_1$ taken together with $Z_2$ form a divalent polycyclic ringsystem as defined for Z above, and wherein Hlg is chlorine, bromine or iodine with a appropriate boronic acid of formula (p)

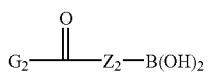

(p)

wherein $Z_2$ taken together with $Z_1$ form a divalent polycyclic ringsystem as defined for Z above, and $G_2$ is defined as above, to give a compound of formula (q)

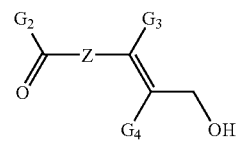

(q)

wherein Z, $G_2$, $G_3$ and $G_4$ are defined as above.

Step D:

Protecting the —OH functionality in a compound of formula (q) wherein Z, $G_2$, $G_3$ and $G_4$ are defined as above, with an appropriate protecting group such as tert-butyldimethylsilyl to give a compound of formula (r)

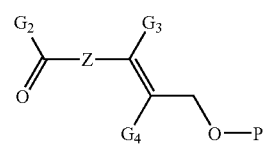

(r)

wherein Z, $G_2$, $G_3$ and $G_4$ are defined as above and wherein P is an appropriate protecting group such as tert-butyidimethylsilyl.

Step E:

Reacting the compound of formula (r), wherein Z, $G_2$, $G_3$ and $G_4$ are defined as above and wherein P is an appropriate protecting group such as tert-butyldimethylsilyl, through a Wittig-like process with for example $(EtO)_2PO(CHG_1)COOR_6$ (wherein $R_6$ is an $C_{1-3}$-alkyl group and wherein $G_1$ is defined as above), in the presence of a base such as sodium hydride, EtONa and the like to give a compound of formula (s)

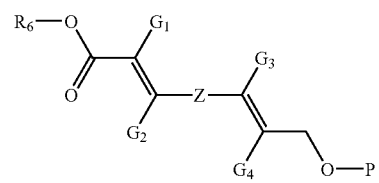

(s)

wherein Z, $G_1$, $G_2$, $G_3$ and $G_4$ is defined as above and wherein P is an appropriate protecting group such as tert-butyldimethylsilyl and wherein $R_6$ is an $C_{1-3}$-alkyl group.

Step F:

Reducing the compound of formula (s), wherein Z, $G_1$, $G_2$, $G_3$ and $G_4$ are defined as above and wherein P is an appropriate protecting group such as tert-butyldimethylsilyl and wherein $R_6$ is an $C_{1-3}$-alkyl group, with a suitable reagent such as diisobutylaluminium hydride, to give a compound of formula (t)

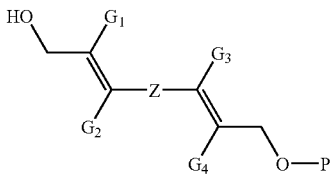

(t)

wherein Z, $G_1$, $G_2$, $G_3$ and $G_4$ are defined as above and wherein P is an appropriate protecting group such as tert-butyldimethylsilyl.

Step G:

Reacting a compound of formula (t) wherein Z, $G_1$, $G_2$, $G_3$ and $G_4$ are defined as above and wherein P is an appropriate protecting group such as tert-butyldimethylsilyl with a compound of formula (d)

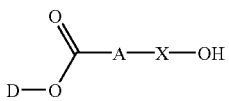

(d)

wherein D, A and X are defined as above under Mitsunobu conditions, using a reagent such as triphenylphosphine/diethylazodicarboxylate and the like to obtain a compound of formula (u)

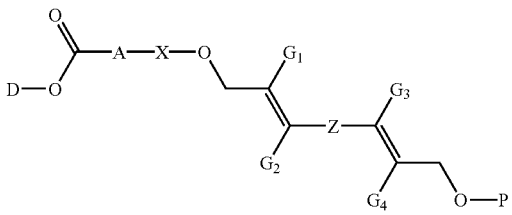

(u)

wherein A, D, X, Z, $G_1$, $G_2$, $G_3$ and $G_4$ are defined as above and wherein P is an appropriate protecting group such as tert-butyldimethylsilyl.

Step H:

Deprotecting a compound of formula (u) wherein A, D, X, Z, $G_1$, $G_2$, $G_3$ and $G_4$ are defined as above and wherein P is an appropriate protecting group such as tertbutyidimethyl-silyl to give a compound of formula (v)

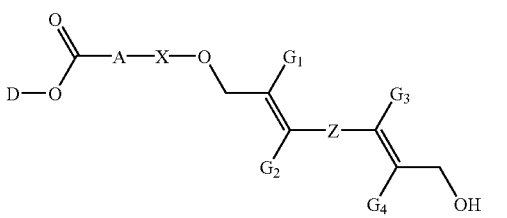

(v)

wherein A, D, X, Z, $G_1$, $G_2$, $G_3$ and $G_4$ are defined as above.

Step I:

Reacting a compound of formula (v) wherein A, D, X, Z, $G_1$, $G_2$, $G_3$ and $G_4$ are defined as above, with a compound of formula (x)

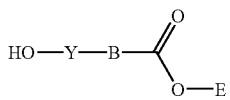

(x)

wherein Y, B and E are defined as above under Mitsunobu conditions, using a reagent such as triphenylphosphine/diethylazodicarboxylate and the like to obtain a compound of formula (I) wherein A, B, D, E, X, Y and Z are defined as above, except that D and E is not hydrogen and wherein L and M is oxygen and wherein T is $—CH_2(CG_1)=(CG_2)—$ and wherein U is $—CH_2(CG_3)=(CG_4)—$.

General Procedure (G)

Step A:

Reacting a compound of formula (a) wherein Z is defined as above and wherein Hlg is chlorine, bromine or iodine, with a appropriate compound of formula T-COOR$_5$ wherein T is defined as above and $R_5$ is $C_{1-6}$-alkyl, through a crosscoupling reaction employing a Pd catalyst such as Pd(PPh$_3$)$_2$ or PdCl$_2$(PPh$_3$)$_2$ and a catalytic amount of in example copper(I)iodide and an organic amine base, such as and if needed a cosolvent to give a compound of formula (y)

$R_5OOC$-T-Z-Hlg (y)

wherein Z and T are defined as above and wherein Hlg is chlorine, bromine or iodine and wherein $R_5$ is $C_{1-6}$-alkyl.

Step B:

Reacting a compound of formula (y) wherein Z and T are defined as above and wherein Hlg is chlorine, bromine or iodine and wherein $R_5$ is $C_{1-6}$-alkyl, with an appropriate compound of formula U-COOR$_5$ wherein U is defined as above and $R_5$ is $C_{1-6}$-alkyl, through a crosscoupling reaction employing a Pd catalyst such as Pd(PPh$_3$)$_2$ or PdCl$_2$(PPh$_3$)$_2$ and a catalytic amount of in example copper(I)iodide and an organic amine base, such as and if needed a cosolvent to give a compound of formula (z)

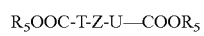

$R_5OOC$-T-Z-U—COOR$_5$ (z)

wherein Z, T, U and $R_5$ are defined as above.

Step C:

Reducing a compound of formula (z), wherein Z, T, U and $R_5$ are defined as above with a suitable reagent such as diisobutylaluminium hydride or aluminium chloride/lithium aluminium hydride, to give a compound of formula (c).

Using a combination of the above methods, or methods analogous hereof, various compounds may be made within the scope of the present invention.

Example 1

General Procedure A (E)(E)(S)(S) 2-Ethoxy-3-{4-[5-(4-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester

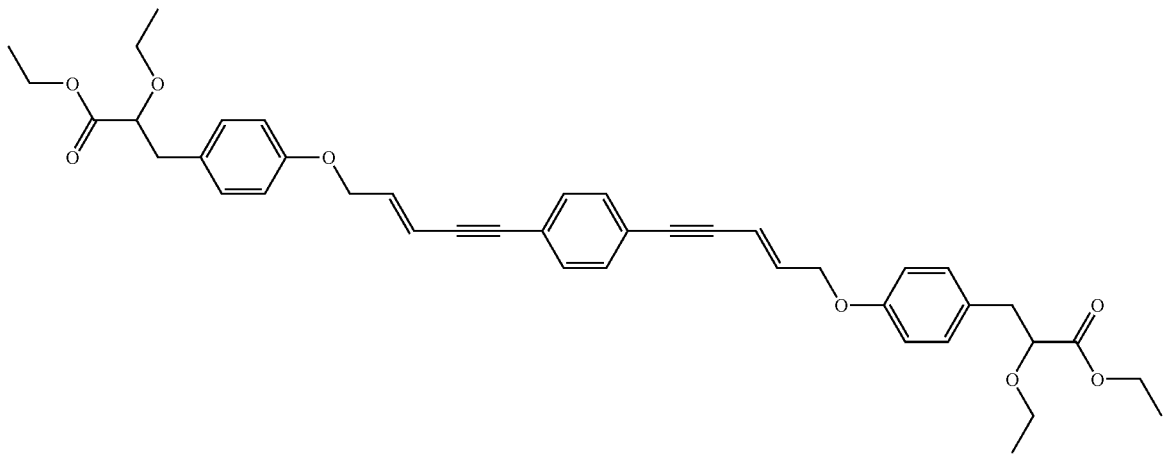

Step A-B:

To a solution of 1,4-diiodobenzene (1.32 g, 4.0 mmol) in diisopropylamine (12 mL) under a nitrogen atmosphere were added copper(I) iodide (60 mg, 0.3 mmol) and tetrakis(triphenylphosphine)palladium (80 mg, 0.07 mmol). After the mixture stirred for 1 h, a solution of 2-penten-4-yn-1-ol (1.0 g, 12.0 mmol) in diisopropylamine (7 mL) was added. After stirring under a nitrogen at 60° C. for 8 h, the reaction mixture was filtered and the filtrate evaporated to dryness. The product was purified by flash chromatography using toluene/ethyl acetate (2:1) graduated to ethyl acetate as eluent to give 520 mg (55%) of (E)(E) 5-[4-(5-hydroxy-pent-3-en-1-ynyl)-phenyl]-pent-2-en-4-yn-1-ol.

$^1$H NMR (CDCL$_3$): δ 1.47 (2H, bs), 4.28 (2H, bs), 5.97 (2H, dt), 6.38 (2H, dt), 7.38 (4H, s).

*rahedron Letters*, Vol. 35, No 19, 3139–3142, 1994)(357 mg, 1.5 mmol) and (E)(E) 5-[4-(5-hydroxy-pent-3-en-1-ynyl)-phenyl]-pent-2-en-4-yn-1-ol (120 mg, 0.5 mmol) in dry THF (25 mL). After 24 h the reaction mixture was filtered, and the filtrate concentrated in vacuo. The crude product was purified by flash chromatography using toluene/ethyl acetate (19:1) graduated to toluene/ethyl acetate (4:1) as eluent to give 90 mg (27%) of the title compound.

$^1$H NMR (CDCL$_3$): δ 1.18 (6H, t), 1.23 (6H, t), 2.95 (4H, d), 3.30–3.43 (2H, m), 3.55–3.67 (2H, m), 3.98 (2H, t), 4.18 (4H, q), 4.63 (4H, dd), 6.07 (2H, dt), 6.39 (2H, dt), 6.85 (4H, d), 7.17 (4H, d), 7.27 (4H, s), 7.37 (4H, s).

Example 2

General Procedure E (E)(E)(S)(S) 3-{4-[5-(4-{5-[4-(2-Carboxy-2-ethoxy-ethyl)-phenoxy]-pent-3-en-1-ynyl}-phenyl}-pent-2-en-4-ynyloxy]-phenyl)-2-ethoxy-propionic acid Step C:

Under a atmosphere of nitrogen, azodicarboxylic dipiperidide (504 mg, 2.0 mmol) was added at 0–5° C. to a stirred solution of tributylphosphine (404 mg, 2.0 mmol), (S)-2-ethoxy-3-(4-hydroxyphenyl)-propionic acid ethyl ester (*Tet-*

Step A:

To a solution of (E)(E)(S)(S) 2-ethoxy-3-{4-[5-(4-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester (example 1) (88 mg 0.13 mmol) in THF (3 mL) and ethanol (3 mL) was added 1N sodium hydroxide (2 mL). After stirring at room temperature for 1 h, the reaction mixture was concentrated in vacuo, added water and 1N hydrochloride acid to pH 1. The product was extracted with dichloromethane (×3) and the combined organic phases were dried (MgSO$_4$), filtered and concentrated in vacuo to give the title compound as a crystalline product. The product was recrystallised from ethyl acetate and petroleum ether to give 35 mg of the title compound.

$^1$H NMR (acetone-d$_6$): δ 1.18 (6H, t), 2.95 (2H, dd), 3.10 (2H, dd), 3.42–3.53 (2H, m), 3.55–3.68 (2H, m), 4.07 (2H, dd), 4.63 (3H, dd), 6.07 (2H, dt), 6.39 (2H, dt), 6.85 (4H, d), 7.15 (4H, d), 7.38 (4H, s).

Example 3

General Procedure A (E)(E) 3-Chloro-4-(5-{4-[5-(3-chloro-4-ethoxyarbonylmethyl-phenoxy)-pent-3-en-1-ynyl]-phenyl}-pent-2-en-4-ynyloxy)-phenyl]-acetic acid ethyl ester

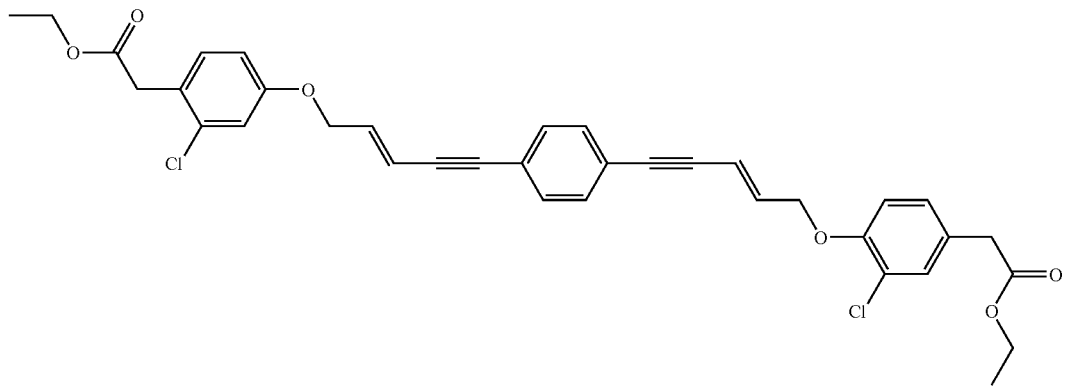

Step C:

Under a atmosphere of nitrogen, azodicarboxylic dipiperidide (504 mg, 2.0 mmol) was added at 0–5° C. to a stirred solution of tributylphosphine (404 mg, 2.0 mmol), (3-chloro-4-hydroxyphenyl)propionic acid ethyl ester (322 mg, 1.5 mmol) and (E)(E) 5-[4-(5-hydroxy-pent-3-en-1-ynyl)-phenyl]-pent-2-en-4-yn-1-ol (example 1, Step A-B) (120 mg, 0.5 mmol) in dry THF (25 mL). After 1 h the reaction mixture was filtered, and the filtrate concentrated in vacuo. The crude product was purified by flash chromatography using toluene graduated to toluene/ethyl acetate (1:1) as eluent. The product was recrystallised from ethyl acetate to give 150 mg (48%) of the title compound.

$^1$H NMR (CDCL$_3$): δ 1.24 (6H, t), 3.53 (4H, s), 4.15 (4H, q), 4.71 (2H, d), 6.15 (2H, dt), 6.40 (2H, dt), 6.88 (2H, d), 7.14 (2H, dd), 7.33 (2H, d), 7.38 (4H, s).

Example 4

General Procedure E (E)(E) [4-(5-{4-[5-(4-Carboxymethyl-3-chloro-phenoxy)-pent-3-en-1-ynyl]-phenyl}-pent-2-en-4-ynyloxy)-3-chloro-phenyl]-acetic acid

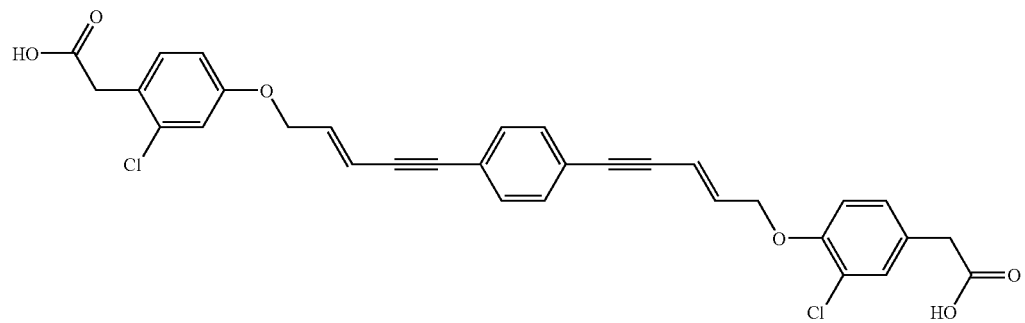

Step A:

To a solution of (E)(E) 3-chloro-4-(5-{4-[5-(3-chloro-4-ethoxycarbonylmethyl-phenoxy)-pent-3-en-1-ynyl]-phenyl}-pent-2-en-4-ynyloxy)-phenyl]-acetic acid ethyl ester (example 3) (150 mg 0.24 mmol) in THF (8 mL) and ethanol (4 mL) was added 1N sodium hydroxide (4 mL). After stirring at room temperature for 1 h, the reaction mixture was concentrated in vacuo, added water and 1N hydrochloride acid to pH 1. The product was extracted with dichloromethane (×3) and the combined organic phases were dried (MgSO$_4$), filtered and concentrated in vacuo to give the title compound as a crystalline product. The product was recrystallised from ethyl acetate/THF and petroleum ether to give 90 mg (66%) of the title compound.

$^1$H NMR (acetone-d$_6$): δ 3.59 (4H, s), 4.82 (4H, d), 6.23 (2H, dt), 6.49 (2H, dt), 7.10 (2H, d), 7.23 (2H, dd), 7.40 (2H, d), 7.47 (4H, s).

Example 5

General Procedure A (E)(E)(S)(S) 2-Ethoxy-3-{4-[5-(3-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester were added copper(I) iodide (75 mg, 0.4 mmol) and tetrakis(triphenylphosphine)palladium (80 mg, 0.07 mmol). After the mixture stirred for 1 h, a solution of 2-penten-4-yn-1-ol (2.0 g, 24.0 mmol) in diisopropylamine (10 mL) was added. After stirring at 60° C. for 16 h, the reaction mixture was filtered and the filtrate evaporated to dryness. The product was purified by flash chromatography using toluene/ethyl acetate (9:1) graduated to ethyl acetate as eluent to give 1.35 g (71%) of (E)(E) 5-[3-(5-hydroxy-pent-3-en-1-ynyl)-phenyl]-pent-2-en-4-yn-1-ol.

$^1$H NMR (CDCL$_3$): δ 4.26 (4H, d), 5.95 (2H, dt), 6.35 (2H, dt), 7.23–7.30 (m, 1H), 7.38 (2H, dd), 7.52 (1H, s).

Step C:

Under a atmosphere of nitrogen, azodicarboxylic dipiperidide (423 mg, 1.68 mmol) was added at 0–5° C. to a stirred solution of tributylphosphine (340 mg, 1.68 mmol), (S)-2-ethoxy-3-(4-hydroxyphenyl)-propionic acid ethyl este (*Tetrahedron Letters*, Vol. 35, No 19, 3139–3142, 1994)(400 mg, 1.68 mmol) and (E)(E) 5-[3-(5-hydroxy-pent-3-en-1-ynyl)-phenyl]-pent-2-en-4-yn-1-ol (200 mg, 0.84 mmol) in dry THF (20 mL). After 1 h the reaction mixture was filtered, and the filtrate concentrated in vacuo. The crude product was purified by flash chromatography using toluene/ethyl acetate (9:1) as eluent to give 130 mg (23%) of the title compound.

$^1$H NMR (CDCL$_3$): δ 1.17 (6H, t), 1.22 (6H, t), 2.95 (4H, d), 3.30–3.42 (2H, m), 3.55–3.65 (2H, m), 3.98 (2H, t), 4.18

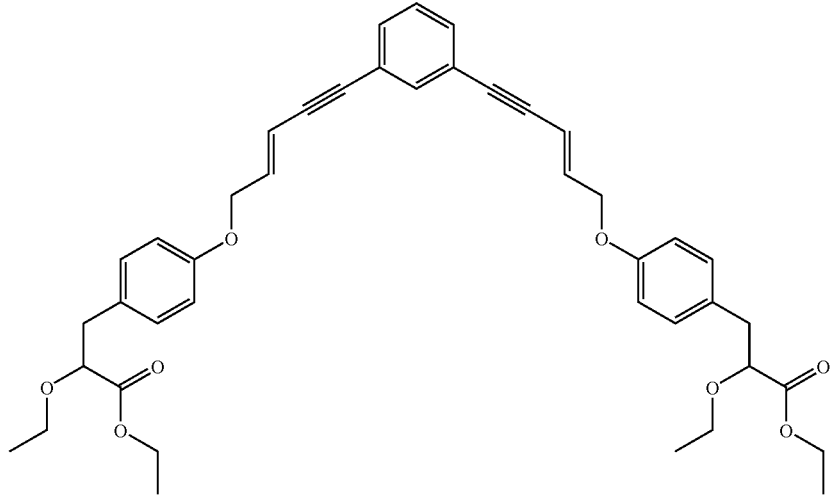

Step A-B:

To a solution of 1,3-diiodobenzene (2.64 g, 8.0 mmol) in diisopropylamine (25 mL) under a nitrogen atmosphere (4H, q), 4.62 (4H, dd), 6.05 (2H, dt), 6.39 (2H, dt), 6.85 (4H, d), 7.17 (4H, d), 7.23–7.30 (m, 1H), 7.37 (2H, dd), 7.50 (1H, s).

Example 6

General Procedure E (E)(E)(S)(S) 3-{4-[5-(3-{5-[4-(2-Carboxy-2-ethoxy-ethyl)-phenoxy]-pent-3-en-1-ynyl}-phenyl)-pent-2-en-4-ynyloxy]-phenyl}-2-ethoxy-propionic acid

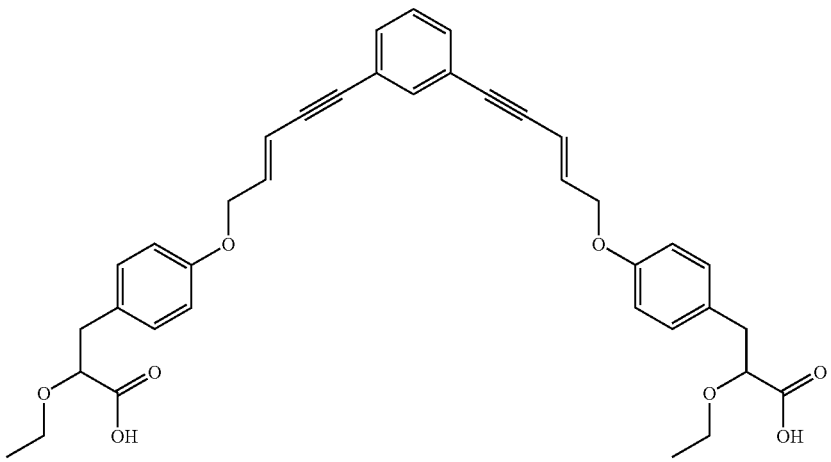

Step A:

To a solution of (E)(E)(S)(S) 2-ethoxy-3-{4-[5-(3-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester (example 5) (130 mg 0.2 mmol) in THF (3 mL) and ethanol (3 mL) was added 1N sodium hydroxide (1.5 mL). After stirring at room temperature for 2 h, the reaction mixture was concentrated in vacuo, added water and 1N hydrochloride acid to pH 1. The product was extracted with dichloromethane (×3) and the combined organic phases were dried (MgSO$_4$), filtered and concentrated in vacuo to give the title compound as a crystalline product. The product was recrystallised from tetrachloromethane and petroleum ether to give 72 mg (58%) of the title compound.

$^1$H NMR (acetone-d$_6$): δ 1.12 (6H, t), 2.88 (2H, dd), 3.02 (2H, dd), 3.32–3.43 (2H, m), 3.57–3.68 (2H, m), 4.04 (2H, dd), 4.70 (4H, dd), 6.15 (2H, dt), 6.47 (2H, dt), 6.90 (4H, d), 7.23 (4H, d), 7.38–7.49 (m, 1H), 7.37 (2H, dd), 7.52 (1H, s).

Example 7

General Procedure A (E)(E) [3-Chloro-4-(5-{3-[5-(2-chloro-4-ethoxycarbonylmethyl-phenoxy)-pent-3-en-1-ynyl]-phenyl}-pent-2-en-4-ynyloxy)-phenyl]-acetic acid ethyl ester

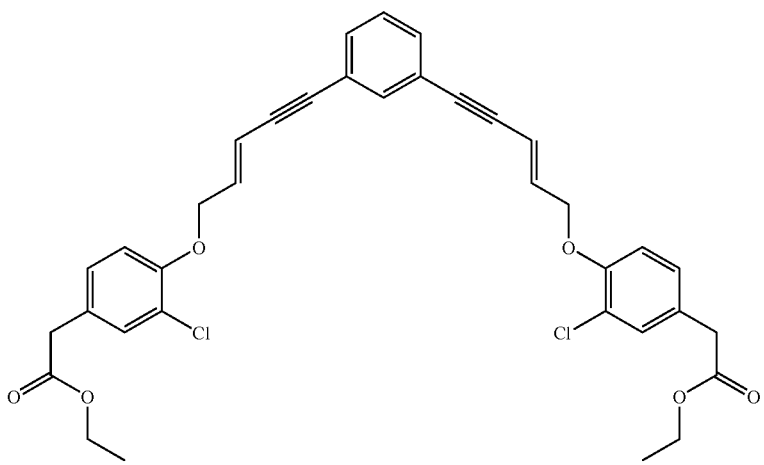

Step C:

Under a atmosphere of nitrogen, azodicarboxylic dipiperidide (423 mg, 1.68 mmol) was added at 0–5° C. to a stirred solution of tributylphosphine (340 mg, 1.68 mmol), (3-chloro-4-hydroxyphenyl)propionic acid ethyl ester (361 mg, 1.68 mmol) and (E)(E) 5-[3-(5-hydroxy-pent-3-en-1-ynyl)-phenyl]-pent-2-en-4-yn-1-ol (example 5, Step A-B) (200 mg, 0.84 mmol) in dry THF (20 mL). After 1 h the reaction mixture was filtered, and the filtrate concentrated in vacuo. The crude product was purified by flash chromatography using toluene/ethyl acetate (19:1) as eluent to give 180 mg (34%) of the title compound.

$^1$H NMR (CDCL$_3$): δ 1.26 (6H, t), 3.53 (4H, s), 4.15 (4H, q), 4.69 (2H, d), 6.13 (2H, dt), 6.39 (2H, dt), 6.87 (2H, d), 7.12 (2H, dd), 7.20–7.38 (5H, m), 7.50 (1H, s).

Example 8

General Procedure E (E)(E) [4-(5-{3-[5-(4-Carboxymethyl-2-chloro-phenoxy)-pent-3-en-1-ynyl]-phenyl}-pent-2-en-4-ynyloxy)-3-chloro-phenyl]-acetic acid

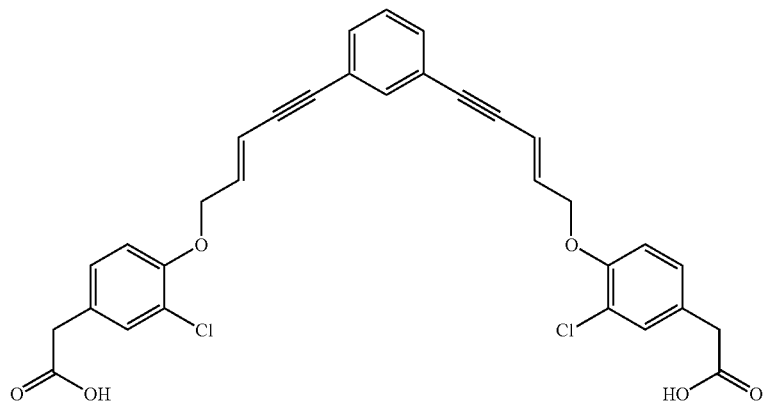

Step A:

To a solution of (E)(E) [3-chloro-4-(5-{3-[5-(2-chloro-4-ethoxycarbonylmethyl-phenoxy)-pent-3-en-1-ynyl]-phenyl}-pent-2-en-4-ynyloxy)-phenyl]-acetic acid ethyl ester (example 7) (180 mg 0.28 mmol) in THF (3 mL) and ethanol (3 mL) was added 1N sodium hydroxide (1.5 mL).

After stirring at room temperature for 4 h, the reaction mixture was concentrated in vacuo, added water and 1N hydrochloride acid to pH 1. The product was extracted with dichloromethane/isopropanol (×3) and the combined organic phases were dried (MgSO$_4$), filtered and concentrated in vacuo to give 125 mg of the title compound as a crystalline product.

$^1$H NMR (acetone-d$_6$): δ 3.60 (4H, s), 4.82 (4H, d), 6.23 (2H, dt), 6.50 (2H, dt), 7.10 (2H, d), 7.23 (2H, dd), 7.39–7.50 (5H, m), 7.53 (1H, s).

Example 9

General Procedure A (E)(E)(S)(S) 2-(2-Benzoyl-phenylamino)-3-(4-{5-[4-(5-{4-[2-(2-benzoyl-phenylamino)-2-methoxycarbonyl-ethyl]-phenoxy}-pent-3-en-1-ynyl)-phenyl]-pent-2-en-4-ynyloxy}-phenyl)-propionic acid methyl ester

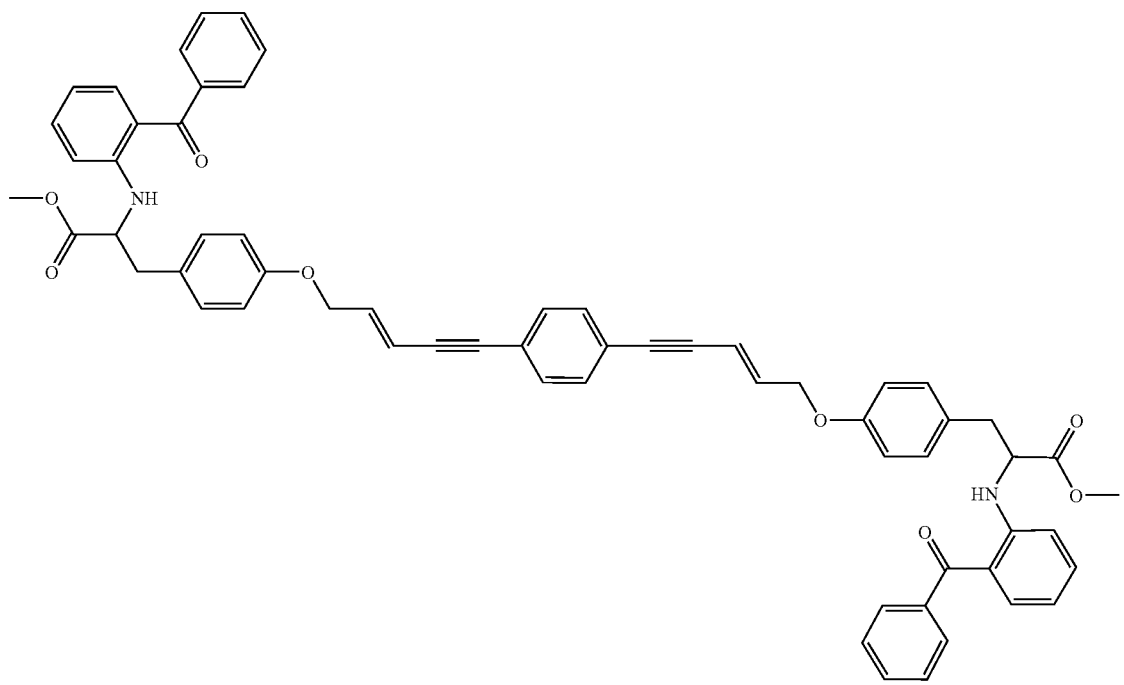

Step C:

Under a atmosphere of nitrogen, azodicarboxylic dipiperidide (1.0 g, 4.0 mmol) was added at 0–5° C. to a stirred solution of tributylphosphine (808 mg, 4.0 mmol), (S)-2-(2-benzoyloxy-phenylamino)-3-(4-hydroxyphenyl)-propionic acid methyl ester (820 mg, 2.18 mmol) and (E)(E) 5-[4-(5-hydroxy-pent-3-en-1-ynyl)-phenyl]-pent-2-en-4-yn-1-ol (example 1, Step A-B) (260 mg, 1.1 mmol) in dry THF (20 mL). After 2 h the reaction mixture was filtered, and the filtrate concentrated in vacuo. The crude product was purified by flash chromatography using toluene/ethyl acetate (19:1) as eluent, to give 370 mg (36%) of the title compound as an oil.

$^1$H NMR (CDCL$_3$): δ 3.12 (2H, dd), 3.23 (2H, dd), 3.70 (6H, s), 4.39 (2H, q), 4.60 (4H, d), 6.04 (2H, dt), 6.37 (2H, dt), 6.53–6.67 (4H, m), 6.85 (4H, d), 7.14–7.63 (22H, m), 8.87 (2H, d).

Example 10

General Procedure E (E)(E)(S)(S) 2-(2-Benzoyl-phenylamino)-3-(4-{5-[4-(5-{4-[2-(2-benzoyl-phenylamino)-2-carboxy-ethyl]-phenoxy}-pent-3-en-1-ynyl)-phenyl]-pent-2-en-4-ynyloxy}-phenyl)-propionic acid

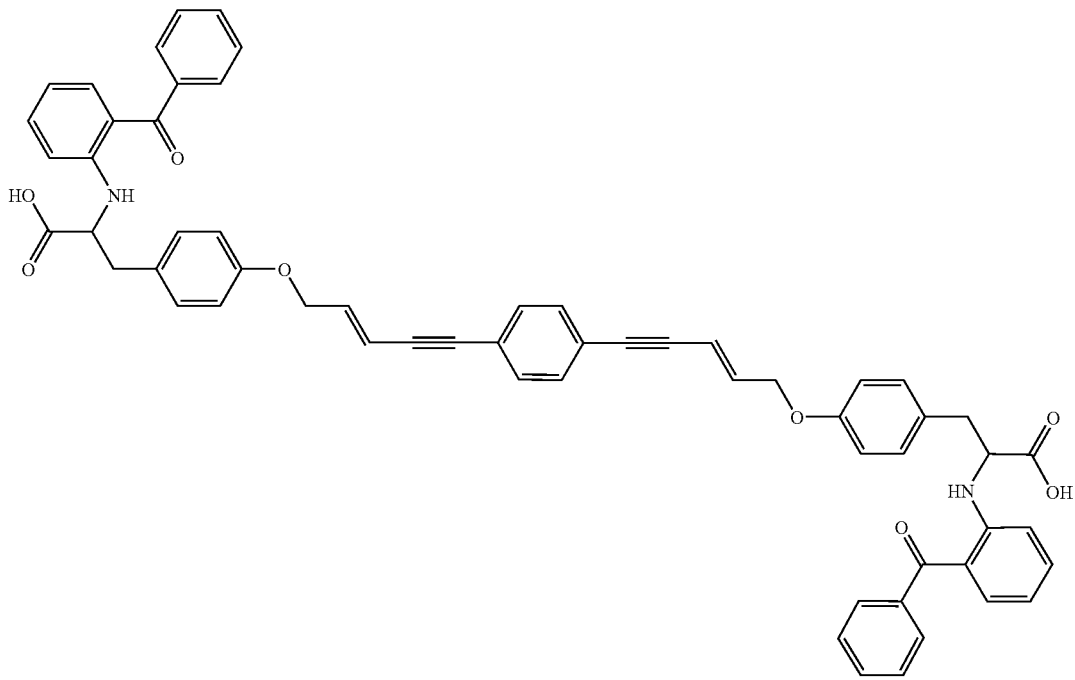

Step A:

To a solution of (E)(E)(S)(S) 2-(2-benzoyl-phenylamino)-3-(4-{5-[4-(5-{4-[2-(2-benzoyl-phenylamino)-2-methoxycarbonyl-ethyl]-phenoxy}-pent-3-en-1-ynyl)-phenyl]-pent-2-en-4-ynyloxy}-phenyl)-propionic acid methyl ester (example 9) (370 mg 0.39 mmol) in THF (3 mL) and ethanol (3 mL) was added 1N sodium hydroxide (2 mL). After stirring at room temperature for 1 h, the reaction mixture was concentrated in vacuo, added water and 1N hydrochloride acid to pH 1. The product was extracted with dichloromethane (×3) and the combined organic phases were dried (MgSO$_4$), filtered and concentrated in vacuo to give the title compound as a crystalline product. The product was recrystallised from ethyl acetate and petroleum ether to give 200 mg of the title compound.

$^1$H NMR (CDCl3): δ 3.15 (2H, dd), 3.29 (2H, dd), 4.40 (2H, bs), 4.55 (4H, d), 6.03 (2H, d), 6.35 (2H, dt), 6.57–6.74 (4H, m), 6.82 (4H, d), 7.22 (4H, d), 7.30–7.63 (18H, m), 8.85 (2H, bs).

Example 11

General Procedure F (E)(E)(S)(S) 2-Ethoxy-3-{4-[3-(4'-{3-[4-(2-ethoxy-2-ethoxycarbonyl-ethyl)-phenoxy]-1-methyl-propenyl}-biphenyl-4-yl)-but-2-enyloxy]-phenyl}-propionic acid ethyl ester

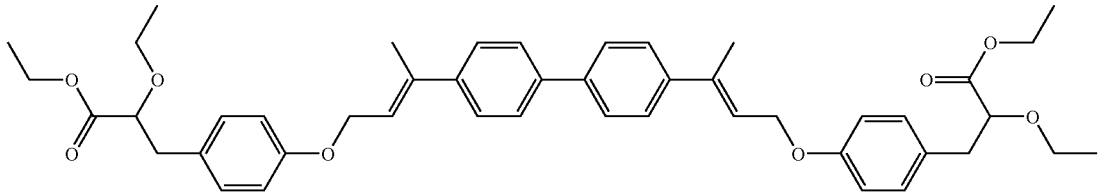

Step A:

Sodium (5.52 g, 0.24 mol) was dissolved in ethanol (200 mL). A solution of triethylphosphonoacetate (62.7 g, 0.28 mol) in ethanol (100 mL) was slowly added. The mixture was stirred for 20 min. and added a solution og 4-iodoacetophenone (49.21 g, 0.20 mol) in hot ethanol (200 mL). The mixture was stirred at 80° C. for 66 h. The mixture was cooled and ethanol evaporated. The residue was added 1N HCl (400 mL) and ethyl acetate (400 mL). The aqueous layer was further extracted with ethyl acetate (2×200 mL). The combined organic phases were washed with brine, dried (MgSO$_4$), filtered and evaporated. The product was purified by column chromatography using heptane/ethyl ether (39:1) as eluent to give 30.0 g (46%) of (E) 3-(4-iodophenyl)but-2-onoic acid ethyl ester.

$^1$H NMR (CDCl$_3$): δ 1.31 (3H, t), 2.53 (3H, s), 4.21 (2H, q), 6.11 (1H, s), 7.19 (2H, d), 7.69 (2H, d).

Step B:

Under a atmosphere of nitrogen, (E) 3-(4-iodophenyl)but-2-onoic acid ethyl ester (10.1 g, 32.0 mmol) was dissolved in dry THF (300 mL). The solution was cooled to −15° C. and slowly added a 1M solution of DIBAL-H in toluene (96.0 ml, 96.0 mmol). The mixture was slowly warmed to room temperature and stirred for 1 h. Methanol (50 ml) was carefully added, followed by 1N HCl (500 ml) and the resulting mixture extracted with ethyl acetate (3×500 ml). The combined organic extracts were washed with brine, dried (MgSO$_4$), and evaporated to give 8.8 g of (E) 3-(4-iodophenyl)but-2-en-1-ol.

$^1$H NMR (CDCl$_3$): δ 1.42 (1H, ds), 2.04 (3H, s), 4.35 (2H, d), 5.97 (1H, t), 7.13 (2H, d), 7.63 (2H, d).

Step C:

Tetrakis(triphenylphoshine)palladium(0) (0.46 g, 0.4 mmol, 4 mol%) was added, under nitrogen, to a stirred solution of (E) 3-(4-iodophenyl)but-2-en-1-ol (2.74 g, 10.0 mmol) in DME (100 mL), and the solution stirred at room temperature for 10 min. Aqueous 2M sodium carbonate (30.0 ml, 60.0 mmol) was then added, the mixture stirred for 10 min, then 4-acetyl boronic acid (3.28 g, 20.0 mmol) was added, and the reaction mixture heated to 65° C. for 18 h, under reflux. and at room temperature for another 3 days. The reaction mixture was diluted with 1N HCl (200 ml) and the products extracted into ethyl acetate (2×200 ml). The combined organic extracts were washed with brine, dried (MgSO$_4$), and evaporated to give the crude product, which was purified by column chromatography on silica gel using heptane/ethyl acetate (3:2) eluent) graduated to heptane/ethyl acetate (2:3) as eluent, to give 2.0 g (75%) of (E) 1-[4'-(3-hydroxy-1-methyl-propenyl)-biphenyl-4-yl]-ethanone.

$^1$H NMR (CDCl$_3$): δ 2.12 (3H, s), 2.64 (3H, s), 4.41 (2H, q), 6.07 (1H, t), 7.51 (2H, d), 7.61 (2H, d), 7.71 (2H, d), 8.03 (2H, d).

Step D:

To a suspension of (E) 1-[4'-(3-hydroxy-1-methyl-propenyl)-biphenyl-4-yl]-ethanone (1.1 g, 4.13 mmol) in dichloromethane (40 mL) was under a atmosphere of nitrogen added imidazole (0.42 g, 6.20 mmol) and tert-butyldimethylsilyl chloride (0.78 g, 5.15 mmol). The mixture was stirred at room temperature for 18 h. Dichloromethane (15 mL) was added and the reaction mixture was washed with water, sodium hydrogencarbonate solution and brine. The organic phase was dried (MgSO$_4$), filtered and concentrated in vacuo. The residue was submitted to column chromatography on silica gel, using heptane/ethyl acetate (4:1) as eluent, to give 1.36 g (87%) of (E) 1-{4'-[3-(tert-butyldimethylsilanyloxy)-1-methylpropenyl]-biphenyl-4-yl}ethanone. M.p. 100–106° C.

$^1$H NMR (CDCl$_3$) δ: 0.13 (6H, s), 0.97 (9H, s), 2.10 (3H, s), 2.65 (3H, s), 4.13 (2H, d), 5.98 (1H, dt), 7.51 (2H, d), 7.60 (2H, d) 7.69 (2H, d), 8.02 (2H, d).

Step E:

Sodium (0.42 g, 18.0 mmol) was added to ethanol (50 mL) at 20° C. and the mixture stirred until the metal had fully reacted. Triethyl phosphonoacetate (2.4 mL, 12.0 mmol) was added, the mixture stirred for 5 min., then (E) 1-{4'-[3-(tert-butyldimethylsilanyloxy)-1-methylpropenyl]-biphenyl-4-yl}ethanone (1.14 g, 3.0 mmol) was added to the stirred solution. The mixture was stirred at room temperature for 24 h. The reaction mixture was added water and the product extracted with ethyl acetate (2×). The combined organic phases were washed with brine, dried (MgSO$_4$), filtered and concentrated in vacuo. The residue was submitted to column chromatography on silica gel, using heptane/ethyl acetate (4:1) as eluent, to give 1.13 g (81%) of (E)(E) 3-(4'-{3-[(tert-butyldimethylsilanyl)-methoxy]-1-methyl-propenyl}-biphenyl-4-yl)-but-2-enoic acid ethyl ester.

$^1$H NMR (CDCl$_3$) δ: 0.12 (6H, s), 0.92 (9H, s), 1.32 (3H, t), 2.08 (3H, s), 2.62 (3H, s), 4.22 (2H, q), 4.42 (2H, d), 5.97 (1H, dt), 6.20 (1H, d), 7.43–7.63 (8H, m).

Step F:

A 1M solution of DIBAL-H in toluene (7.3 mL, 7.3 mmol) was, under a atmosphere of nitrogen, added dropwise at −70° C. over 20 min. to a stirred solution of (E)(E) 3-(4'-{3-[(tert-butyldimethylsilanyl)-methoxy]-1-methyl-propenyl}-biphenyl-4-yl)-but-2-enoic acid ethyl ester (1.13 g, 2.43 mmol) in dry THF (25 mL). The mixture was stirred for 30 min. followed by 2 h at room temperature. Ethanol (1 mL) was carefully added, followed by 1N HCl (50 mL) and the resulting mixture extracted with ethyl acetate (2×50 mL). The combined organic extracts were washed with brine, dried (MgSO$_4$), and evaporated to give 1.02 g (99%) of (E)(E) 3-(4'-{3-[(tert-butyldimethylsilanyl)-methoxy]-1-methylpropenyl}-biphenyl-4-yl)-but-2-en-1-ol.

$^1$H NMR (CDCl$_3$) δ: 0.13 (6H, s), 0.96 (9H, s), 1.57 (1H, s), 2.07 (3H, s), 2.13 (3H, s), 4.37–4.46 (4H, m), 5.85 (1H, t), 5.93 (1H, t), 7.46–7.52 (4H, m), 7.53–7.61 (4H, m).

Step G:

Under a atmosphere of nitrogen, azodicarboxylic dipiperidide (0.91 g, 3.62 mmol) was added at 0–5° C. to a stirred solution of tributylphosphine (0.89 mL, 3.62 mmol), (S)-ethyl 2-ethoxy-3-(4-hydroxyphenyl)-propionate (0.60 g, 2.53 mmol) and (E)(E) 3-(4'-{3-[(tert-butyidimethylsilanyl)-methoxy]-1-methylpropenyl}-biphenyl-4-yl)-but-2-en-1-ol (1.02 g, 2.41 mmol) in dry THF (15 ml). The mixture was warmed to room temperature, and stirred for 18 h. The resulting mixture was diluted with water and ethyl acetate, the aqueous layer collected and further extracted with ethyl acetate. The organic layers were combined, washed with brine, dried (MgSO$_4$) and evaporated. The crude product was then purified by column chromatography on silica using heptane/ethyl acetate (4:1) as eluent to give 1.18 g (76%) of (E)(E)(S) 3-{4-[3-(4'-{3-[(tert-butyldimethylsilanyl)-methoxy]-1-methylpropenyl}-biphenyl-4-yl)-but-2-enyloxy]-phenyl}-2-ethoxy-propionic acid ethyl ester.

$^1$H NMR (CDCl$_3$) δ: 0.13 (6H, s), 0.93 (9H, s), 1.18 (3H, t), 1.23 (3H, t), 2.07 (3H, s), 2.18 (3H, s), 2.95 (2H, d), 3.31–3.42 (1H, m), 3.55–3.67 (1H, m), 3.98 (1H, t), 4.17 (2H, q), 4.42 (2H, d), 4.73 (2H, d), 5.95 (1H, t), 6.12 (1H, t), 6.88 (2H, d), 7.18 (2H, d), 7.45–7.60 (8H, m).

Step H:

A solution of E)(E)(S) 3-{4-[3-(4'-{3-[(tert-butyidimethylsilanyl)-methoxy]-1-methylpropenyl}-biphenyl-4-yl)-but-2-enyloxy]-phenyl}-2-ethoxy-propionic acid ethyl ester (1.18 g, 1.84 mmol) in dry THF was cooled on ice and slowly added a 1.1M solution of tetrabutylammonium fluoride in THF (1.93 mL, 1.93 mmol). The reaction mixture was stirred at room temperature for 3 h. The mixture was diluted with water and ethyl acetate, the aqueous layer collected and further extracted with ethyl acetate. The organic layers were combined, washed with brine, dried (MgSO$_4$) and evaporated to give 0.94 g of (E)(E)(S) 2-ethoxy-3-(4-{3-[4'-{3-hydroxy-1-methyl-propenyl)-biphenyl-4-yl]-but-2-enyloxy}-phenyl)-propionic acid ethyl ester.

$^1$H NMR (CDCl$_3$) δ: 1.18 (3H, t), 1.22 (3H, t), 2.12 (3H, s), 2.18 (3H, s), 2.96 (2H, d), 3.30–3.42 (1H, m), 3.53–3.67 (1H, m), 3.98 (1H, t), 4.17 (2H, q), 4.40 (2H, d), 4.74 (2H, d), 6.04 (1H, t), 6.12 (1H, t), 6.88 (2H, d), 7.18 (2H, d), 7.45–7.62 (8H, m).

Step I:

Under a atmosphere of nitrogen, azodicarboxylic dipiperidide (0.50 g, 1.89 mmol) was added at 0–5° C. to a stirred solution of tributylphosphine (0.37 mL, 1.89 mmol), (S)-ethyl 2-ethoxy-3-(4-hydroxyphenyl)-propionate (0.32 g, 1.32 mmol) and (E)(E)(S) 2-ethoxy-3-(4-{3-[4'-{3-hydroxy-1-methyl-propenyl)-biphenyl-4-yl]-but-2-enyloxy}-phenyl)-propionic acid ethyl ester (0.65 g, 1.26 mmol) in dry THF (15 ml). The mixture was warmed to room temperature, and stirred for 18 h. The resulting mixture was diluted with water and ethyl acetate, the aqueous layer collected and further extracted with ethyl acetate. The organic layers were combined, washed with brine, dried (MgSO$_4$) and evaporated to give 580 mg (63%) of the title compound.

$^1$H NMR (CDCl$_3$) δ: 1.17 (6H, t), 1.22 (6H, t), 2.16 (6H, s), 2.97 (4H, d), 3.27–3.43 (2H, m), 3.52–3.69 (2H, m), 3.98 (2H, t), 4.17 (4H, q), 4.73 (4H, d), 6.12 (2H, t), 6.88 (4H, d), 7.18 (4H, d), 7.43–7.63 (8H, m).

Example 12

General Procedure E (E)(E)(S)(S) 3-{4-[3-(4'-{3-[4-(2-Carboxy-2-ethoxy-ethyl)-phenoxy]-1-methyl-propenyl}-biphenyl-4-yl)-but-2-enyloxy]-phenyl}-2-ethoxy-propionic acid

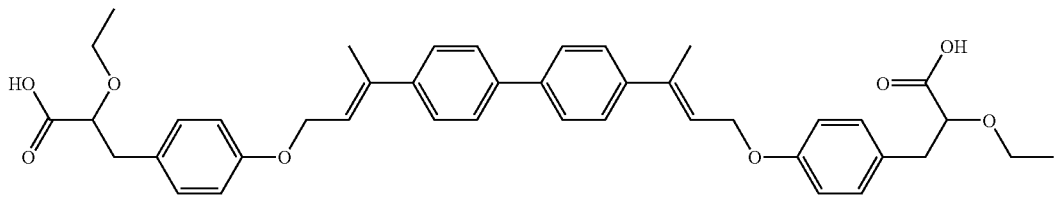

Step A:

To a solution of (E)(E)(S)(S) 2-ethoxy-3-{4-[3-(4'-{3-[4-(2-ethoxy-2-ethoxycarbonyl-ethyl)-phenoxy]-1-methyl-propenyl}-biphenyl-4-yl)-but-2-enyloxy]-phenyl}-propionic acid ethyl ester (example 11) (367 mg 0.5 mmol) in ethanol (10 mL) was added 1N sodium hydroxide (2 mL). The reaction mixture was stirred at room temperature for 18 h, and at 60° C. 1 h. The resulting mixture was diluted with water and ethyl acetate, the aqueous layer collected and further extracted with ethyl acetate (3×). The organic layers were combined, washed with brine, dried (MgSO$_4$) and evaporated to give 180 mg (53%) of the title compound.

$^1$H NMR (CDCl$_3$+1 dr. DMSO): δ 1.15 (6H, t), 2.93 (2H, dd), 3.04 (2H, dd), 3.30–3.42 (2H, m), 3.60–3.71 (2H, m), 3.95 (2H, dd), 4.73 (4H, d), 6.11 (2H, t), 6.88 (4H, d), 7.21 (4H, d), 7.51 (4H, d), 7.57 (4H, d).

Example 13

General Procedure A (E)(E)(S)(S) 2-Ethoxy-3-(4-[5-(7-{5-[4-(2-ethoxy-2-ethoxycarbonyl-ethyl)-phenoxy]-3-methyl-pent-3-en-1-ynyl}-9-oxo-9H-fluoren-2-yl)-3-methyl-pent-2-en-4-ynyloxy]-phenyl}-propionic acid ethyl ester

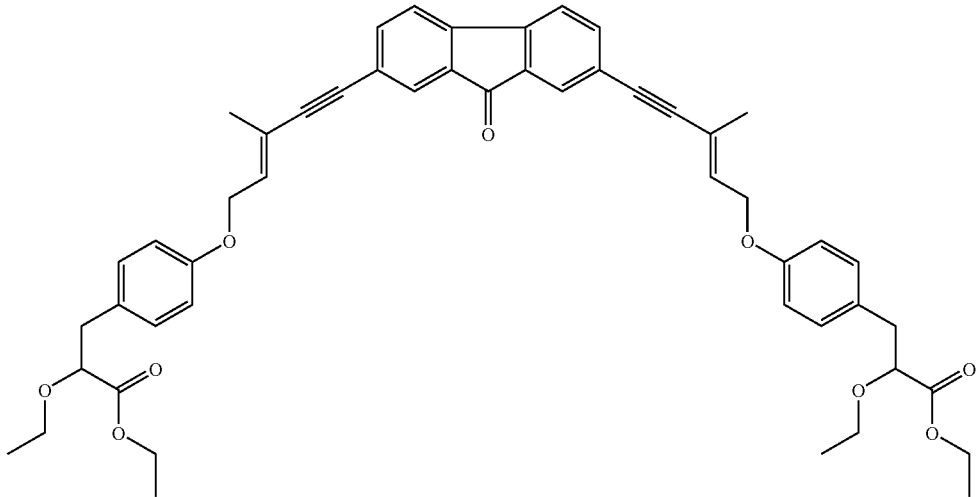

Step A-B:

To a solution of 2,7-dibromo-9-fluorenone (338 mg, 1.0 mmol) in dry THF (17 mL) under a nitrogen atmosphere were added copper(I) iodide (30 mg, 0.16 mmol) and dichlorobis(triphenylphosphine)palladium (II) (70 mg, 0.10 mmol), trans-3-methyl-2-penten-4-yn-1-ol (481 mg, 5.0 mmol) and dry isopropylamine (17 mL). After stirring at room temperature for 6 h, the reaction mixture was filtered and the filtrate evaporated to dryness. The product was purified by column chromatography on silica using dichloromethane/THF (10:1) as eluent to give 200 mg (71%) of (E)(E) 2,7-bis-(5-hydroxy-3-methyl-pent-3-en-1-ynyl)-fluoren-9-one.

$^1$H NMR (DMSO): δ 1.87 (6H, s), 4.10 (4H, t), 4.83 (2H, t), 6.05 (2H, dt), 7.57 (2H, s), 7.66 (2H, d), 7.82 (2H, d).

Step C:

To a solution of (E)(E) 2,7-bis-(5-hydroxy-3-methyl-pent-3-en-1-ynyl)-fluoren-9-one (179 mg, 0.49 mmol) in dry THF (10 mL) was under a atmosphere of nitrogen added triphenylphosphine (385 mg, 1.47 mmol) and (S)-2-ethoxy-3-(4-hydroxyphenyl)-propionic acid ethyl ester (467 mg, 1.96 mmol) and the mixture was cooled on ice. After stirring for 10 min. diethylazodicarboxylate (227 mg, 0.256 mmol) was added. After stirring for 1 h the reaction mixture was added water and dichloromethane. The aqueous layer was further extracted with dichloromethane (2×). The combined organic phases were dried (MgSO$_4$), filtered and evaporated. The product was purified by column chromatography using dichloromethane/THF (10:1) as eluent to give 220 mg (55%) of the title compound.

$^1$H NMR (CDCL$_3$): δ 1.17 (6H, t), 1.22 (6H, t), 1.98 (6H, s), 2.95 (4H, d), 3.30–3.40 (2H, m), 3.54–3.65 (2H, m), 3.98 (2H, t), 4.18 (4H, q), 4.62 (4H, d), 6.20 (2H, t), 6.85 (4H, d), 7.17 (4H, d), 7.43 (2H, d), 7.52 (2H, d), 7.68 (2H, s).

Example 14

General Procedure E (E)(E)(S)(S) 3-{4-[5-(7-{5-[4-(2-Carboxy-2-ethoxy-ethyl)-phenoxy]-3-methyl-pent-3-en-1-ynyl}-9-oxo-9H-fluoren-2-yl)-3-methyl-pent-2-en-4-ynyloxy]-phenyl}-2-ethoxy-propionic acid

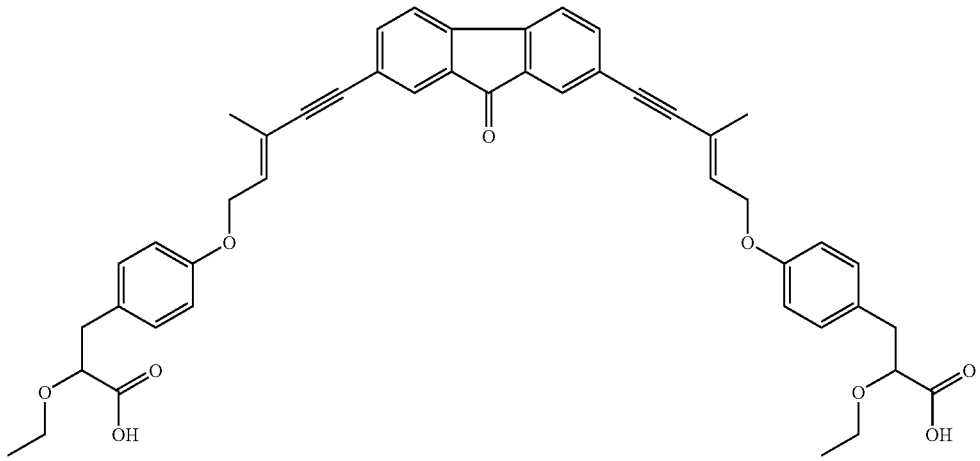

Step A:

To a solution of (E)(E)(S)(S) 2-ethoxy-3-{4-[5-(7-{5-[4-(2-ethoxy-2-ethoxycarbonyl-ethyl)-phenoxy]-3-methyl-pent-3-en-1-ynyl}-9-oxo-9H-fluoren-2-yl)-3-methyl-pent-2-en-4-ynyloxy]-phenyl}-propionic acid ethyl ester (example 13) (185 mg, 0.23 mmol) in ethanol (10 mL) was added 1N sodium hydroxide (2.3 mL). After stirring at 60° C. for 30 min., the reaction mixture was concentrated in vacuo, added water and 1N hydrochloride acid to pH 1. The product was extracted with dichloromethane (×3) and the combined organic phases were dried (MgSO$_4$), filtered and concentrated in vacuo to give 160 mg of the title compound as a crystalline product.

$^1$H NMR (CDCl$_3$): δ 1.18 (6H, t), 1.98 (6H, s), 2.97 (2H, dd), 3.10 (2H, dd), 3.38–3.51 (2H, m), 3.57–3.69 (2H, m), 4.05 (2H, dd), 4.63 (4H, d), 6.17 (2H, t), 6.85 (4H, d), 7.15 (4H, d), 7.41 (2H, d), 7.52 (2H, d), 7.65 (2H, s).

Example 15

General Procedure A

[4-(3-{3-[3-(4-Methoxycarbonylmethyl-phenoxy)-prop-1-ynyl]-phenyl}-prop-2-ynyloxy)-phenyl]-acetic acid methyl ester

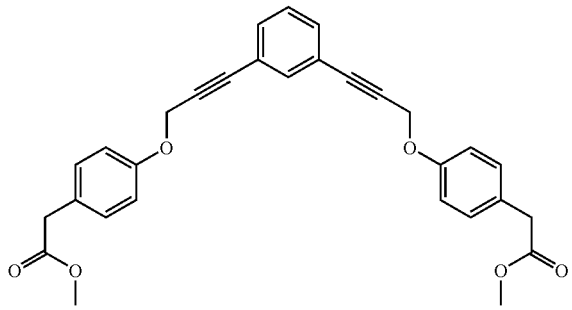

Step C:

Under a atmosphere of nitrogen, azodicarboxylic dipiperidide (406 mg, 1.61 mmol) was added at 0–5° C. to a stirred solution of tributylphosphine (325 mg, 1.61 mmol), methyl 4-hydroxyphenylacetate (268 mg, 1.61 mmol) and 3-[3-(3-hydroxy-prop-1-ynyl)-phenyl]-prop-2-yn-1-ol (*J Pharmacol Exp Ther* 298: 1260–1268, 2001) (150 mg, 0.81 mmol) in dry THF (20 mL). The reaction mixture was stirred for 1 h at 0–5° C., and at room temperature for 16 h. The reaction mixture was concentrated in vacuo. The crude product was purified by flash chromatography using heptane/ethyl acetate (1:1) as eluent to give 218 mg (56%) of the title compound.

$^1$H NMR (DMSO): δ 3.35 (6H, s), 3.53 (4H, s), 5.03 (4H, s), 6.93 (2H, d), 7.22 (2H, d), 7.40 (2H, dd), 7.45–7.50 (3H, m).

Example 16

General Procedure E

[4-(3-{3-[3-(4-Methoxycarbonylmethyl-phenoxy)-prop-1-ynyl]-phenyl}-prop-2-ynyloxy)-phenyl]-acetic acid

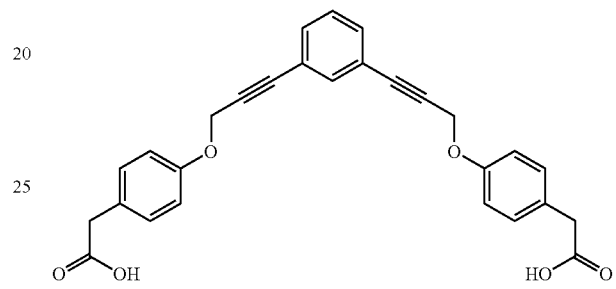

Step A:

To a solution of [4-(3-{3-[3-(4-methoxycarbonylmethyl-phenoxy)-prop-1-ynyl]-phenyl}-prop-2-ynyloxy)-phenyl]-acetic acid methyl ester (example 15) (200 mg, 0.42 mmol) in ethanol (3 mL) was added 1N sodium hydroxide (1.6 mmol, 1.6 mL). After stirring at room temperature for 16 h, the reaction mixture was added 1N hydrochloride acid to pH 1. The product was isolated by filtration and dried to give 100 mg (53%) of the title compound as a crystalline product.

$^1$H NMR (acetone-d$_6$): δ 3.55 (4H, s), 5.00 (4H, s), 7.00 (4H, d), 7.27 (4H, d), 7.38 (1H, dd), 7.43 (1H, s), 7.48 (2H, dd).

Example 17

General Procedure A (E)(E) [4-(5-{4-[5-(4-Methoxycarbonylmethoxy-3-methyl-phenoxy)-pent-3-en-1-ynyl]-phenyl}-pent-2-en-4-ynyloxy)-2-methyl-phenoxy]-acetic acid methyl ester

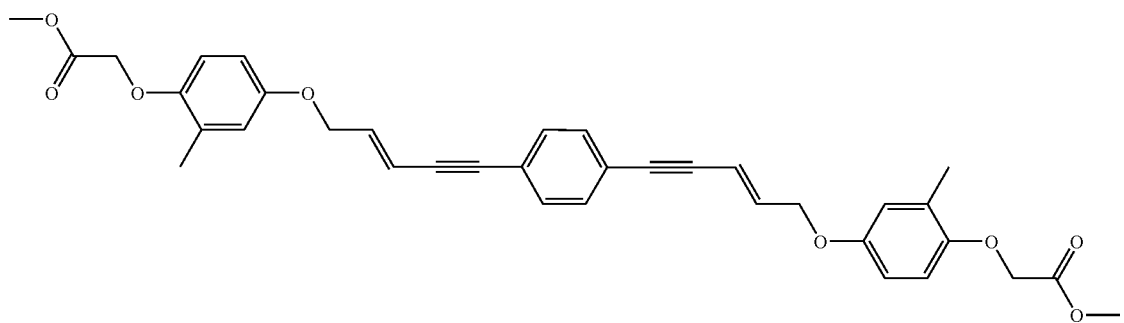

Step C:

Under a atmosphere of nitrogen, azodicarboxylic dipiperidine (252 mg, 1.0 mmol) was added at room temperature to a stirred solution of tributylphosphine (202 mg, 1.0 mmol), (4-hydroxy-2-methyl-phenoxy)-acetic acid methyl ester (WO 01/00603 A1)(170 mg, 0.86 mmol) and (E)(E) 5-[4-(5-hydroxy-pent-3-en-1-ynyl)-phenyl]-pent-2-en-4-yn-1-ol (example 1, Step A-B) (103 mg, 0.43 mmol) in dry THF (20 mL). After 2 h the reaction mixture was added water and the product extracted with ethyl acetate. The combined organic phases were dried, filtered and concentrated in vacuo. The crude product was purified by flash chromatography using heptane graduated to heptane/ethyl acetate (1:1) as eluent to give 10 mg of the title compound.

$^1$H NMR (CDCL$_3$): δ 2.28 (6H, s), 3.78 (6H, s), 4.54–4.60 (4H, m), 4.60 (4H, s), 6.03 (2H, dt), 6.38 (2H, dt), 6.66 (4H, s), 6.78 (2H, s), 7.37 (4H, s).

Example 18

General Procedure E (E)(E) [4-(5-{4-[5-(4-Methoxycarbonylmethoxy-3-methyl-phenoxy)-pent-3-en-1-ynyl]-phenyl}-pent-2-en-4-ynyloxy)-2-methyl-phenoxy]-acetic acid

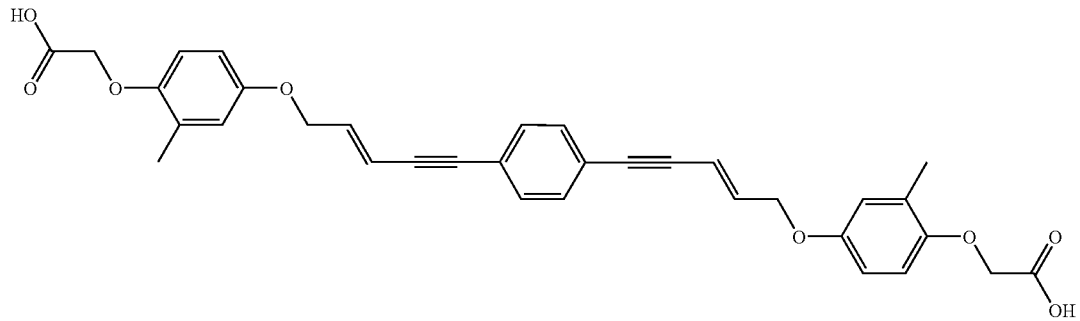

Step A:

To a solution of (E)(E) [4-(5-{4-[5-(4-methoxycarbonyl-methoxy-3-methyl-phenoxy)-pent-3-en-1-ynyl]-phenyl}-pent-2-en-4-ynyloxy)-2-methyl-phenoxy]-acetic acid methyl ester (example 17) (15 mg, 0.025 mmol) in ethanol (15 mL) and THF (5 mL) was added 1N sodium hydroxide (1.0 mL). After stirring at room temperature for 30 min., the reaction mixture was added water and 1N hydrochloride acid to pH 1. The product was extracted with dichloromethane (×3) and the combined organic phases were dried (MgSO$_4$), filtered and concentrated in vacuo to give 10 mg of the title compound.

Example 19

General Procedure A (E)(E)(S)(S) 3-{3-Bromo-4-[5-(4-{5-[2-bromo-4-(2-ethoxy-2-ethoxycarbonyl-ethyl)-phenoxy]-pent-3-en-1-ynyl}-phenyl)-pent-2-en-4-ynyloxy]-phenyl}-2-ethoxy-propionic acid ethyl ester

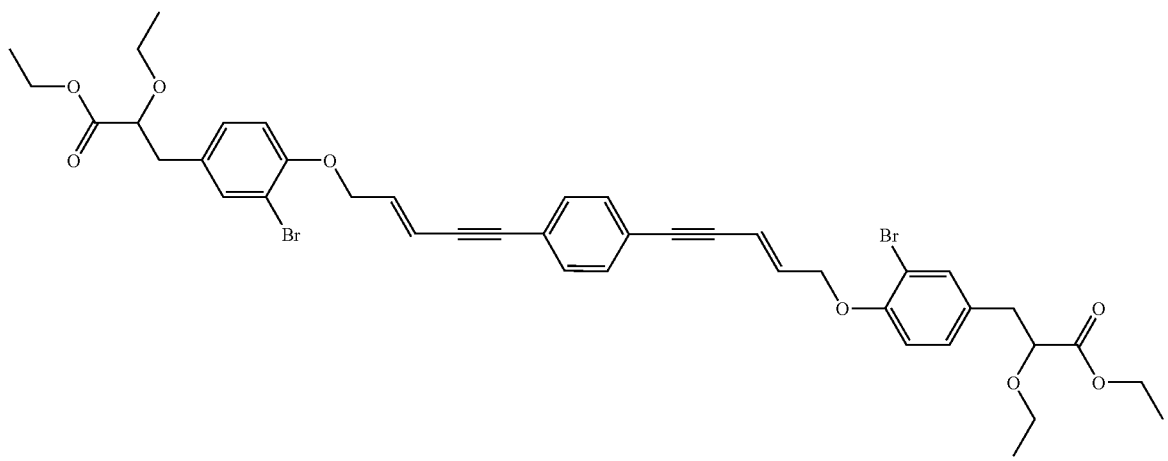

Step C:
a) To a stirred solution of (S)-2-ethoxy-3-(4-hydroxyphenyl)-propionic acid ethyl ester (*Tetrahedron Letters*, Vol. 35, No 19, 3139–3142, 1994) (9.5 g, 40 mmol) in dry methylene chloride (100 ml) was over 1 h dropwise added a solution of bromine in methylene chloride (40 ml) at room temperature. The reaction was stirred for 60 min, washed with saturated sodium sulfite and brine. The organic phase was dried (MgSO$_4$) and evaporated. The residue was purified by column chromatography using heptane:ethyl acetate (9:1) as eluent to give 11.25 g (88%) of (S)-3-(3-bromo-4-hydroxyphenyl)-2-ethoxy-propionic acid ethyl ester.

$^1$H NMR (CDCL$_3$): δ 1.18 (3H, t), 1.23 (3H, t), 2.92 (2H, d), 3.30–3.43 (1H, m), 3.57–3.70 (1H, m), 3.96 (1H, dd), 4.18 (4H, q), 5.72 (1H, s), 6.90 (1H, d), 7.09 (1H, dd), 7.35 (1H, d).

b) Under a atmosphere of nitrogen, azodicarboxylic dipiperidide (504 mg, 2.0 mmol) was added to a stirred solution of tributylphosphine (325 mg, 1.3 mmol), (S)-3-(3-bromo-4-hydroxy-phenyl)-2-ethoxy-propionic acid ethyl ester (450 mg, 1.89 mmol) and (E)(E) 5-[4-(5-hydroxy-pent-3-en-1-ynyl)-phenyl]-pent-2-en-4-yn-1-ol (example 1, step A-B) (150 mg, 0.63 mmol) in dry THF (30 mL). After 1 h the reaction mixture was added water and the product extracted with ethyl acetate (3×). The combined organic phases were dried, filtered and concentrated in vacuo The crude product was purified by flash chromatography using heptane/ethyl acetate (4:1) as eluent to give 250 mg of the title compound.

$^1$H NMR (CDCL$_3$): δ 1.18 (6H, t), 1.23 (6H, t), 2.95 (4H, m), 3.30–3.43 (2H, m), 3.55–3.67 (2H, m), 3.98 (2H, t), 4.18 (4H, q), 4.63 (4H, dd), 6.07 (2H, dt), 6.39 (2H, dt), 6.80 (2H, d), 7.13 (2H, dd), 7.38 (4H, s), 7.45 (2H, dd).

Example 20

General Procedure E (E)(E)(S)(S) 3-{3-Bromo-4-[5-(4-{5-[2-bromo-4-(2-ethoxy-2-ethoxycarbonyl-ethyl)-phenoxy]-pent-3-en-1-ynyl}-phenyl)-pent-2-en-4-ynyloxy]-phenyl}-2-ethoxy-propionic acid

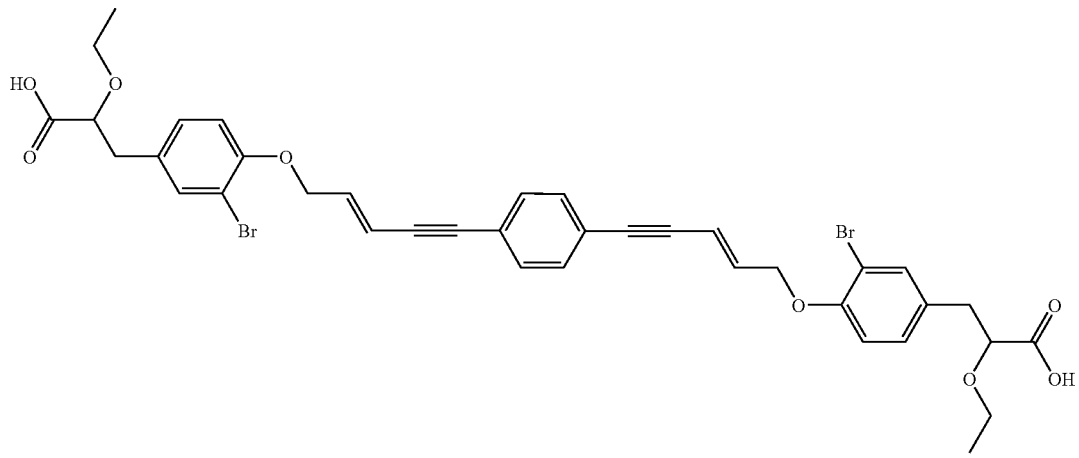

Step A:
To a solution of (E)(E)(S)(S) 3-{3-bromo-4-[5-(4-{5-[2-bromo-4-(2-ethoxy-2-ethoxycarbonyl-ethyl)-phenoxy]-pent-3-en-1-ynyl}-phenyl)-pent-2-en-4-ynyloxy]-phenyl}-2-ethoxy-propionic acid ethyl ester (example 19) (250 mg 0.30 mmol) in THF (2 mL) and ethanol (3 mL) was added 1N sodium hydroxide (3 mL). After stirring at room temperature for 1 h, the reaction mixture was concentrated in vacuo, added water and 1N hydrochloride acid to pH 1. The product was extracted with ethyl acetate (×3) and the combined organic phases were washed with water, dried (MgSO$_4$), filtered and concentrated in vacuo to give 230 mg of the title compound.

$^1$H NMR (CDCl$_3$): δ 1.18 (6H, t), 2.93 (2H, dd), 3.04 (2H, dd), 3.35–3.48 (2H, m), 3.58–3.72 (2H, m), 4.03 (2H, dd), 4.68 (4H, dd), 6.18 (2H, dt), 6.39 (2H, dt), 6.80 (2H, d), 7.15 (2H, dd), 7.39 (4H, s), 7.49 (2H, d), 10.24 (2H, bs).

Example 21

General Procedure A (E)(E) [3-(5-{4-[5-(3-Ethoxycarbonylmethyl-phenoxy)-pent-3-en-1-ynyl]-phenyl}-pent-2-en-4-ynyloxy)-phenyl]-acetic acid ethyl ester

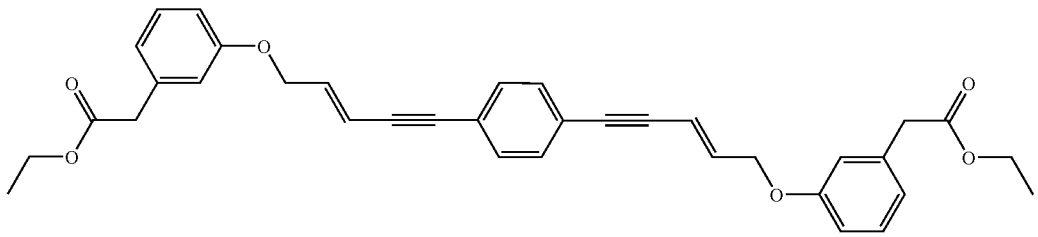

Step C:

Under an atmosphere of nitrogen, azodicarboxylic dipiperidide (325 mg, 1.3 mmol) was added to a stirred solution of (3-hydroxyphenyl)-acetic acid ethyl ester (340 mg, 1.89 mmol), (E)(E) 5-[4-(5-hydroxy-pent-3-en-1-ynyl)-phenyl]-pent-2-en-4-yn-1-ol (example 1, step A-B)(150 mg, 0.63 mmol) and tributylphosphine (365 mg, 1.3 mmol) in dry THF (30 mL). After 1 h the reaction mixture was added water and the product extracted with ethyl acetate (3×). The combined organic phases were washed with water, dried (MgSO$_4$), filtered and concentrated in vacuo. The crude product was purified by flash chromatography using heptane/ethyl acetate (4:1) as eluent to give 200 mg of the title compound.

$^1$H NMR (CDCL$_3$): δ 1.23 (6H, t), 3.55 (4H, s), 4.15 (4H, q), 4.62 (4H, dd), 6.05 (2H, dt), 6.38 (2H, dt), 6.78–6.92 (6H, m), 7.20–7.25 (2H, m), 7.37 (4H, s).

Example 22

General Procedure E (E)(E) [3-(5-{4-[5-(3-Ethoxycarbonylmethyl-phenoxy)-pent-3-en-1-ynyl]-phenyl}-pent-2-en-4-ynyloxy)-phenyl]-acetic acid

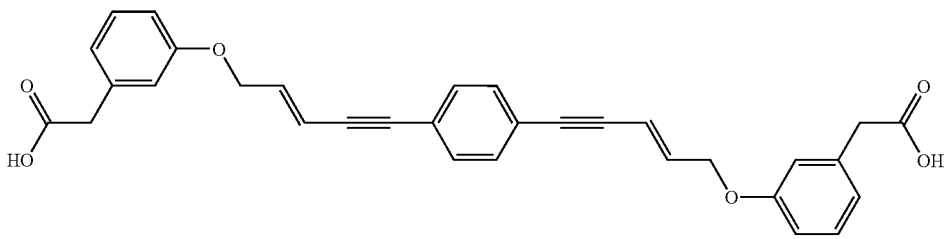

Step A:

To a solution of (E)(E) [3-(5-{4-[5-(3-ethoxycarbonylmethyl-phenoxy)-pent-3-en-1-ynyl]-phenyl}-pent-2-en-4-ynyloxy)-phenyl]-acetic acid ethyl ester (example 21) (200 mg, 0.35 mmol) in THF (2 mL) and ethanol (6 mL) was added 1N sodium hydroxide (1 mL). After stirring at room temperature for 3 h, the reaction mixture was added 1N hydrochloride acid and ethyl acetate. The title compound was isolated by filtration of the mixture in 50 mg yield.

$^1$H NMR (DMSO-d$_6$): δ 3.53 (4H, s), 4.69 (4H, d), 6.16 (2H, d), 6.44 (2H, dt), 6.80–6.92 (6H, m), 7.23 (2H, t), 7.45 (4H, s).

Example 23

General Procedure A (E)(E)(S)(S) 2-Ethoxy-3-{4-[5-(4'-{5-[4-(2-ethoxy-2-ethoxycarbonylethyl)-phenoxy]-3-methyl-pent-3-en-1-ynyl}-biphenyl-4-yl)-3-methyl-pent-2-en-4-ynyloxy]-phenyl}-propionic acid ethyl ester

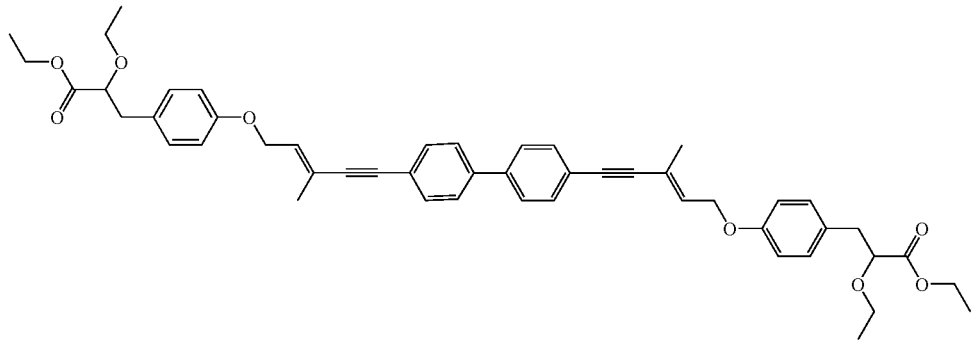

Step A-B:

To a solution of 4,4'-diiodobiphenyl (1.22 g, 3.0 mmol) in diisopropylamine (12 mL) under a nitrogen atmosphere were added copper(I) iodide (30 mg, 0.15 mmol) and tetrakis(triphenylphosphine)palladium (30 mg, 0.03 mmol). After stirring for 1 h, a solution of trans-3-methyl-2-pentene-4-yn-1-ol (1.15 g, 12.0 mmol) in diisopropylamine (6 mL) was added. After stirring at 60° C. for 8 h, the reaction mixture was filtered and the filtrate evaporated to dryness. The product was purified by flash chromatography using dichloromethane/THF (20:1) as eluent to give 603 mg (59%) of (E)(E) 5-[4'-(5-hydroxy-3-methyl-pent-3-en-1-ynyl)-biphenyl-4-yl]-3-methyl-pent-2-en-4-yn-1-ol.

$^1$H NMR (DMSO-$d_6$): δ 1.87 (6H, s), 4.10 (4H, t), 4.80 (2H, t), 6.01 (2H, t), 7.53 (4H, d), 7.73 (4H, d).

added water and the product extracted with dichloromethane (2×). The combined organic phases were dried (MgSO$_4$), filtered and concentrated in vacuo. The crude product was purified by flash chromatography using dichloromethane/THF (40:1) as eluent to give 213 mg (56%) of the title compound.

$^1$H NMR (CDCL$_3$): δ 1.17 (6H, t), 1.22 (6H, t), 2.00 (6H, s), 2.97 (4H, d), 3.30–3.41 (2H, m), 3.55–3.67 (2H, m), 3.97 (2H, t), 4.15 (4H, q), 4.63 (4H, d), 6.18 (2H, dt), 6.85 (4H, d), 7.17 (4H, d), 7.49 (4H, d), 7.57 (4H, d).

Example 24

General Procedure E (E)(E)(S)(S) 2-Ethoxy-3-{4-[5-(4'-{5-[4-(2-ethoxy-2-ethoxycarbonylethyl)-phenoxy]-3-methyl-pent-3-en-1-ynyl}-biphenyl-4-yl)-3-methyl-pent-2-en-4-ynyloxy]-phenyl}-propionic acid

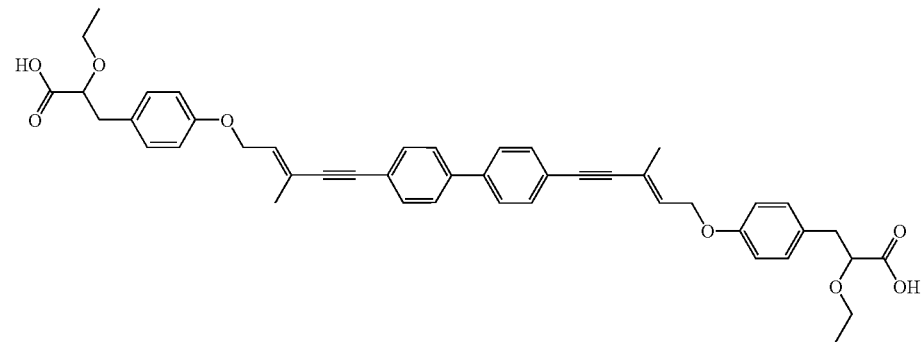

Step C:

Under a atmosphere of nitrogen, diethyl azodicarboxylate (261 mg, 1.5 mmol) was added at 0–50° C. to a stirred solution of (S)-2-ethoxy-3-(4-hydroxyphenyl)-propionic acid ethyl ester (*Tetrahedron Letters*, Vol. 35, No 19, 3139–3142, 1994)(476 mg, 2.0 mmol), (E)(E) 5-[4'-(5-hydroxy-3-methyl-pent-3-en-1-ynyl)-biphenyl-4-yl]-3-methyl-pent-2-en-4-yn-1-ol (171 mg, 0.50 mmol) and triphenylphosphine (393 mg, 1.5 mmol), in dry THF (10 mL). After stirring at 0–5° C. for 1 h, the reaction mixture was Step A:

To a solution of (E)(E)(S)(S) 2-ethoxy-3-{4-[5-(4'-{5-[4-(2-ethoxy-2-ethoxy-carbonylethyl)-phenoxy]-3-methyl-pent-3-en-1-ynyl}-biphenyl-4-yl)-3-methyl-pent-2-en-4-ynyloxy]-phenyl}-propionic acid ethyl ester (example 23) (210 mg 0.27 mmol) in ethanol (10 mL) was added 1N sodium hydroxide (2.7 mL). After stirring at 60° C. for 30 min, the reaction mixture was concentrated in vacuo and added 1N hydrochloride acid. The product was extracted with dichloromethane (×3). The combined organic phases were dried (MgSO$_4$), filtered and concentrated in vacuo to give 170 mg (87%) of the title compound.

$^1$H NMR (CDCl$_3$): δ 1.19 (6H, t), 2.00 (6H, s), 2.97 (2H, dd), 3.08 (2H, dd), 3.39–3.50 (2H, m), 3.55–3.68 (2H, m), 4.05 (2H, dd), 4.63 (4H, d), 6.20 (2H, dt), 6.85 (4H, d), 7.18 (4H, d), 7.48 (4H, d), 7.53 (4H, d).

Example 25

General Procedure A (E)(E)(S)(S) 2-Ethoxy-3-{4-[5-(4-{5-[4-(2-ethoxy-2-ethoxycarbonylethyl)-phenoxy]-3-methyl-pent-3-en-1-ynyl}-phenyl)-3-methyl-pent-2-en-4-ynyloxy]-phenyl}-propionic acid ethyl ester

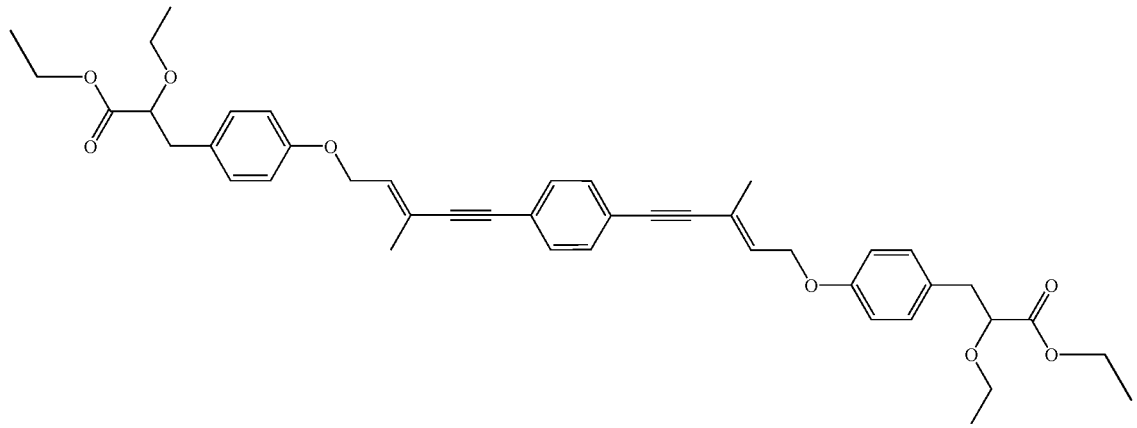

Step A-B:

To a solution of 1,4-diiodobenzene (0.99 g, 3.0 mmol) in diisopropylamine (12 mL) under a nitrogen atmosphere were added copper(I) iodide (30 mg, 0.15 mmol) and tetrakis(triphenylphosphine)palladium (30 mg, 0.03 mmol). After stirring for 1 h, a solution of trans-3-methyl-2-pentene-4-yn-1-ol (1.15 g, 12.0 mmol) in diisopropylamine (6 mL) was added. After stirring at 60° C. for 8 h, the reaction mixture was filtered and the filtrate evaporated to dryness. The product was purified by flash chromatography using dichloromethane/THF (20:1) as eluent to give 500 mg (63%) of (E)(E) 5-[4-(5-hydroxy-3-methyl-pent-3-en-1-ynyl)-phenyl]-3-methyl-pent-2-en-4-yn-1-ol.

$^1$H NMR (DMSO-d$_6$): δ 1.83 (6H, s), 4.08 (4H, t), 4.80 (2H, t), 5.98 (2H, t), 7.42 (4H, s).

Step C:

Under a atmosphere of nitrogen, diethyl azodicarboxylate (261 mg, 1.5 mmol) was added at 0–5° C. to a stirred solution of (S)-2-ethoxy-3-(4-hydroxyphenyl)-propionic acid ethyl ester (*Tetrahedron Letters*, Vol. 35, No 19, 3139–3142, 1994)(476 mg, 2.0 mmol), (E)(E) 5-[4-(5-hydroxy-3-methyl-pent-3-en-1-ynyl)-phenyl]-3-methyl-pent-2-en-4-yn-1-ol (133 mg, 0.50 mmol) and triphenylphosphine (393 mg, 1.5 mmol), in dry THF (10 mL). After stirring at 0–5° C. for 1 h, the reaction mixture was added water and the product extracted with dichloromethane (2×). The combined organic phases were dried (MgSO$_4$), filtered and concentrated in vacuo. The crude product was purified by flash chromatography using dichloromethane/THF (40:1) as eluent to give 290 mg (82%) of the title compound.

$^1$H NMR (CDCL$_3$): δ 1.18 (6H, t), 1.23 (6H, t), 1.97 (6H, s), 2.95 (4H, d), 3.30–3.41 (2H, m), 3.53–3.63 (2H, m), 3.98 (2H, t), 4.17 (4H, q), 4.63 (4H, d), 6.18 (2H, dt), 6.82 (4H, d), 7.15 (4H, d), 7.36 (4H, s).

Example 26

General Procedure E (E)(E)(S)(S) 2-Ethoxy-3-{4-[5-(4-{5-[4-(2-ethoxy-2-ethoxycarbonylethyl)-phenoxy]-3-methyl-pent-3-en-1-ynyl}-phenyl)-3-methyl-pent-2-en-4-ynyloxy]-phenyl}-propionic acid

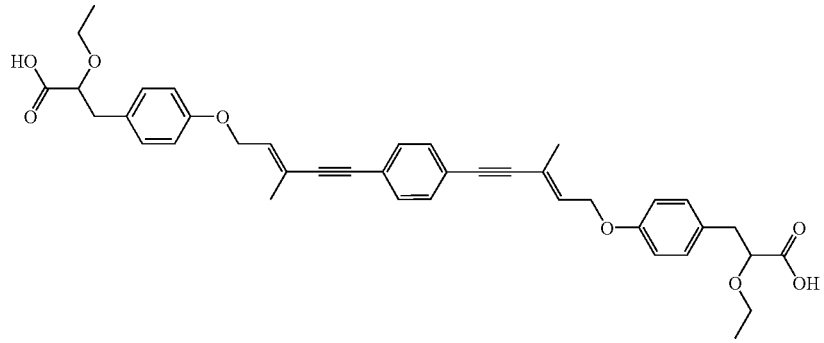

Step A:

To a solution of (E)(E)(S)(S) 2-ethoxy-3-{4-[5-(4-{5-[4-(2-ethoxy-2-ethoxy-carbonylethyl)-phenoxy]-3-methyl-pent-3-en-1-ynyl}-phenyl)-3-methyl-pent-2-en-4-ynyloxy]-phenyl}-propionic acid ethyl ester (example 25) (280 mg 0.40 mmol) in ethanol (10 mL) was added 1N sodium hydroxide (4.0 mL). After stirring at 60° C. for 30 min, the reaction mixture was concentrated in vacuo and added 1N hydrochloride acid. The product was extracted with dichloromethane (×3). The combined organic phases were dried (MgSO$_4$), filtered and concentrated in vacuo to give 241 mg (93%) of the title compound.

$^1$H NMR (CDCl$_3$): δ 1.18 (6H, t), 1.98 (6H, s), 2.95 (2H, dd), 3.07 (2H, dd), 3.37–3.49 (2H, m), 3.57–3.68 (2H, m), 4.04 (2H, dd), 4.62 (4H, d), 6.16 (2H, dt), 6.83 (4H, d), 7.18 (4H, d), 7.36 (4H, s).

Example 27

General Procedure A (E)(E)(S)(S) 2-Ethoxy-3-{4-[5-(3-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid ethyl ester After stirring for 1 h, a solution of trans-3-methyl-2-pentene-4-yn-1-ol (1.15 g, 12.0 mmol) in diisopropylamine (6 mL) was added. After stirring at 60° C. for 8 h, the reaction mixture was filtered and the filtrate evaporated to dryness. The product was purified by flash chromatography using dichloromethane/THF (20:1) as eluent to give 780 mg (99%) of (E)(E) 5-[3-(5-hydroxy-3-methyl-pent-3-en-1-ynyl)-phenyl]-3-methyl-pent-2-en-4-yn-1-ol.

$^1$H NMR (DMSO-d$_6$): δ 1.84 (6H, s), 4.07 (4H, t), 4.82 (2H, t), 6.01 (2H, t), 7.35–7.45 (3H, m), 7.48 (1H, s).

Step C:

Under a atmosphere of nitrogen, diethyl azodicarboxylate (261 mg, 1.5 mmol) was added at 0° C. to a stirred solution of (S)-2-ethoxy-3-(4-hydroxyphenyl)-propionic acid ethyl ester (*Tetrahedron Letters*, Vol. 35, No 19, 3139–3142,1994) (476 mg, 2.0 mmol), (E)(E) 5-[3-(5-hydroxy-3-methyl-pent-3-en-1-ynyl)-phenyl]-3-methyl-pent-2-en-4-yn-1-ol (133 mg, 0.50 mmol) and triphenylphosphine (393 mg, 1.5 mmol), in dry THF (10 mL). After stirring at 0° C. for 1 h, the reaction mixture was added water and the product extracted with dichloromethane (2×). The combined organic phases were dried (MgSO$_4$), filtered and concentrated in vacuo. The crude product was purified by flash chromatography using dichloromethane/THF (40:1) as eluent to give 250 mg (71%) of the title compound.

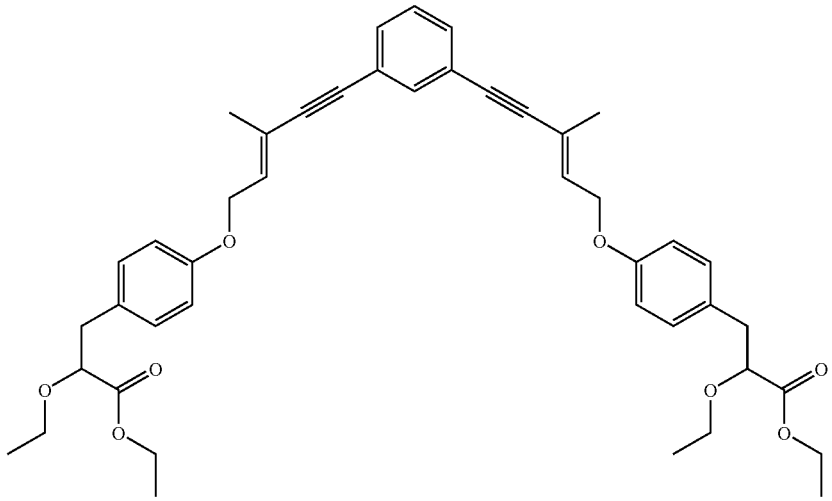

Step A-B:

To a solution of 1,3-diiodobenzene (0.99 g, 3.0 mmol) in diisopropylamine (12 mL) under a nitrogen atmosphere were added copper(I) iodide (30 mg, 0.15 mmol) and tetrakis(triphenylphosphine)palladium (30 mg, 0.03 mmol).

$^1$H NMR (CDCL$_3$): δ 1.18 (6H, t), 1.23 (6H, t), 1.97 (6H, s), 2.95 (4H, d), 3.30–3.41 (2H, m), 3.53–3.63 (2H, m), 3.98 (2H, t), 4.17 (4H, q), 4.63 (4H, d), 6.18 (2H, dt), 6.82 (4H, d), 7.17 (4H, d), 7.20–7.28 (1H, dd), 7.35 (2H, d), 7.52 (1H, s).

Example 28

General Procedure E (E)(E)(S)(S) 2-Ethoxy-3-{4-[5-(3-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid

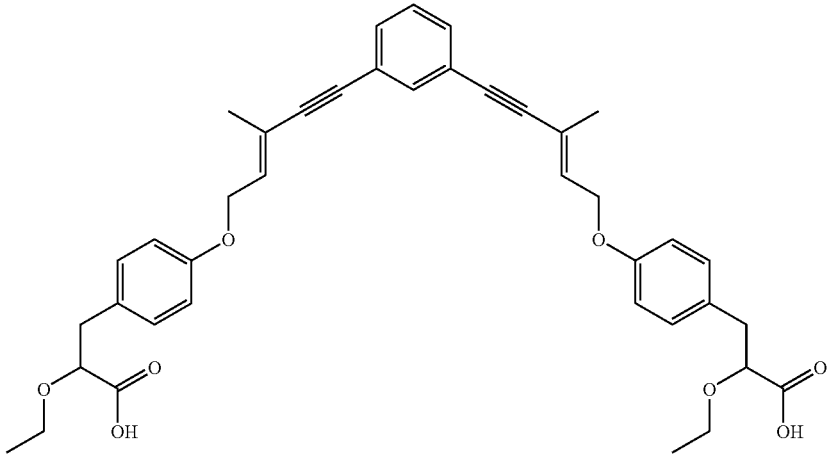

Step A:

To a solution of (E)(E)(S)(S) 2-ethoxy-3-{4-[5-(3-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid ethyl ester (example 27) (255 mg 0.36 mmol) in ethanol (10 mL) was added 1N sodium hydroxide (3.6 mL). After stirring at 60° C. for 30 min, the reaction mixture was concentrated in vacuo and added 1N hydrochloride acid. The product was extracted with dichloromethane (×3). The combined organic phases were dried (MgSO$_4$), filtered and concentrated in vacuo to give 232 mg (99%) of the title compound.

$^1$H NMR (CDCl$_3$): δ 1.18 (6H, t), 1.98 (6H, s), 2.95 (2H, dd), 3.07 (2H, dd), 3.37–3.49 (2H, m), 3.57–3.68 (2H, m), 4.04 (2H, dd), 4.62 (4H, d), 6.16 (2H, dt), 6.83 (4H, d), 7.18 (4H, d), 7.25 (1H, dd), 7.35 (2H, d), 7.50 (1H, s).

Example 29

[4-(3-{7-[3-(4-Methoxycarbonylmethoxy-3-methyl-phenylsulfanyl)-propenyl]-9H-fluoren-2-yl}-allylsulfanyl)-2-methyl-phenoxy]-acetic acid methyl ester

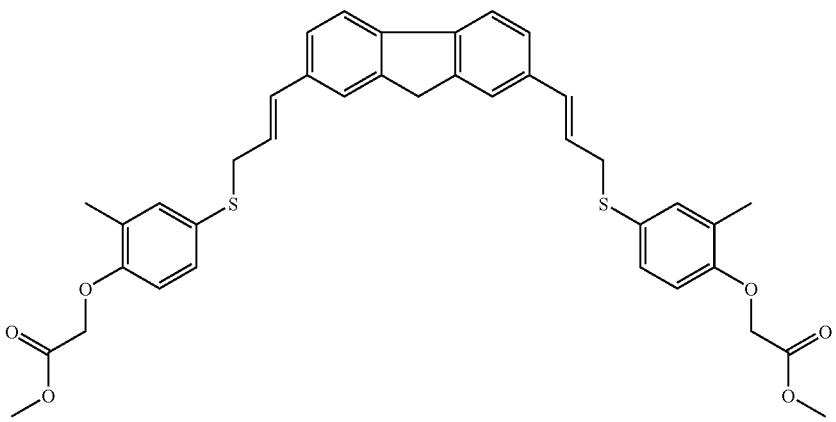

General Procedure G

Step A-B:

A mixture of 2,7-dibromofluorene (Ber. 53, 1236 (1920)) (48.6 g, 0.15 mmol), palladium(II)acetate (1.0 g, 4.45 mmol), triphenylphosphine (3.0 g, 11.4 mmol), triethylamine (30.3 g, 0.3 mol), methyl acrylate (38.7 g, 0.45 mol) and dimethylformamide (150 mL) was stirred and heated at 110° C. for 7 h. The mixture was poured into 1 l water, the resulted solid was filtered off and recrystallized from chloroform to give 36.8 g (74%) of fluorine-2,7-diacrylic acid dimethyl ester. M.p. 206–209° C.

Step C:

A solution of aluminium chloride (19.6 g 0.147 mol) in diethyl ether (150 mL) was added to lithium aluminium hydride (16.6 g, 0.44 mol) in diethyl ether (150 mL) and the mixture was stirred for 30 min. Fluorine-2,7-diacrylic acid dimethyl ester (25.5 g, 76.3 mmol) in THF (1000 mL) was added portionwise to the mixture at 25–50°C. and the stirring was continued for 8 h. 20% NaOH (150 mL) was added dropwise, the suspension was decanted and the organic phase was poured into water (3000 mL). After 3 days in refrigerator 3-[7-(3-hydroxy-propenyl)-9H-fluoren-2-yl-propenol was filtered off and recrystallized from chloroform/methanol yielding 16.5 g (78%) of yellow solid.

$^1$H NMR (250 MHz, DMSO-d$_6$): δ 3.88 (2H, s), 4.13 (4H, t), 4.87 (2H, t), 6.40 (2H, dt), 6.60 (2H, d), 7.40 (2H, d), 7.60 (2H, s), 7.77 (2H, d).

General Procedure A

Step C:

a) o-Cresol (100 g, 0.925 mol) was dissolved in 2-butanone (1200 ml), potassium carbonate (191.7 g, 1.5 mol) and ethyl bromoacetate (162.2 g, 0.971 mol) were added and the mixture was refluxed under stirring for 24 h and then left to stand overnight. The solid was filtered off, the filtrate was evaporated and dissolved in benzene (400 ml). The solution was washed with water (200 ml), 5% solution of sodium carbonate (100 ml) and dried over $MgSO_4$. The residue (cca 200 g) was distilled in vacuo. This afforded 161.9 g (90.1%) of (2-methyl-phenoxy)-acetic acid ethyl ester, b.p. 120–130° C./2 kPa.

b) Chlorosulfonic acid (180.9 g, 104 ml, 1.553 mol) was cooled to −2 −0° C. and then the above (2-methyl-phenoxy)-acetic acid ethyl ester (75.35 g, 0.388 mol) was added dropwise under stirring at such rate that the temperature of the reaction mixture did not exceed 0° C. (20 min). The mixture was left to warm to ambient temperature (1 h) and then poured on crushed ice (1 kg). The crystalline product was filtered off, washed with water (500 ml) and dried on air to constant weight. This gave 108.4 g (95.5%) crude (4-chlorosulfonyl-2-methylphenoxy)-acetic acid ethyl ester. The product was crystallized from cyclohexane (500 ml) affording 73.3 g (64.6%) pure product. M.p. 86–89° C.

$^1$H NMR (300 MHz, $CDCl_3$): δ 7.84 (2H, m), 6.80 (1H, m), 4.76 (2H, s), 4.29 (2H, q), 2.37 (3H, s), 1.31 (3H, s).

c) To the mixture of above (4-chlorosulfonyl-2-methylphenoxy)-acetic acid ethyl ester (97.7 g, 0.333 mol), tin (189.9 g, 1.59 mol) and methanol (170 ml) concentrated hydrochloric acid was added dropwise under vigorous stirring during 20 min. The reaction became exothermic and began to reflux spontaneously. The reaction mixture was further heated to reflux for 3 hours, then cooled and poured to crushed ice (1 kg). The mixture was extracted with diethyl ether (3×200 ml), the ethereal solutions were washed with water (2×80 ml), dried over $MgSO_4$ and evaporated in vacuo. The residue (97.7 g) was dissolved in benzene (300 ml), passed trough column of silica gel (Fluka 60, 800 g) and the column was washed with benzene (2500 ml). Collected benzene solutions were evaporated and the residue was distilled in vacuo. This afforded 41.3 g (58.4%) of (4-mercapto-2-methylphenoxy)-acetic acid methyl ester as oil, b.p. 136.5–137° C./133 Pa.

$^1$H NMR (250 MHz, $CDCl_3$): δ 7.04 (m) +7.04 (m), Σ2H, 6.54 (1H, m), 2.20 (3H, m), 4.56 (2H, s), 3.73 (3H, s), 3.34 (1H, s).

d) The above 3-[7-(3-hydroxy-propenyl)-9H-fluoren-2-yl-propenol (85 mg, 0.3 mmol) and tributylphosphine (242 mg, 1.2 mmol) in dry THF (10 mL) was cooled on ice and under an atmosphere of nitrogen added azodicarboxylic dipiperidine (302 mg, 1.2 mmol). After stirring for 10 min at 0° C., the reaction mixture was slowly added the above (4-mercapto-2-methylphenoxy)-acetic acid methyl ester (255 mg, 1.2 mmol). After stirring at 0° C. for 2 h and at room temperature for 16 h, the reaction mixture was added water (20 mL) and the product extracted with dichloromethane (3×25 mL). The combined organic phases were dried ($MgSO_4$), filtered and concentrated in vacuo. The crude product was purified by flash chromatography using heptane/ethyl acetate (5:2) followed by dichloromethane as eluent to give 34 mg (17%) of the title compound.

$^1$H NMR ($CDCL_3$): δ 2.25 (6H, s), 3.62 (2H, d), 3.79 (6H, s), 3.85 (2H, s), 4.62 (4H, s), 6.25 (2H, dt), 6.37 (2H, d), 6.62 (2H, d), 7.21 (1H, d), 7.25 (2H, s), 7.28 (2H, d), 7.48 (2H, s), 7.63 (2H, d).

PHARMACOLOGICAL METHODS

In vitro PPARalpha, PPARgamma and PPARdelta Activation Activity

The PPAR transient transactivation assays are based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seeded in 96-well plates the day before transfection to give a confluency of 50–80% at transfection. A total of 0,8 µg DNA-containing 0,64 µg pM1α/γLBD, 0,1 µg pCMVβGal, 0,08 µg pGL2(Gal4)$_5$ and 0,02 µg pADVANTAGE was transfected per well using FuGene transfection reagent according to the manufacturers instructions (Roche). Cells were allowed to express protein for 48 h followed by addition of compound.

Plasmids: Human PPAR α,γ and δ was obtained by PCR amplification using cDNA synthesized by reverse transcription of mRNA from human liver, adipose tissue and plancenta respectively. Amplified cDNAs were cloned into pCR2.1 and sequenced. The ligand binding domain (LBD) of each PPAR isoform was generated by PCR (PPARα: aa 167-C-terminus; PPARγ: aa 165-C-terminus; PPARδ: aa 128-C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5×CGGAGTACTGTCCTCCG(AG)) (Webster et al. (1988), Nucleic Acids Res. 16, 8192) into the vector pGL2 promotor (Promega) generating the plasmid pGL2(GAL4)$_5$. pCMVβGal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 µM. Cells were treated with compound for 24 h followed by luciferase assay. Each compound was tested in at least two separate experiments. Luciferase assay: Medium including test compound was aspirated and 100 µl PBS incl. 1 mM Mg++ and Ca++ was added to each well. The luciferase assay was performed using the LucLite kit according to the manufacturers instructions (Packard Instruments). Light emission was quantified by counting on a Packard LumiCounter. To measure β-galactosidase activity 25 µl supernatant from each transfection lysate was transferred to a new microplate. β-galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as means±SD.

What is claimed is:

1. A compound of the general formula (I):

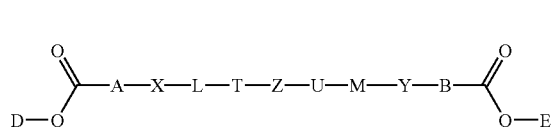

(I)

wherein A is $C_{1-3}$-alkylene which is optionally substituted with one or more substituents selected from
halogen or
$C_{1-3}$-alkyl, $C_{1-6}$-alkoxy, $C_{3-6}$-cycloalkoxy, $C_{1-6}$-alkylthio, $C_{3-6}$-cycloalkylthio or aralkoxy each of which is optionally substituted with halogen; or
$NR_1R_2$ wherein $R_1$ represents hydrogen or $C_{1-3}$-alkyl and $R_2$ represents —$R_3$—(C=O)—$R_4$ wherein:
$R_3$ represents $C_{1-6}$-alkylene, $C_{2-6}$-alkenylene, $C_{4-6}$-cycloalkylene, $C_{4-6}$-cycloalkenylene, or arylene optionally substituted with one or more halogens;
$R_4$ represents aryl optionally substituted with one or more halogens; or
A is —O—A' or —S—A' wherein —O— or —S— is linked to X in formula (I) and wherein A' is $C_{1-3}$-alkylene which is optionally substituted with one or more substituents selected from
halogen or
$C_{1-3}$-alkyl, $C_{1-6}$-alkoxy, $C_{3-6}$-cycloalkoxy, $C_{1-6}$-alkylthio, $C_{3-6}$-cycloalkylthio or aralkoxy each of which is optionally substituted with halogen; or
$NR_1R_2$ wherein $R_1$ represents hydrogen or $C_{1-3}$-alkyl and $R_2$ represents —$R_3$—(C=O)—$R_4$ wherein:
$R_3$ represents $C_{1-6}$-alkylene, $C_{2-6}$-alkenylene, $C_{4-6}$-cycloalkylene, $C_{4-6}$-cycloalkenylene, or arylene optionally substituted with one or more halogens;
$R_4$ represents aryl optionally substituted with one or more halogens; and
B is $C_{1-3}$-alkylene which is optionally substituted with one or more substituents selected from
halogen or
$C_{1-3}$-alkyl, $C_{1-6}$-alkoxy, $C_{3-6}$-cycloalkoxy, $C_{1-6}$-alkylthio, $C_{3-6}$-cycloalkylthio or aralkoxy each of which is optionally substituted with halogen; or
$NR_1R_2$ wherein $R_1$ represents hydrogen or $C_{1-3}$-alkyl and $R_2$ represents —$R_3$—(C=O)—$R_4$ wherein:
$R_3$ represents $C_{1-6}$-alkylene, $C_{2-6}$-alkenylene, $C_{4-6}$-cycloalkylene, $C_{4-6}$-cycloalkenylene, or arylene optionally substituted with one or more halogens;
$R_4$ represents aryl optionally substituted with one or more halogens; or
B is —O—B' or —S—B' wherein —O— or —S— is linked to Y in formula (I) and wherein B' is $C_{1-3}$-alkylene which is optionally substituted with one or more substituents selected from
halogen or
$C_{1-3}$-alkyl, $C_{1-6}$-alkoxy, $C_{3-6}$-cycloalkoxy, $C_{1-6}$-alkylthio, $C_{3-6}$-cycloalkylthio or aralkoxy each of which is optionally substituted with halogen; or
$NR_1R_2$ wherein $R_1$ represents hydrogen or $C_{1-3}$-alkyl and $R_2$ represents —$R_3$—(C=O)—$R_4$ wherein:
$R_3$ represents $C_{1-6}$-alkylene, $C_{2-6}$-alkenylene, $C_{4-6}$-cycloalkylene, $C_{4-6}$-cycloalkenylene, or arylene optionally substituted with one or more halogens;
$R_4$ represents aryl optionally substituted with one or more halogens; and
D is H, $C_{1-6}$-alkyl or $C_{3-6}$-cycloalkyl; and
E is H, $C_{1-6}$-alkyl or $C_{3-6}$-cycloalkyl; and
L and M are independently —O— or —S—; and
T is $C_{3-9}$ divalent unsaturated carbon chain optionally substituted with one or more substituents selected from halogen or hydroxy; or
aryl, aralkoxy, $C_{1-3}$-alkoxy which is optionally substituted with halogen; and
U is $C_{3-9}$ divalent unsaturated carbon chain optionally substituted with one or more substituents selected from halogen or hydroxy; or
aryl, aralkoxy, $C_{1-3}$-alkoxy which is optionally substituted with halogen; and
X is arylene optionally substituted with one or more substituents selected from
halogen or hydroxy; or
$C_{1-6}$-alkyl, $C_{3-6}$-cycloalkyl, $C_{1-6}$-alkoxy, $C_{3-6}$-cycloalkoxy, $C_{1-6}$-alkylthio, $C_{3-6}$-cycloalkylthio each of which is optionally substituted with one or more halogen; or
Y is arylene optionally substituted with one or more substituents selected from
halogen or hydroxy; or
$C_{1-6}$-alkyl, $C_{3-6}$-cycloalkyl, $C_{1-6}$-alkoxy, $C_{3-6}$-cycloalkoxy, $C_{1-6}$-alkylthio, $C_{3-6}$-cycloalkylthio each of which is optionally substituted with one or more halogen; or
Z is arylene optionally substituted with one or more substituents selected from
halogen, oxo or hydroxy; or
$C_{1-6}$-alkyl, $C_{3-6}$-cycloalkyl, $C_{1-6}$-alkoxy, $C_{3-6}$-cycloalkoxy, $C_{1-6}$-alkylthio, $C_{3-6}$-cycloalkylthio each of which is optionally substituted with one or more halogen; or a pharmaceutically acceptable salt thereof, or a pharmaceutically acceptable solvate thereof, or any tautomeric forms, stereoisomers, mixture of stereoisomers racemic mixture, or polymorphs thereof.

2. A compound according to claim 1 wherein A is $C_{1-3}$-alkylene, which is optionally substituted with one or more substituents selected from
methyl, $C_{1-3}$-alkoxy, $C_{3-6}$-cycloalkoxy or benzyloxy each of which is optionally substituted with halogen; or
$NR_1R_2$ wherein $R_1$ represents hydrogen and $R_2$ represents $-R_3-(C=O)-R_4$ wherein:
$R_3$ represents $C_{1-6}$-alkylene, $C_{2-6}$-alkenylene, $C_{4-6}$-cycloalkylene, $C_{4-6}$-cycloalkenylene, or phenylene optionally substituted with one or more halogens;
$R_4$ represents phenyl optionally substituted with one or more halogens.

3. A compound according to claim 2 wherein A is methylene or ethylene each of which is optionally substituted with one or more substituents selected from
methoxy or ethoxy; or
$NR_1R_2$ wherein $R_1$ represents hydrogen and $R_2$ represents $-R_3-(C=O)-R_4$ wherein $R_3$ and $R_4$ represents phenyl.

4. A compound according to claim 2 wherein A is ethylene which is optionally substituted with ethoxy.

5. A compound according to claim 1 wherein A is —O-A' or —S-A' wherein —O— or —S— is linked to X in formula (I) and wherein A' is $C_{1-3}$-alkylene which is optionally substituted with one or more substituents selected from
halogen or
$C_{1-3}$-alkyl, $C_{1-6}$-alkoxy, $C_{3-6}$-cycloalkoxy or aralkoxy each of which is optionally substituted with halogen.

6. A compound according to claim 5 wherein A is —O-A' or —S-A' wherein —O— or —S— is linked to X in formula (I) and wherein A' is methylene or ethylene each of which is optionally substituted with one or more substituents selected from methyl, methoxy or ethoxy.

7. A compound according to claim 1 wherein B is $C_{1-3}$-alkylene, which is optionally substituted with one or more substituents selected from
methyl, $C_{1-3}$-alkoxy, $C_{3-6}$-cycloalkoxy or benzyloxy each of which is optionally substituted with halogen; or
$NR_1R_2$ wherein $R_1$ represents hydrogen and $R_2$ represents $-R_3-(C=O)-R_4$ wherein:
$R_3$ represents $C_{1-6}$-alkylene, $C_{2-6}$-alkenylene, $C_{4-6}$-cycloalkylene, $C_{4-6}$-cycloalkenylene, or phenylene optionally substituted with one or more halogens;
$R_4$ represents phenyl optionally substituted with one or more halogens.

8. A compound according to claim 7 wherein B is methylene or ethylene each of which is optionally substituted with one or more substituents selected from
methoxy or ethoxy; or
$NR_1R_2$ wherein $R_1$ represents hydrogen and $R_2$ represents $-R_3-(C=O)-R_4$ wherein $R_3$ and $R_4$ represents phenyl.

9. A compound according to claim 7 wherein B is ethylene which is optionally substituted with ethoxy.

10. A compound according to claim 1 wherein B is —O—B' or —S—B' wherein —O— or —S— is linked to Y in formula (I) and wherein B' is $C_{1-3}$-alkylene which is optionally substituted with one or more substituents selected from
halogen or
$C_{1-3}$-alkyl, $C_{1-6}$-alkoxy, $C_{3-6}$-cycloalkoxy or aralkoxy each of which is optionally substituted with halogen.

11. A compound according to claim 10 wherein B is —O—B' or —S—B' wherein —O— or —S— is linked to Y in formula (I) and wherein B' is methylene or ethylene each of which is optionally substituted with one or more substituents selected from methyl, methoxy or ethoxy.

12. A compound according to claim 1 wherein D is H.

13. A compound according to claim 1 wherein D is methyl or ethyl.

14. A compound according to claim 1 wherein E is H.

15. A compound according claims 1 wherein E is methyl or ethyl.

16. A compound according to claim 1 wherein L is —O—.

17. A compound according to claim 1 wherein L is —S—.

18. A compound according to claim 1 wherein M is —O—.

19. A compound according to claim 1 wherein M is —S—.

20. A compound according to claim 1 wherein T is $C_{3-9}$ divalent unsaturated carbon chain optionally substituted with one or more substituents selected from phenyl, benzyloxy or $C_{1-3}$-alkoxy which is optionally substituted with halogen.

21. A compound according to claim 20 wherein T is an unsubstituted $C_{3-9}$ divalent unsaturated carbon chain.

22. A compound according to claim 20 wherein T is $C_{3-9}$ alkenylene.

23. A compound according to claim 20 wherein T is $C_{3-9}$ alkynylene.

24. A compound according to claim 20 wherein T is $C_{5-9}$ alkenynylene.

25. A compound according to claim 1 wherein U is $C_{3-9}$ divalent unsaturated carbon chain optionally substituted with one or more substituents selected from phenyl, benzyloxy or $C_{1-3}$-alkoxy which is optionally substituted with halogen.

26. A compound according to claim 25 wherein U is an unsubstituted $C_{3-9}$ divalent unsaturated carbon chain.

27. A compound according to claim 25 wherein U is $C_{3-9}$ alkenylene.

28. A compound according to claim 25 wherein U is $C_{3-9}$ alkynylene.

29. A compound according to claim 25 wherein U is $C_{5-9}$ alkenynylene.

30. A compound according to claim 1 wherein X is arylene optionally substituted with one or more substituents selected from
halogen or
$C_{1-6}$-alkyl optionally substituted with one or more halogen.

31. A compound according to claim 30 wherein X is phenylene optionally substituted with one or more substituents selected from
halogen or
$C_{1-3}$-alkyl optionally substituted with one or more halogen.

32. A compound according to claim 30 wherein X is phenylene optionally substituted with one or more halogen.

33. A compound according to claim 1 wherein Y is arylene optionally substituted with one or more substituents selected from
halogen or
$C_{1-6}$-alkyl optionally substituted with one or more halogen.

34. A compound according to claim 33 wherein Y is phenylene optionally substituted with one or more substituents selected from
halogen or
$C_{1-3}$-alkyl optionally substituted with one or more halogen.

35. A compound according to claims 1 wherein Y is phenylene optionally substituted with one or more halogen.

36. A compound according to claim 1 wherein Z is arylene optionally substituted with one or more substituents selected from
halogen, oxo or
$C_{1-6}$-alkyl, $C_{1-6}$-alkoxy each of which is optionally substituted with one or more halogen.

37. A compound according to claims 36 wherein Z is selected among the following groups:

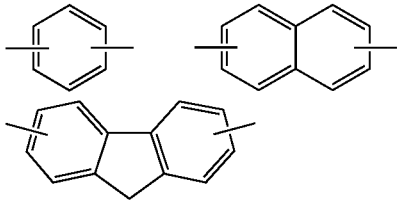

which is optionally substituted with one or more substituents selected from
halogen or
$C_{1-6}$-alkyl or $C_{1-6}$-alkoxy each of which is optionally substituted with one or more halogen.

38. A compound according to claim 36 wherein Z is selected among the following groups:

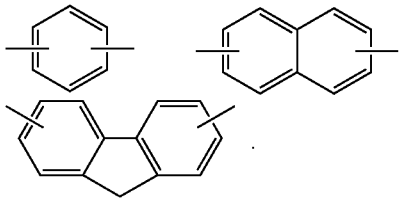

39. A compound according to claim 36 wherein Z is selected among the following groups:

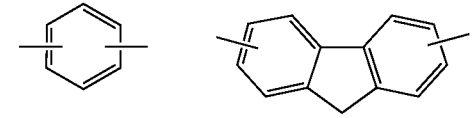

40. A compound according to claim 1 wherein the general formula (I) as described by the general formula (II):

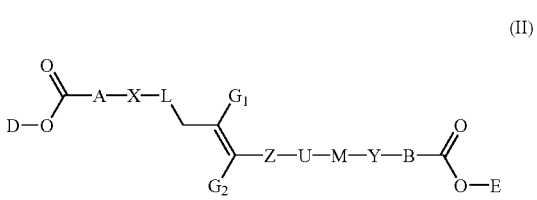

wherein D, A, X, L, Z, U, M, Y, B and E are as defined in claim 1; and $G_1$ is H, $C_{1-3}$-alkyl, $C_{1-3}$-alkoxy or $C_{1-3}$-aralkoxy each of which is optionally substituted with halogen; and
$G_2$ is H, $C_{1-3}$-alkyl, $C_{2-6}$-alkenyl, $C_{2-6}$-alkynyl, $C_{3-6}$-alkenynyl, aryl, aralkyl, $C_{1-3}$-alkoxy or $C_{1-3}$-aralkoxy each of which is optionally substituted with halogen; or
a pharmaceutically acceptable salt thereof, or a pharmaceutically acceptable solvate thereof, or any tautomeric forms, stereoisomers, mixture of stereoisomers, racemic mixture, or polymorphs thereof.

41. A compound according to claim 40 wherein $G_1$ is H, $C_{1-3}$-alkyl or $C_{1-3}$-alkoxy each of which is optionally substituted with halogen; and
$G_2$ is H, $C_{1-3}$-alkyl or aryl each of which is optionally substituted with halogen.

42. A compound according to claim 40 wherein $G_1$ is H and $G_2$ is H or methyl.

43. A compound according to claim 1 wherein the general formula (I) as described by the general formula (III):

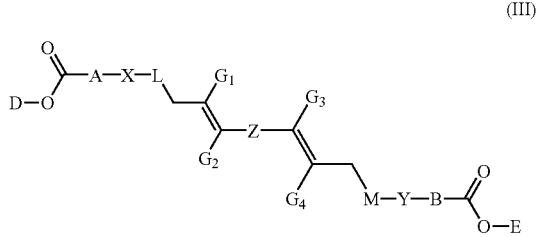

wherein D, A, X, L, Z, M, Y, B and E are as defined in claim 1; and
$G_1$ and $G_4$ independently of each other are H, $C_{1-3}$-alkyl, $C_{1-3}$-alkoxy or $C_{1-3}$-aralkoxy each of which is optionally substituted with halogen; and
$G_2$ and $G_3$ independently of each other is H, $C_{1-3}$-alkyl, $C_{2-6}$-alkenyl, $C_{2-6}$-alkynyl, $C_{3-6}$-alkenynyl, aryl, aralkyl, $C_{1-3}$-alkoxy or $C_{1-3}$-aralkoxy each of which is optionally substituted with halogen; or
a pharmaceutically acceptable salt thereof, or a pharmaceutically acceptable solvate thereof, or any tautomeric forms, stereoisomers, mixture of stereoisomers, racemic mixture, or polymorphs thereof.

44. A compound according to claim 43 wherein $G_1$ and $G_4$ independently of each other are H, $C_{1-3}$-alkyl or $C_{1-3}$-alkoxy each of which is optionally substituted with halogen; and
$G_2$ and $G_3$ independently of each other are is H, $C_{1-3}$-alkyl or aryl each of which is optionally substituted with halogen.

45. A compound according to claim 43 wherein $G_1$ and $G_4$ are H; and
$G_2$ and $G_3$ independently of each other are H or methyl.

46. A compound according to claim 1 wherein the general formula (I) as described by the general formula (IV):

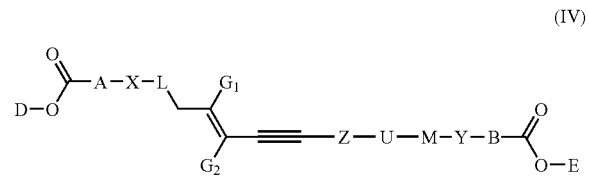

wherein D, A, X, L, Z, U, M, Y, B and E are as defined in claim 1; and $G_1$ is H, $C_{1-3}$-alkyl, $C_{1-3}$-alkoxy or $C_{1-3}$-aralkoxy each of which is optionally substituted with halogen; and $G_2$ is H, $C_{1-3}$-alkyl, $C_{2-6}$-alkenyl, $C_{2-6}$-alkynyl, $C_{3-6}$-alkenynyl, aryl, aralkyl, $C_{1-3}$-alkoxy or $C_{1-3}$-aralkoxy each of which is optionally substituted with halogen; or a pharmaceutically acceptable salt thereof, or a pharmaceutically acceptable solvate thereof, or any tautomeric forms, stereoisomers, mixture of stereoisomers, racemic mixture, or polymorphs thereof.

47. A compound according to claim 46 wherein $G_1$ is H, $C_{1-3}$-alkyl or $C_{1-3}$-alkoxy each of which is optionally substituted with halogen; and $G_2$ is H, $C_{1-3}$-alkyl or aryl each of which is optionally substituted with halogen.

48. A compound according to claim 46 wherein $G_1$ is H and $G_2$ is H or methyl.

49. A compound according to claim 1 wherein the general formula (I) as described by the general formula formula (V):

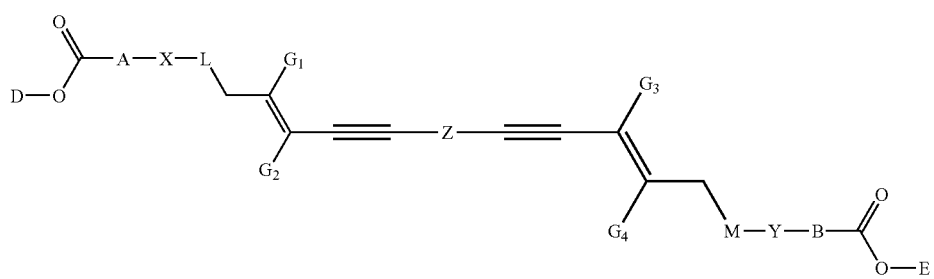

(V)

wherein D, A, X, L, Z, M, Y, B and E are as defined in claim 1; and $G_1$ and $G_4$ independently of each other are H, $C_{1-3}$-alkyl, $C_{1-3}$-alkoxy or $C_{1-3}$-aralkoxy each of which is optionally substituted with halogen; and $G_2$ and $G_3$ independently of each other is H, $C_{1-3}$-alkyl, $C_{2-6}$-alkenyl, $C_{2-6}$-alkynyl, $C_{3-6}$-alkenynyl, aryl, aralkyl, $C_{1-3}$-alkoxy or $C_{1-3}$-aralkoxy each of which is optionally substituted with halogen; or a pharmaceutically acceptable salt thereof, or a pharmaceutically acceptable solvate thereof, or any tautomeric forms, stereoisomers, mixture of stereoisomers, racemic mixture, or polymorphs thereof.

50. A compound according to claim 49 wherein $G_1$ and $G_4$ independently of each other are H, $C_{1-3}$-alkyl or $C_{1-3}$-alkoxy each of which is optionally substituted with halogen; and $G_2$ and $G_3$ independently of each other are H, $C_{1-3}$-alkyl or aryl each of which is optionally substituted with halogen.

51. A compound according to claim 49 wherein $G_1$ and $G_4$ are H; and $G_2$ and $G_3$ independently of each other are H or methyl.

52. The compound according to claim 1 which is:

2-Ethoxy-3-{4-[5-(4-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester;

3-{4-[5-(4-{5-[4-(2-Carboxy-2-ethoxy-ethyl)-phenoxy]-pent-3-en-1-ynyl}-phenyl)-pent-2-en-4-ynyloxy]-phenyl}-2-ethoxy-propionic acid;

3-Chloro-4-(5-{4-[5-(3-Chloro-4-ethoxycarbonylmethyl-phenoxy)-pent-3-en-1-ynyl]-phenyl}-pent-2-en-4-ynyloxy)-phenyl]-acetic acid ethyl ester;

[4-(5-{4-[5-(4-Carboxymethyl-3-chloro-phenoxy)-pent-3-en-1-ynyl]-phenyl}-pent-2-en-4-ynyloxy)-3-chloro-phenyl]-acetic acid;

2-Ethoxy-3-{4-[5-(3-{5-[4-(2-ethoxy-2-ethoxycarbonyl-ethyl)-phenoxy]-pent-3-en-1-ynyl}-phenyl)-pent-2-en-4-ynyloxy]-phenyl}-propionic acid ethyl ester;

3-{4-[5-(3-{5-[4-(2-Carboxy-2-ethoxy-ethyl)-phenoxy]-pent-3-en-1-ynyl}-phenyl)-pent-2-en-4-ynyloxy]-phenyl}-2-ethoxy-propionic acid;

[3-Chloyro-4-(5-{3-[5-(2-chloro-4-ethoxycarbonylm-ethyl-phenoxy)-pent-3-en-1-ynyl]-phenyl}-pent-2-en-4-ynyloxy)-phenyl]-acetic acid ethyl ester;

[4-(5-{3-[5-(4-Carboxymethyl-2-chloro-phenoxy)-pent-3-en-1-ynyl]-phenyl}-pent-2-en-4-ynyloxy)-3-chloro-phenyl]-acetic acid;

2-(2-Benzoyl-phenylamino)-3-(4-{5-[4-(5-{4-[2-(2-ben-zoyl-phenylamino)-2-methoxycarbonyl-ethyl]-phenoxy}-pent-3-en-1-ynyl)-phenyl]-pent-2-en-4-ynyloxy}-phenyl)-propionic acid methyl ester;

2-(2-Benzoyl-phenylamino)-3-(4-{5-[4-(5-{4-[2-(2-ben-zoyl-phenylamino)-2-carboxy-ethyl]-phenoxy}-pent-3-en-1-ynyl)-phenyl]-pent-2-en-4-ynyloxy}-phenyl)-propionic acid; or a salt thereof with a pharmaceutically acceptable acid or base, or any optical isomer or mixture of optical isomers, racemic mixture, or any tautomeric forms thereof.

53. The compound according to claim 1 which is:

[4-(3-{3-[3-(4-Methoxycarbonylmethyl-phenoxy)-prop-1-ynyl]-phenyl}-prop-2-ynyloxy)-phenyl]-acetic acid methyl ester;

[4-(3-{3-[3-(4-Methoxycarbonylmethyl-phenoxy)-prop-1-ynyl]-phenyl}-prop-2-ynyloxy)-phenyl]-acetic acid;

[4-(5-{4-[5-(4-Methoxycarbonylmethoxy-3-methyl-phenoxy)-pent-3-en-1-ynyl]-phenyl}-pent-2-en-4-ynyloxy)-2-methyl-phenoxy]-acetic acid methyl ester;

[4-(5-{4-[5-(4-Methoxycarbonylmethoxy-3-methyl-phenoxy)-pent-3-en-1-ynyl]-phenyl}-pent-2-en-4-ynyloxy)-2-methyl-phenoxy]-acetic acid;

3-{3-Bromo-4-[5-(4-{5-[2-bromo-4-(2-ethoxy-2-ethoxy-carbonyl-ethyl)-phenoxy]-pent-3-en-1-ynyl}-phenyl)-pent-2-en-4-ynyloxy]-phenyl}-2-ethoxy-propionic acid ethyl ester;

3-{3-Bromo-4-[5-(4-{5-[2-bromo-4-(2-ethoxy-2-ethoxy-carbonyl-ethyl)-phenoxy]-pent-3-en-1-ynyl}-phenyl)-pent-2-en-4-ynyloxy]-phenyl}-2-ethoxy-propionic acid;

[3-(5-{4-[5-(3-Ethoxycarbonylmethyl-phenoxy)-pent-3-en-1-ynyl]-phenyl}-pent-2-en-4-ynyloxy)-phenyl]-acetic acid ethyl ester;

[3-(5-{4-[5-(3-Ethoxycarbonylmethyl-phenoxy)-pent-3-en-1-ynyl]-phenyl}-pent-2-en-4-ynyloxy)-phenyl]-acetic acid;

2-Ethoxy-3-{4-[5-(4-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid ethyl ester;

2-Ethoxy-3-{4-[5-(4-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid;

2-Ethoxy-3-{4-[5-(3-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid ethyl ester;

2-Ethoxy-3-{4-[5-(3-{5-[4-(2-ethoxy-2-ethoxycarbonyl-ethyl)-phenoxy]-3-methyl-pent-3-en-1-ynyl}-phenyl)-3-methyl-pent-2-en-4-ynyloxy]-phenyl}-propionic acid;

[4-(3-{7-[3-(4-Methoxycarbonylmethoxy-3-methyl-phenylsulfanyl)-propenyl]-9H-fluoren-2-yl}-allylsulfanyl)-2-methyl-phenoxy]-acetic acid methyl ester; or a salt thereof with a pharmaceutically acceptable acid or base, or any optical isomer or mixture of optical isomers, racemic mixture, or any tautomeric forms thereof.

54. The compound according to claim 1, which is:

(4-(3-(7-(3-(4-Carboxymethoxy-3-methyl-phenylsulfanyl)-propenyl)-9H-fluoren-2-yl)-allylsulfanyl)-2-methyl-phenoxy)-acetic acid;

3-(4-(3-(7-(3-(4-carboxymethoxy-3-methyl-phenylsulfanyl)-propenyl)-9H-fluoren-2-yl)-allylsulfanyl)-phenyl)-2-ethoxy-propionic acid;

3-(4-(3-(7-(3-(4-carboxymethoxy-3-methyl-phenylsulfanyl)-propenyl)-9H-fluoren-2-yl)-allyloxy)-phenyl)-2-ethoxy-propionic acid;

(4-(3-(7-(3-(4-Carboxymethoxy-3-methyl-phenylsulfanyl)-propenyl)-9H-fluoren-2-yl)-allyloxy)-3-chloro-phenyl)-acetic acid;

3-(4-(3-(7-(3-(4-carboxymethoxy-2-chloro-phenoxy)-propenyl)-9H-fluoren-2-yl)-allylsulfanyl)-phenyl)-2-ethoxy-propionic acid;

3-(4-(3-(7-(3-(4-carboxymethoxy-2-chloro-phenoxy)-propenyl)-9H-fluoren-2-yl)-allyloxy)-phenyl)-2-ethoxy-propionic acid;

3-(4-(3-(7-(3-(4-(2-Carboxy-2-ethoxy-ethyl)-phenoxy)-propenyl)-9H-fluoren-2-yl)-allyloxy)-phenyl)-2-ethoxy-propionic acid;

3-(4-(3-(7-(3-(4-(2-Carboxy-2-ethoxy-ethyl)-phenylsulfanyl)-propenyl)-9H-fluoren-2-yl)-allylsulfanyl)-phenyl)-2-ethoxy-propionic acid;

(4-(3-(7-(3-(4-Carboxymethoxy-2-chloro-phenyxy)-propenyl)-9H-fluoren-2-yl)-allyloxy)-3-chloro-phenyl)-acetic acid;

3-(4-(5-(4-(5-(4-(2-Carboxy-2-ethoxy-ethyl)-phenoxy)-pent-3-en-1-ynyl)-phenyl)-pent-2-en-4-ynyloxy)-phenyl)-2-ethoxy-propionic acid;

3-(4-(5-(4-(5-(4-(2-Carboxy-2-ethoxy-ethyl)-phenylsulfanyl)-pent-3-en-1-ynyl)-phenyl)-pent-2-en-4-ynylsulfanyl)-phenyl)-2-ethoxy-propionic acid;

4-(5-(4-(5-(4-Carboxymethyl-2-chloro-phenoxy)-pent-3-en-1-ynyl)-phenyl)-pent-2-en-4-ynyloxy)-3-chloro-phenyl)-acetic acid;

4-(5-(4-(5-(4-Carboxymethyl-3-methyl-phenylsulfanyl)-pent-3-en-1-ynyl)-phenyl)-pent-2-en-4-ynylsulfanyl)-2-methyl-phenoxy)-acetic acid;

3-(4-(5-(4-(5-(4-Carboxymethoxy-3-methyl-phenylsulfanyl)-pent-3-en-1-ynyl)-phenyl)-pent-2-en-4-ynylsulfanyl)-phenyl)-2-ethoxy-propionic acid;

3-(4-(5-(4-(5-(4-Carboxymethoxy-3-methyl-phenylsulfanyl)-pent-3-en-1-ynyl)-phenyl)-pent-2-en-4-ynyloxy)-phenyl)-2-ethoxy-propionic acid;

(4-(5-(4-(5-(4-Carboxymethyl-2-chloro-phenoxy)-3-methyl-pent-3-en-1-ynyl)-phenyl)-3-methyl-pent-2-en-4-ynyloxy)-3-chloro-phenyl)-acetic acid;

(4-(5-(4-(5-(4-Carboxymethyl-3-methyl-phenylsulfanyl)-3-methyl-pent-3-en-1-ynyl)-phenyl)-3-methyl-pent-2-en-4-ynylsulfanyl)-2-methyl-phenoxy)-acetic acid;

3-(4-(5-(4-(5-(4-(2-Carboxy-2-ethoxy-ethyl)-phenoxy)-3-methyl-pent-3-en-1-ynyl)-phenyl)-3-methyl-pent-2-en-4-ynyloxy)-phenyl-2-ethoxy-propionic acid;

3-(4-(5-(4-(5-(4-(2-Carboxy-2-ethoxy-ethyl)-phenylsulfanyl)-3-methyl-pent-3-en-1-ynyl)-phenyl)-3-methyl-pent-2-en-4-ynylsulfanyl)-phenyl-2-ethoxy-propionic acid;

3-(4-(5-(4-(5-(4-(2-Carboxy-2-ethoxy-ethyl)-phenylsulfanyl)-3-methyl-pent-3-en-1-ynyl)-phenyl)-3-methyl-pent-2-en-4-ynyloxy)-phenyl-2-ethoxy-propionic acid;

3-(4-(5-(4-(5-(4-Carboxymethoxy-3-methyl-phenylsulfanyl)-3-methyl-pent-3-en-1-ynyl)-phenyl)-3-methyl-pent-2-en-4-ynylsulfanyl)-phenyl-2-ethoxy-propionic acid;

3-(4-(5-(4-(5-(4-Carboxymethoxy-3-methyl-phenylsulfanyl)-3-methyl-pent-3-en-1-ynyl)-phenyl)-3-methyl-pent-2-en-4-ynyloxyl)-phenyl-2-ethoxy-propionic acid;

3-(4-(5-(3-(5-(4-(2-Carboxy-2-ethoxy-ethyl)-phenoxy)-pent-3-en-1-ynyl)-phenyl)-pent-2-en-4-ynyloxy)-phenyl)-2-ethoxy-propionic acid;

3-(4-(5-(3-(5-(4-(2-Carboxy-2-ethoxy-ethyl)-phenylsulfanyl)-pent-3-en-1-ynyl)-phenyl)-pent-2-en-4-ynylsulfanyl)-phenyl)-2-ethoxy-propionic acid;

4-(5-(3-(5-(4-Carboxymethyl-2-chloro-phenoxy)-pent-3-en-1-ynyl)-phenyl)-pent-2-en-4-ynyloxy)-3-chloro-phenyl)-acetic acid;

4-(5-(3-(5-(4-Carboxymethyl-3-methyl-phenylsulfanyl)-pent-3-en-1-ynyl)-phenyl)-pent-2-en-4-ynylsulfanyl)-2-methyl-phenoxy)-acetic acid;

3-(4-(5-(3-(5-(4-Carboxymethoxy-3-methyl-phenylsulfanyl)-pent-3-en-1-ynyl)-phenyl)-pent-2-en-4-ynylsulfanyl)-phenyl)-2-ethoxy-propionic acid;

3-(4-(5-(3-(5-(4-Carboxymethoxy-3-methyl-phenylsulfanyl)-pent-3-en-1-ynyl)-phenyl)-pent-2-en-4-ynyloxy)-phenyl)-2-ethoxy-propionic acid;

(4-(5-(3-(5-(4-Carboxymethyl-2-chloro-phenoxy)-3-methyl-pent-3-en-1-ynyl)-phenyl)-3-methyl-pent-2-en-4-ynyloxy)-3-chloro-phenyl)-acetic acid;

(4-(5-(3-(5-(4-Carboxymethyl-3-methyl-phenylsulfanyl)-3-methyl-pent-3-en-1-ynyl)-phenyl)-3-methyl-pent-2-en-4-ynylsulfanyl)-2-methyl-phenoxy)-acetic acid;

3-(4-(5-(3-(5-(4-(2-Carboxy-2-ethoxy-ethyl)-phenoxy)-3-methyl-pent-3-en-1-ynyl)-phenyl)-3-methyl-pent-2-en-4-ynyloxy)-phenyl-2-ethoxy-propionic acid;

3-(4-(5-(3-(5-(4-(2-Carboxy-2-ethoxy-ethyl)-phenylsulfanyl)-3-methyl-pent-3-en-1-ynyl)-phenyl)-3-methyl-pent-2-en-4-ynylsulfanyl)-phenyl-2-ethoxy-propionic acid;

3-(4-(5-(3-(5-(4-(2-Carboxy-2-ethoxy-ethyl)-phenylsulfanyl)-3-methyl-pent-3-en-1-ynyl)-phenyl)-3-methyl-pent-2-en-4-ynyloxy)-phenyl-2-ethoxy-propionic acid;

3-(4-(5-(3-(5-(4-Carboxymethoxy-3-methyl-phenylsulfa-nyl)-3-methyl-pent-3-en-1-ynyl)-phenyl)-3-methyl-pent-2-en-4-ynylsulfanyl)-phenyl-2-ethoxy-propionic acid;

3-(4-(5-(3-(5-(4-Carboxymethoxy-3-methyl-phenylsulfa-nyl)-3-methyl-pent-3-en-1-ynyl)-phenyl)-3-methyl-pent-2-en-4-ynyloxy)-phenyl-2-ethoxy-propionic acid;

3-(4-(5-(7-(5-(4-(2-Carboxy-2-ethoxy-ethyl)-phenoxy)-3-methyl-pent-3-en-1-ynyl)-9H-fluoren-2-yl)-3-methyl-pent-2-en-4-ynyloxy)-phenyl)-2-ethoxy-propionic acid;

3-(4-(5-(7-(5-(4-(2-Carboxy-2-ethoxy-ethyl)-phensulfa-nyl)-3-methyl-pent-3-en-1-ynyl)-9H-fluoren-2-yl)-3-methyl-pent-2-en-4-ynylsulfanyl)-phenyl)-2-ethoxy-propionic acid;

(4-(5-(7-(5-(4-Carboxymethoxy-3-methyl-phenylsulfa-nyl)-3-methyl-pent-3-en-1-ynyl)-9H-fluoren-2-yl)-3-methyl-pent-2-en-4-ynylsulfanyl)-2-methyl-phenoxy)-acetic acid;

3-(4-(5-(7-(5-(4-(2-Carboxy-2-ethoxy-ethyl)-phenoxy-pent-3-en-1-ynyl)-9H-fluoren-2-yl)-3-methyl-pent-2-en-4-ynyloxy)-phenyl)-2-ethoxy-propionic acid;

3-(4-(5-(7-(5-(4-(2-Carboxy-2-ethoxy-ethyl)-phensulfa-nyl-pent-3-en-1-ynyl)-9H-fluoren-2-yl)-3-methyl-pent-2-en-4-ynylsulfanyl)-phenyl)-2-ethoxy-propionic acid;

(4-(5-(7-(5-(4-Carboxymethoxy-3-methyl-phenylsulfa-nyl)-pent-3-en-1-ynyl)-9H-fluoren-2-yl)-3-methyl-pent-2-en-4-ynylsulfanyl)-2-methyl-phenoxy)-acetic acid;

3-(4-(5-(7-(5-(4-(2-Carboxy-2-ethoxy-ethyl)-phenoxy-pent-3-en-1-ynyl)-9H-fluoren-2-yl)-3-methyl-pent-2-en-4-ynyloxy)-phenyl)-2-ethoxy-propionic acid;

a salt thereof with a pharmaceutically acceptable acid or base, or any optical isomer or mixture of optical isomers, racemic mixture, or any tautomeric forms thereof.

55. A pharmaceutical composition comprising, as an active ingredient, at least one compound according to claim 1 together with one or more pharmaceutically acceptable carriers or excipients.

56. A pharmaceutical composition according to claim 55 in unit dosage form, comprising from about 0.05 mg to about 1000 mg per day of compound.

57. A pharmaceutical composition for the treatment of conditions mediated by the Peroxisome Proliferator-Activated Receptors (PPAR), the composition comprising a compound according to claim 1 together with one or more pharmaceutically acceptable carriers or excipients.

58. A pharmaceutical composition for the treatment of type I diabetes, type II diabetes, dyslipidemia, syndrome X, metabolic syndrome, impaired glucose tolerance, insulin resistance, hypertrigyceridaemia and/or obesity, cardiovascular diseases, atherosclerosis or hypercholesteremia comprising a compound according to claim 1 together with one or more pharmaceutically acceptable carriers or excipients.

59. A pharmaceutical composition according to claim 55 for oral, nasal, transdermal, pulmonal, or parenteral administration.

60. A method for the treatment of conditions mediated by the Peroxisome Proliferator-Activated Receptors (PPAR), the method comprising administering to a subject in need thereof an effective amount of a compound according to claim 1 or a pharmaceutical composition comprising the same.

61. A method for the treatment of type I diabetes, type II diabetes, dyslipidemia, syndrome X, metabolic syndrome, impaired glucose tolerance, insulin resistance, hypertrigyceridaemia and/or obesity, cardiovascular diseases atherosclerosis or hypercholesteremia, the method comprising administering to a subject in need thereof an effective amount of a compound according to claim 1 or of a pharmaceutical composition comprising the same.

62. The method according to claim 60 wherein the effective amount of the compound is in the range of from about 0.05 mg to about 1000 mg per day.

63. The method according to claim 61 wherein the effective amount of the compound is in the range of from about 0.05 mg to about 1000 mg per day.

64. A pharmaceutical composition according to claim 56 in unit dosage form, comprising from about 0.1 to about 500 mg per day of the compound.

65. A pharmaceutical composition according to claim 64 in unit dosage form, comprising from about 0.5 mg to about 200 mg per day of the compound.

66. The method according to claim 62 wherein the effective amount of the compound is in the range of from about 0.1 to about 500 mg per day.

67. The method according to claim 66 wherein the effective amount of the compound is in the range of from about 0.5 mg to about 200 mg per day.

68. The method according to claim 63 wherein the effective amount of the compound is in the range of from about 0.1 to about 500 mg per day.

69. The method according to claim 68 wherein the effective amount of the compound is in the range of from about 0.5 mg to about 200 mg per day.

* * * * *